(12) United States Patent
Kamiya et al.

(10) Patent No.: US 10,753,839 B2
(45) Date of Patent: Aug. 25, 2020

(54) MEASUREMENT DEVICE AND METHOD FOR ESTIMATING MOUTHFEEL AND BEHAVIOR OF ALIMENTARY BOLUS DURING EATING AND SWALLOWING

(71) Applicant: Meiji Co., Ltd., Chuo-ku, Tokyo (JP)

(72) Inventors: Tetsu Kamiya, Odawara (JP); Nobuko Jinno, Odawara (JP); Megumi Takai, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 405 days.

(21) Appl. No.: 15/750,684

(22) PCT Filed: Jul. 12, 2016

(86) PCT No.: PCT/JP2016/003299
§ 371 (c)(1),
(2) Date: Feb. 6, 2018

(87) PCT Pub. No.: WO2017/026090
PCT Pub. Date: Feb. 16, 2017

(65) Prior Publication Data
US 2018/0224365 A1 Aug. 9, 2018

(30) Foreign Application Priority Data

Aug. 7, 2015 (JP) .................................. 2015-156529
Jul. 1, 2016 (JP) .................................. 2016-131867

(51) Int. Cl.
| | |
|---|---|
| G01N 11/02 | (2006.01) |
| G01N 33/02 | (2006.01) |
| G01N 11/00 | (2006.01) |
| G06K 9/00 | (2006.01) |
| H04N 5/247 | (2006.01) |

(52) U.S. Cl.
CPC ............. *G01N 11/02* (2013.01); *G01N 11/00* (2013.01); *G01N 33/02* (2013.01); *G06K 9/00335* (2013.01); *H04N 5/247* (2013.01)

(58) Field of Classification Search
CPC ..................................................... G01N 11/02
USPC .......................................................... 702/19
See application file for complete search history.

(56) References Cited

U.S. PATENT DOCUMENTS

| | | | |
|---|---|---|---|
| 7,734,351 B2 | 6/2010 | Testerman et al. | |
| 8,936,471 B2 | 1/2015 | Evans | |
| 9,842,193 B2 | 12/2017 | Kamiya et al. | |
| 2015/0079570 A1 | 3/2015 | Michiwaki et al. | |
| 2015/0132723 A1 | 5/2015 | Evans | |

FOREIGN PATENT DOCUMENTS

| | | |
|---|---|---|
| CN | 101616711 A | 12/2009 |
| CN | 103596498 A | 2/2014 |
| JP | 2006-78477 A | 3/2006 |
| JP | 2011-064586 A | 3/2011 |
| JP | 2013-185903 A | 9/2013 |
| JP | 2013-202119 A | 10/2013 |
| WO | 2013/002380 A1 | 1/2013 |
| WO | 2013/146436 A1 | 10/2013 |

OTHER PUBLICATIONS

Extended European Search Report, dated Feb. 27, 2019, in European Patent Application No. EP 16 83 4794.
Office Action dated Sep. 4, 2019, in Chinese Patent Application No. 201680046549.1.
Iida et al., The Japanese Journal of Dysphagia Rehabilitation, Dec. 2009, pp. 215-224, vol. 13, No. 3, Japan.
International Search Report, dated Oct. 11, 2016, in International Application No. PCT/JP2016/003299.
International Preliminary Report on Patentability and Written Opinion, dated Feb. 22, 2018, in International Application No. PCT/JP2016/003299.

*Primary Examiner* — Jerry Lin
(74) *Attorney, Agent, or Firm* — Wood, Phillips, Katz, Clark & Mortimer

(57) ABSTRACT

The present invention is directed to development of a device which makes it possible to precisely and easily measure, evaluate, and quantify dynamic properties of an alimentary bolus by simulating swallowing of a wide variety of types of food products, and also directed to a method to estimate mouthfeel from the dynamic properties by use of the device. The above measurement device to simulatively reproduce a state of the swallowing of the alimentary bolus, and to measure motion and shape of a specimen as a simulative alimentary bolus, comprises a tilted plate having a tilted surface; a supply unit (a) to supply the specimen onto the tilted surface; a supply sensor (c) to detect the specimen supplied from the supply unit (a) onto the tilted surface; arrival sensors (d, f) to detect the specimen downwardly flowing through a predetermined site on the tilted surface; a data logger (i) to record an output from each of the sensors; an upper camera (h) to image, from a position above the tilted surface, the specimen downwardly flowing on the tilted surface, to produce an upper image; a side camera (g) to image, from a side of the tilted surface, the specimen downwardly flowing on the tilted surface, to produce a side image; and a calculation unit which uses at least one of the output from the data logger (i), the side image, and the upper image to calculate a state parameter that represents a state of the specimen downwardly flowing on the tilted surface.

13 Claims, 33 Drawing Sheets

MEASUREMENT DEVICE AND METHOD FOR ESTIMATING MOUTHFEEL AND BEHAVIOR OF ALIMENTARY BOLUS DURING EATING AND SWALLOWING

TECHNICAL FIELD

The present invention relates to a device which measures properties to estimate behavior and mouthfeel of an alimentary bolus during eating and swallowing. The present invention also relates to a method to obtain dynamic properties by use of a simulative swallowing phenomenon realized by the device.

BACKGROUND ART

The third cause of death of the Japanese people is pneumonia, and 90% or more of pneumonia of elderly people is said to be aspiration pneumonia. When elderly people suffer from pneumonia, they may be hospitalized for a longer time, rapidly deteriorate in physical strength and the like, and have a risk of becoming frail (a state of being declined in muscular strength and vitality due to advanced age), suffering from sarcopenia (a phenomenon of age-related muscular decline), and the like. For the extension of healthy life expectancy and the restraint of medical costs, attention is being paid to the mechanism of a living body during swallowing and to behavior of an alimentary bolus during swallowing.

Swallowing is a reflex motion to send food (including drinks) taken into the oral cavity, to the stomach through the pharynx and the esophagus. During swallowing, muscles of the oral cavity, the pharynx, the larynx, and the esophagus act in a set order within a short time, and achieve a complicated motion.

As a technique to simulate behavior of an alimentary bolus during swallowing, there has heretofore been disclosed a swallowing dynamic state simulator using a computer (PATENT LITERATURES 1 and 2). PATENT LITERATURE 1 discloses a swallowing simulation device which includes oral cavity modeling, an organ properties setting unit, an organ motion setting unit, a food physical properties setting unit, a motion unit, a physical properties deciding unit, and a control unit.

A swallowing dynamic state and alimentary bolus behavior can be simulated on a computer. It is possible to extract an alimentary bolus downward flow velocity during swallowing, acceleration, shear velocity, shear stress, viscosity of food, force on living body organs, energy, and others. Not only data at a given time and position but also changes in physical quantity during a swallowing operation can be extracted, and then visualized and quantified.

PATENT LITERATURE 2 discloses a swallowing simulation device which includes a head and neck modeling unit, an organ motion setting unit, an oral ingestion material physical properties setting unit, an input unit to input a false oral ingestion material into the oral cavity; a motion analysis unit, a physical properties deciding unit, and a control unit.

A swallowing dynamic state and alimentary bolus behavior can be simulated on a computer. It is possible to extract an alimentary bolus downward flow velocity during swallowing, acceleration, shear velocity, shear stress, viscosity of food, force on living body organs, energy, and others. Not only data at a given time and position but also changes with time in physical quantity during swallowing operation can be extracted, and then visualized and quantified.

Another technique to simulate behavior of an alimentary bolus during swallowing can measure fall velocity, fall aspect, and a fall path of a false food by use of a full-scale oropharyngeal model manufactured by a powder deposition method. There is disclosed a method to compute a velocity on the basis of a contrast photograph of swallowing (refer to NONPATENT LITERATURE 1).

Furthermore, a measurement method of physical quantity directed to micro liquid droplets is disclosed as measurement that considers water repellency (or wettability) of food and a wall surface (PATENT LITERATURES 3 and 4). PATENT LITERATURE 3 discloses an evaluation device for wettability including a light source which illuminates a specimen from above, an upper surface measurement camera which sends upper video data resulting from photography of the specimen from above to a personal computer main unit, a light source which illuminates the specimen from the side, a camera which sends side video data resulting from sidewise photography to the personal computer main unit, a specimen stage which adjusts droplet hitting positions on a liquid specimen or a solid specimen, and the personal computer main unit which calculates the video data. This device can capture a liquid droplet from the side and then measure and compute a contact angle, a liquid diameter, a liquid height, and a liquid amount, and can also capture the liquid droplet from its upper surface photographed simultaneously with its side surface and then evaluate the circularity of the liquid droplet and the water repellency dependent on a wet area.

PATENT LITERATURE 4 discloses a measurement method of liquid droplet moving behavior to measure, with a camera, the acceleration of one point on a moving direction side, between two points on both sides of the intersection of a liquid droplet outer periphery and a solid substance surface seen from the side of the moving direction when the liquid droplet moves on a fixed surface. A dynamic contact angle based on a dynamic falling method can be measured; and movement distance, velocity, acceleration, and the upper surface can be observed, so that shear velocity and shear stress can be measured from a velocity distribution of flux inside the liquid droplet.

CITATION LIST

Patent Literatures

[PATENT LITERATURE 1] WO 2013/146436 A1
[PATENT LITERATURE 2] JP 2013-202119 A
[PATENT LITERATURE 3] JP 2011-064586 A
[PATENT LITERATURE 4] JP 2006-078477 A

Nonpatent Literature

[NONPATENT LITERATURE 1] Iida et al., The Japanese Journal of Dysphagia Rehabilitation, 13, 3, p. 215 to 224, 2009

SUMMARY OF INVENTION

Technical Problem

The inventor has developed a swallowing dynamic state simulator using a computer to simulate behavior of an alimentary bolus during swallowing (refer to PATENT LITERATURES 1 and 2). The swallowing dynamic state simulator has been found to be considerably high in precision as compared with medical images such as a swallowing contrast image. Therefore, various physical quantities (such as velocity, acceleration, pressure, force, and shear stress), and the shape of the alimentary bolus, and a downward flow path that are computed from this simulator are considered to be relatively correct. On the other hand, actual swallowing operates in accordance with the physical properties of food, and a swallowing model adapted to the physical properties of food needs to be created in order to analyze the physical properties of food by the swallowing dynamic state simulator, Because the creation of the swallowing model requires much time and labor, several models can only be created a year by the present technology. Thus, performing a detailed computer simulation adapted to each of various kinds of foods and the living body shape of a patient is not realistic under the present technology.

Accordingly, it is possible to consider a method to measure the fall velocity, fall shape, and fail locus of a false alimentary bolus by use of a fixed model (immobile plaster model) having a precise oropharyngeal shape created by a powder deposition method, such as the one in NONPATENT LITERATURE 1. However, this method requires the measurement of the velocity and others from the medical image that is low in time and spatial resolutions (a time resolution of about $\frac{1}{10}$ to $\frac{1}{30}$ sec, and a spatial resolution of about 0.5 to 1 mm), so that problems remain in terms of precision. Moreover, it is known from results of a computer simulation that a swallowing phenomenon is closely related to the water repellency (or wettability) of the wall surface, but it is difficult to change the physical properties of the wall by the method according to NONPATENT LITERATURE 1. In addition, according to this method, information on the velocity, fall shape, and fall locus can only be extracted, and measurement of other dynamic physical quantities is difficult.

The methods according to PATENT LITERATURES 3 and 4 directed to micro liquid droplets are common as measurement that considers the water repellency (or wettability) of food and the wall surface. The problem common to both of the measurement methods is that the value of physical quantity of a liquid droplet to be measured varies according to the size of the diameter of the liquid droplet. That is, the actual scale of the alimentary bolus (macroscale: an alimentary bolus of mL order) is 1000 times or more different from the scale of measurement (microscale: a liquid droplet of μL order), so that various properties measured by these general-purpose measurement instruments do not correspond to the actual properties of the swallowing of the alimentary bolus.

The problems of the individual techniques are put in order. The measurement instrument according to PATENT LITERATURE 3 can capture a micro liquid droplet of μL order from its side surface and measure and compute a contact angle, a liquid diameter, a liquid height, and a liquid amount, and can also evaluate the circularity of the liquid droplet captured from its simultaneously photographed upper surface, and the water repellency dependent on a wet area. That is, the advantage of this technique is that the water repellency (wettability) of the liquid droplet can be observed in multiple phases. However, this technique only observes a phenomenon on a fixed plate, and has difficulty in measuring the macroscale alimentary bolus when it dynamically moves.

On the other hand, the measurement instrument according to PATENT LITERATURE 4 can measure the dynamic contact angle based on the dynamic falling method, and measure shear velocity and shear stress from the movement distance, velocity, acceleration, and the velocity distribution of flux inside the liquid droplet, regarding a micro liquid droplet. However, this measurement instrument basically measures in a sideward direction, and does not assume simultaneous measurement from different two directions regarding the macroscale alimentary bolus.

It is therefore a challenge to provide a measurement device which can adapt to materials having various food physical properties and wall surface property values and which has considerably high precision in terms of time and spatial resolutions and which can measure, evaluate, and digitalize, from multiple directions and in multiple phases, dynamic physical quantity and property value during dynamic movement regarding the macroscale alimentary bolus close to the actual order of drinking amount, that is, to provide a measurement device and a measurement method which simulate a phenomenon (state) of eating and swallowing and then quantitatively measure (estimate) behavior and mouthfeel of an alimentary bolus.

Solution to Problem

The inventor disposed a material which simulates a living body surface on a tilted plate, supplied a predetermined amount of specimen thereon, and captured behavior of the specimen downwardly flowing or falling on the tilted surface in multiple phases with a plurality of sensors and a plurality of cameras, thereby discovering that a false swallowing phenomenon could be precisely, quantitatively, and validly measured, and completing the present invention.

That is, a measurement device according to the present invention is a measurement device to simulatively reproduce a state of the swallowing of an alimentary bolus, and to measure motion and shape of a specimen as an alimentary bolus. The measurement device comprises a tilted member having a tilted surface; a supply unit to supply the specimen onto the tilted surface; a supply sensor to detect the specimen supplied from the supply unit onto the tilted surface; arrival sensors to detect the specimen downwardly flowing or falling through a predetermined site on the tilted surface; a timing recording unit to record a detection timing of the specimen by the supply sensor and the arrival sensor; an upper camera to image, from a position above the tilted surface, the specimen moving on the tilted surface, to produce an upper image; a side camera to image, from a side of the tilted surface, the specimen downwardly flowing or falling on the tilted surface, to produce a side image; and a calculation unit which uses at least one of the output from the timing recording unit, the side image, and the upper image, to calculate state parameters which represent states of the specimen downwardly flowing or falling on the tilted surface.

Advantageous Effects of the Invention

According to the present invention, it is possible to provide a device which precisely and quantitatively measures and evaluates behavior (dynamic physical properties) of an alimentary bolus during eating and swallowing regarding various kinds of foods. This measured physical property value can be used in initial data necessary for a simulation of a swallowing dynamic state using a computer. Further, the value can be used to objectively evaluate and check validity of a computation result of the simulation of the swallowing dynamic state while comparing the simulation of the swallowing dynamic state with the dynamic physical properties. Further, the value can be used to objectively evaluate and check validity of an analytic result of a sensory evaluation while comparing the dynamic physical properties with the sensory evaluation value. Moreover, if the dynamic physical properties are linked to the sensory evaluation, mouthfeel which has been dependent on the sensory evaluation alone can be more objectively evaluated. In addition, it is possible to estimate, from the dynamic physical properties, mouthfeel or the like that easily suits to people having difficulty in eating and swallowing (elderly people or the like), and utilize the estimation in designing (development and improvement) of foods that are required accordingly.

DESCRIPTION OF EMBODIMENTS

Figure 1:
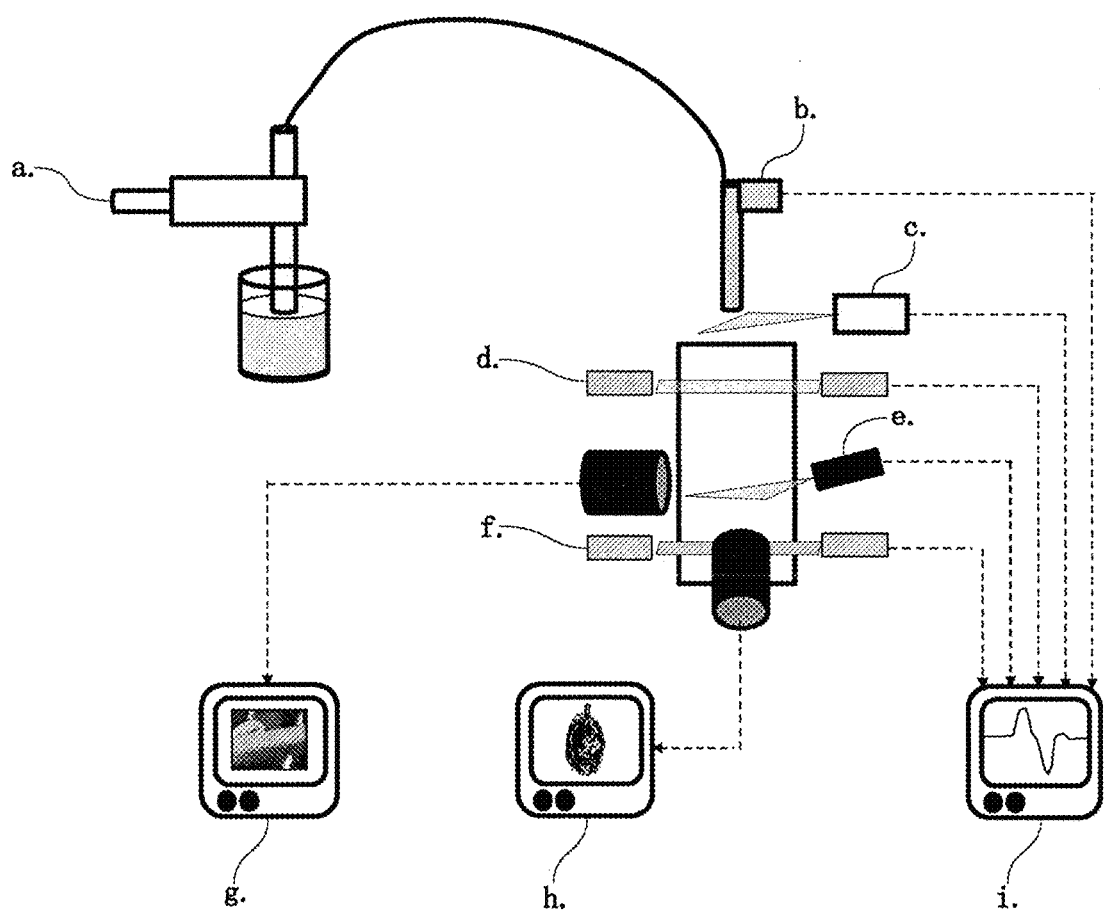
FIG. 1 shows a schematic diagram of a measurement device for properties of eating and swallowing.

A measurement device according to the present embodiment is shown in FIG. 1. The present measurement device is a measurement device to simulatively reproduce a state of the swallowing of an alimentary bolus, and to measure motion and shape of a specimen as a simulative alimentary bolus. As shown in this diagram, the present measurement device includes a tilted portion plate having a tilted surface of 150 mm×100 mm, a supply unit (a) to supply the specimen onto the tilted surface, a supply sensor (c) to detect the specimen supplied from the supply unit (a) onto the tilted surface, arrival sensors (d), (e), and (f) to detect the specimen downwardly flowing or falling through a predetermined site on the tilted surface; a data logger (i) to record an output from each of the sensors (c), (d), (e), and (f) as a timing recording unit to record a detection timing of the specimen by the supply sensor (c) and the arrival sensors (d), (e), and (f), an upper camera (h) to image, from a position above the tilted surface, the specimen downwardly flowing or failing on the tilted surface, to produce an upper image, a side camera (g) to image, from a side of the tilted surface, the specimen downwardly flowing or falling on the tilted surface, to produce a side image; and a calculation unit (a computer, not shown) which uses at least one of the output from the data logger, the side image, and the upper image to calculate state parameters that represent states of the specimen downwardly flowing or falling on the tilted surface.

The supply unit (a) includes a nozzle disposed above the tilted surface, and a piston pump (a) which supplies a predetermined amount of specimen to the nozzle. Although the tip of the nozzle is disposed 25 mm from the tilted surface above the tilted surface, any position and height of the nozzle can be set. Further, a pressure sensor (b) to detect pressure inside the nozzle is attached to the nozzle.

The arrival sensors include an upper arrival check sensor (upper sensor) (d), a lower arrival check sensor (lower sensor) (f), and a middle arrival check sensor (middle sensor) (e).

The upper arrival check sensor (d) detects the specimen downwardly flowing or falling through a first site on the tilted surface. The first site is a position 50 mm down from the upper edge of a tilted plate. The lower arrival check sensor (f) detects the specimen downwardly flowing or falling through a second site on the tilted surface.

The second site is a position 40 mm apart from a first predetermined sensor along a maximum tilt angle direction of the tilted surface. Further, the upper camera (h) images the specimen using an output from the upper arrival check sensor (d) as a trigger.

The middle arrival check sensor (e) detects the specimen downwardly flowing or falling through a third site between the first site and the second site. The third site is a position 20 mm down from the first site, and is exactly a midpoint between the first site and the second site. Further, the side camera (g) images the specimen using an output from the middle arrival check sensor (e) as a trigger.

Each of these sensors (d), (e), and (f) is an optical sensor to optically detect the specimen.

The measurement device to estimate dynamic behavior and/or mouthfeel of an alimentary bolus according to the present embodiment (hereinafter, the device according to the present invention) simultaneously and synchronously measures various dynamic properties regarding the alimentary bolus. That is, the present invention provides a device to quantitatively measure and evaluate each dynamic measurement value regarding the alimentary bolus while linking time, position, and shape. The device according to the present invention is capable of measuring and evaluating the dynamic physical properties of the alimentary bolus in a short time by a simple operation, and is still advantageous for its high precision and validity of measurement.

In the present embodiment, the alimentary bolus means a lump of food (including drinks) formed into a shape that is easily drunken by a person, or a shape or amount for one measurement by the device according to the present invention.

The specimen which is supplied onto the tilted surface preferably has a volume of 1 ml or more and 50 ml or less that is equal to the volume of the alimentary bolus to be orally taken at a time. Moreover, the specimen preferably has a mass of 1 m(g) or more and 50 m(g) or less.

In the present embodiment, the mouthfeel means sensation (tactile sense) of living body organs in the oral cavity including teeth and a tongue that move in response to mastication, among five senses that are felt when food is eaten.

In the present embodiment, the tilted surface of the tilted plate simulates the oral cavity, the pharynx, and the larynx during swallowing, so that the angle of the tilted surface can be suitably changed depending on information to be obtained. The tilted surface is tilted 30 to 80°, preferably 30 to 70°, still preferably 40 to 65°, and quite preferably 45 to 60°, with respect to, for example, a mounting surface.

The shape of the tilted plate can be suitably selected depending on the shape or amount of the specimen (alimentary bolus). For example, the shape includes a circular column, an elliptic column, a rectangular parallelepiped, and the shape of a complicated human living body organ manufactured by a three-dimensional printer or the like. The rectangular parallelepiped is preferable from the perspective that the sensors can be easily mounted parallel.

The size of the tilted plate can be suitably selected depending on the shape or amount of the specimen (alimentary bolus), One example that can be given is a rectangular parallelepiped having a diameter of 5 to 30 cm and a height of 0.2 to 2 cm, or having a length of 5 to 30 cm, a width of 2 to 10 cm, and a thickness of 0.2 to 2 cm.

The material of the tilted surface of the tilted plate has only to be suitably selected to have physical properties that simulate surfaces of the living body such as the oral cavity, the pharynx, and the larynx during swallowing. For example, one or more kinds of synthetic resins (silicon; urethane, epoxy resin, and iodinated polymer) and natural products (natural rubber) may be selected. The tilted plate may be manufactured by blending the synthetic resin and the natural rubber or the like at a ratio of predetermined amounts, and using processing such as heating, UV processing; cooling, plasma gas processing, coating processing, or the like, or using a 3D printer or the like. Moreover, the tilted plate may be made of two or more layers of different materials to facilitate stable measurement, the changes of the material and shape, and mounting.

Furthermore, the tilted surface of the tilted plate may be made of a false living body material (hydrophilic PVA) using polyvinyl alcohol (PVA). As hydrophilic PVA, for example, a water gel composition described in Japanese Patent Appln. KOKAI Publication No. 2007-31634 can be used. This water gel composition includes first PVA having a saponification degree of 97 mol % or more and a polymerization degree of 500 to 3000, and second PVA having a saponification degree of 70 to 90 mol % and a polymerization degree of 500 to 3000, and has a defined percentage of water content of 70 to 95 mol %. Moreover, a mixture of water, PVA, and dimethyl sulfoxide may be used as hydrophilic PVA.

In the present embodiment, the supply unit (a) which supplies the specimen has only to be in a form that can hold a certain amount of alimentary bolus (specimen) in an eating tool or a tube or the like. When a food such as jelly or pudding is a solid matter, the food has only to have a size that allows the food for one serve to be mounted on the eating tool. The supply unit (a) is made of a material resistant to conditions such as the amount of alimentary bolus (specimen) and the temperature and pH of the alimentary bolus (specimen). For example, the supply unit (a) includes a spoon of a synthetic resin. Moreover, in one aspect of the present invention, when the specimen is mounted on the eating tool or the like, it is preferable from the viewpoint of precision (reproducibility) to move the eating tool by a servo driver so that the specimen falls at a constant timing or velocity.

In the present embodiment, if the specimen is a gel-like or liquid food or a drink softer than a solid matter such as jelly or pudding, it is preferable to provide a structure and shape to correctly bring out (discharge) an amount for one serve of the supply unit at the same velocity so that an amount for one serve can be correctly brought out (discharged) at the same velocity. For example, it is possible to put a predetermined amount of specimen into a beaker, use a high-performance piston pump such as a model 2BC10J23 by HIBAR Corporation, and use, for the control of the pump, a controller such as a model UNIMATIC CP50 by HIBAR Corporation which pneumatically adjusts the piston. The specimen put in a container such as the beaker is self-sucked by the pump, and brought out (discharged) onto the tilted plate through the nozzle.

When the temperature of the specimen in the container needs to be a constant temperature, a constant temperature bath, an agitator, or the like may be attached. A middle part up to the nozzle may also be kept warm or warmed.

In the present embodiment, the supply sensor (c), that is, the discharge check sensor (c) of the supply unit is a sensor to detect the specimen which is supplied from the supply unit onto the tilted surface, i.e., a sensor to detect the time at which the alimentary bolus (specimen) is discharged. The supply check sensor (c) of the supply unit has only to be capable of measuring physical quantities such as force, pressure, vibration, and light with time. An optical sensor such as a photoelectric tube may be used. For example, as a laser sensor for discharge check, it is possible to use a sensor LV-NH42 and an amplifier LV-NIIMN by Keyence Corporation. Data such as an output value from the discharge check sensor (c) are automatically or manually transferred to a computer for data analysis.

In the present embodiment, the pressure sensor (b) of the supply unit is a sensor to detect the time at which the alimentary bolus (specimen) is discharged. The pressure sensor (b) of the supply unit has only to be capable of measuring, with time, the pressure of the alimentary bolus (specimen) in the supply unit. The pressure sensor (b) is preferably a sensor capable of detecting a slight amount of pressure of mL order of food. For example, the sensor includes (A)P-10S by Keyence Corporation, and the amplifier includes (A)P-V80 by Keyence Corporation. It is preferable that data such as an output value from the pressure sensor (b) are automatically or manually transferred to the computer for data analysis.

In the present embodiment, the cameras which capture the shape of the alimentary bolus (specimen) have the function of capturing the motion of the subject (specimen) via a lens with an image pickup device (a CCD or the like), processing the image, and recording the image whenever a time elapses. In order to capture the area and shape of the alimentary bolus (specimen) that change with time, the upper camera (h) which captures the specimen from its upper surface has the function of being capable of taking moving images or still images. When the motion of the specimen is ascertained, it is preferable to take moving images. Preferably, the upper camera (h) is a digital camera capable of taking moving images at high velocity and high density (a time resolution of $1/250$ sec or more, and a spatial resolution of 100 μm or less). For example, the upper camera (h) includes VW-600 by Keyence Corporation. The moving images of the alimentary bolus (specimen) are not only used for visual check but also used to convert the change of a diffusion locus into a diffusion area and thereby quantify the diffusion area of the alimentary bolus (specimen). Specifically, the images of the alimentary bolus (specimen) are digitized by use of an image processing software, and the diffusion area of the specimen during falling or downward flowing is found. The image processing software includes, for example, Image J by National Institutes of Health or Matlab by Mathworks.

Furthermore, the side camera (g) which captures the alimentary bolus (specimen) from its side surface may take either moving images or still images or both of them. When the side camera (g) takes moving images, it is preferable to provide a sensor which captures the passage of the alimentary bolus to synchronize the behavior of the alimentary bolus on the tilted plate and the moving images. When the side camera (g) takes still images, it is preferable to mount a trigger on one of the tilted plates to capture the tip of the alimentary bolus. From the viewpoint of making the device more compact and decreasing the volume of experimental data, the side camera (g) which captures the alimentary bolus (specimen) from its side surface preferably takes still images. The side camera (g) which takes still images includes, for example, CV-3500 by Keyence Corporation. It is possible to digitize the moving images or still images of the alimentary bolus (specimen) by use of an image processing software, and measure the diffusion area of the specimen. The image processing software includes, for example, Image J by National Institutes of Health or Matlab by Mathworks. These images of the alimentary bolus (specimen) are used to measure the thickness and dynamic contact angle or the like of the alimentary bolus (specimen) during its falling or downward flowing.

The upper camera (h) which captures the alimentary bolus (specimen) from its upper surface can move together with the tilted plate. That is, when the angle of the tilted plate is changed, the angle of the camera also changes accordingly. It is preferable that this upper camera (h) is always vertically upwardly mounted on the plane of the tilted plate. The side camera (g) which captures the alimentary bolus (specimen) from its side surface also needs to be always mounted in a direction at right angles with the tilting direction of the tilted plate in response to the angle of the tilted plate. For example, the images of the alimentary bolus (specimen) are digitized by use of an image processing software, and used to measure the diffusion area of the specimen during falling or downward flowing.

The image data or the data converted into a two-dimensional form are automatically or manually transferred to the computer for data analysis.

In the present embodiment, the data logger (i) as the timing recording unit is a software or a system which records, with time, voltage, current, pressure, temperature, strain, acceleration, pulse, and others when the dynamic behavior of the alimentary bolus (specimen) is captured. For example, the data logger includes a multiple input data acquisition system NR-series by Keyence Corporation.

The data logger (i) is a system for automatic or manual transfer to the computer for data analysis.

In the present embodiment, property values of the alimentary bolus (specimen) during downward flowing or falling are the area, the length, the width, the velocity, the angle, the thickness of a contact angle, and the thickness of the center. From the measurement of these property values, shear velocity, wall surface shear stress, wall surface shear force, force on the wall surface (tilted surface), and energy consumed in the wall surface are automatically calculated by the computer. Specifically, the shear velocity is found by dividing an average velocity by the thickness of the center. The wall surface shear stress is found by multiplying viscosity by the average velocity, and then dividing the result by the thickness of the center. The wall surface shear stress is found by multiplying the wall surface shear force by the area. The energy consumed in the wall surface is found by multiplying the wall surface shear force by the average velocity.

Note that the viscosity can be measured by, for example, a rheometer (dynamic viscoelasticity measurement device).

The specimen as a simulative alimentary bolus according to the present embodiment is a food (an intermediate product, an end product, a prepared product of an end product), and also includes drinks. The drinks include, but not exclusively, water, carbonated water, liquor, soft drinks, fruit juice drinks, soup, and others. The food includes, but not exclusively, grain foods, potatoes, nuts and seeds, beans, dairy products, eggs, meat, fish and shellfish, vegetables, fruits, various food additives (e.g. xanthan gum), processed foods produced by blending, dissolving, drying, heating, cooking, fermenting, or mixing the above, and foods and drinks produced by reducing, cooking, or diluting the processed food.

In the present embodiment, the physical properties of food can be used as an estimation method of mouthfeel from the correlation with the sensual mouthfeel of the same food and drinks. Such examples include the correlation between the area transition in the upper part of the tilted plate and the feel of remainder in the mouth, the correlation between the spread width of the alimentary bolus and the feel of sticking in the mouth, the correlation between the pressure at the time of discharge and the degree of smoothness, the correlation between the time from the start of discharge to the upper sensor and the ease of sliding toward the throat, the correlation between force (the viscosity is multiplied by passage time and the result is divided by a sticking area) and ease of drinking, the correlation between power (force is multiplied by velocity) and passing through the throat, the correlation between the expansion velocity before the capture by the upper sensor or the transition of the sticking area before the capture of the alimentary bolus by the upper sensor and the sensation of spread in the mouth, the correlation between the area and time of remaining after the passage of the alimentary bolus and the feel of sticking in the mouth, and the correlation between the transition of the sticking area of the alimentary bolus in a target region and bitability.

The measurement device according to the present embodiment measures the dynamic physical properties of the specimen (alimentary bolus) one or more times. The specimen (alimentary bolus) including a solid matter that falls or the specimen (alimentary bolus) that separates into two or more layers during downward flowing is preferably measured two or more times for improvement in the accuracy of measurement.

In the present description, when the range of numerical values is written as "X to Y", the range of numerical values includes X and Y which are the numerical values at both ends of this range.

EXAMPLES

While examples and experimental examples are shown below to more specifically describe the present invention, the scope of the present invention is not at all limited to the descriptions in these examples and experimental examples.

Example 1

In the present example of measurement shown in FIG. 1, the high-performance piston pump (model 2BC10J23 by HIBAR Corporation) was used as the pump (a) for use in the supply of the specimen, and the controller (model UNIMATIC CP50 by HIBAR Corporation) which pneumatically adjusted the piston was used for the control of the pump. The specimen (water) put in the beaker was self-sucked by the pump (a), and discharged onto the tilted plate through the nozzle.

The minute-differential-pressure pressure sensor (b) (sensor: AP-10S and amplifier: AP-V80 by Keyence Corporation) was disposed between the pump (a) and the nozzle. A discharge time was measured from the comparison of output values of the discharge check laser sensor (c) (sensor: LV-NH42 and amplifier: LV-N11MN by Keyence Corporation) disposed in the vicinity of the tip of the nozzle. The discharge time (discharge flow volume) could be checked by measuring not only the discharge volume of a discharge pump but also its discharge time.

Next, the tip of the nozzle was disposed at a position 25 mm high vertically above the tilted plate having a width of 100 mm and a height of 150 mm (its angle and material could be changed to any angle and material; normally, the angle was 45° to 60°, and silicon or urethane was used as the material.), The specimen (water) downwardly flowed without overflowing the tilted plate.

The upper arrival check sensor (d) (sensor: LV-NH100 and amplifier: LV-N11MN by Keyence Corporation) was disposed at a position 50 mm from the end face of the tilted plate, the middle arrival check sensor (e) (sensor: LV-NH42 and amplifier: LV-N11MN by Keyence Corporation) was disposed 20 mm downstream from the upper sensor, and the lower arrival check sensor (f) (sensor: LV-NH100 and amplifier: LV-N11MN by Keyence Corporation) was further disposed 40 mm downstream from the upper arrival check sensor. Since the distances between the sensors (d), (e), and (f) were known, the timing of the arrival of the alimentary bolus could be detected by the changes of waveforms, and the downward flow velocity and acceleration in each section could be calculated. All the waveforms were stored in the data logger (NR-500 by Keyence Corporation). Further, the sensors (d) and (f) were transmission type sensors disposed on the side surface of the tilted plate, whereas the sensor (e) (CV-3500 by Keyence Corporation) was a reflection type sensor disposed obliquely above the tilted plate. The sensor (e) doubled as the trigger of the side camera (g) (CV-3500 by Keyence Corporation) disposed on the side surface. This side camera (g) photographed the shape of the alimentary bolus during downward flowing from its side surface, measured the angle of the tip of the alimentary bolus, and could thereby calculate the macroscale dynamic contact angle.

Furthermore, the high-velocity and high-precision camera (VW-600 by Keyence Corporation) as the upper camera (h) was disposed above the tilted plate always at an angle of 90° to the tilted plate, and the whole downward flow phenomenon (e.g. the change of shape with time and the arrival time) was measured. The trigger of this camera (h) for moving images was the sensor (d), and an image processing device took an image 100 msec before the triggering by the sensor (d). That is, the moment at which the specimen was discharged from the nozzle and reached the tilted plate could also be recorded by the high-velocity camera (h). These images were digitized by use of the image processing software (Image J by National Institutes of Health or Matlab by Mathworks), and the diffusion area during downward flowing was computed. Output values from all the sensors and image data were automatically loaded onto the computer for data analysis.

Example 1

In the measurement device shown in FIG. 1, the precision (amount and time) of the most upstream supply part of liquid was directly related to the precision of measurement data. Thus, the precision of a supply device was checked.

The high-performance piston pump (model 2BC10J23 by HIBAR Corporation) was used as the pump (a) used for supply. The controller (model UNIMATIC CP50 by HIBAR Corporation) which pneumatically adjusted the piston velocity was used for the control of the pump (a).

The nozzle was mounted on the pump (a), a predetermined amount (5 mL) of water and thickness adjustment food (2 wt % Toromake (registered trademark) SP by Meiji Corporation) was discharged more than one time (N=10), and then the validity and precision of the discharge amount were checked. It was evaluated valid if an average value was 5±0.5 (g). If a relative error (hereinafter, an error) was less than 10%, the precision of the measurement was evaluated high.

Results of the measurement value, average value, standard deviation, and error of the discharge amount of each specimen are shown in Table 1. For water, the average value was 5.05 (g), the standard deviation was 0.058 (g), and the error was 1.1%. For the thickness adjustment food, the average value was 5.00 (g), the standard deviation was 0.081 (g), and the error was 1.6%, The discharge amount of each specimen was valid, and high in precision. Therefore, it could be said that in the device according to the present embodiment, a supply system of the alimentary bolus (specimen) was capable of valid and high-precision discharge (supply) regardless of the level of the viscosity of the alimentary bolus (specimen).

TABLE 1

Discharge Amounts of Specimens and Repetition Error

| | | Specimen | |
| --- | --- | --- | --- |
| | Unit | Water (n = 10) | Thickness adjustment food (2 wt % Toromake SP) (n = 10) |
| Average value | [g] | 5.046 | 4.996 |
| Standard deviation | [g] | 0.058 | 0.081 |
| Error | [%] | 1.149 | 1.616 |

Example 2

Figure 2:
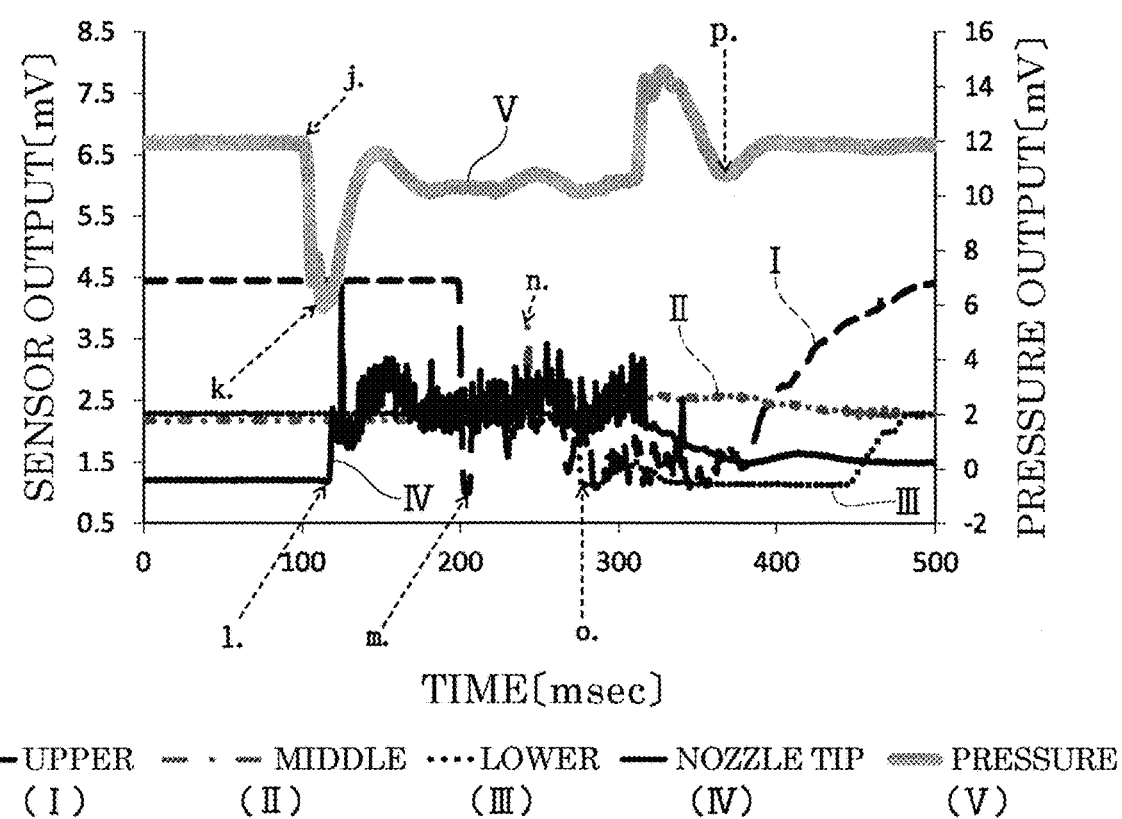
FIG. 2 shows examples of measurement data (an upper arrival sensor, a middle arrival sensor, a lower arrival sensor, a nozzle tip sensor, and a pressure value)

In the measurement device shown in FIG. 1, the validity and precision of various measurement values at the time of the supply of the specimen to the tilted plate were checked. Typical measurement waveforms obtained from the present measurement device are shown in FIG. 2. The horizontal axis in the graph of FIG. 2 represents time, the left vertical axis represents outputs from the respective sensors (c), (d), (e), and (f), and the right vertical axis represents the output from the pressure sensor (b). A broken line I in the graph represents the output from the upper sensor (d), a chain line II represents the output from the middle sensor (e), a dotted line III represents the output from the lower sensor (f), and a curve line IV represents the output from the discharge check sensor (c) at the tip of the nozzle. Further, a curve line V in the graph represents the output from the pressure sensor (b) of the nozzle. The timing at which the output waveform of each sensor greatly changes represents the arrival time of the alimentary bolus. The precision of the velocity and discharge amount of the alimentary bolus (specimen) was checked, and the validity of the velocity of the alimentary bolus (specimen) was examined.

The following were measured by use of the device in Example 1; pressure decrease time (j) at the time of the supply of the specimen to the tilted plate, discharge negative pressure time (k), nozzle arrival time (l), time of arrival at the upper sensor (which may be abbreviated as upper arrival time) (m), time of arrival at the middle sensor (which may be abbreviated as middle arrival time) (n), time of arrival at the lower sensor (which may be abbreviated as lower arrival time) (o), and discharge end time (p). From the measurement results, velocity from the upper sensor to the middle sensor (which may be abbreviated as upper-middle velocity), velocity from the middle sensor to the lower sensor (which may be abbreviated as middle-lower velocity), and velocity from the upper sensor to the lower sensor (which may be abbreviated as upper-lower velocity) were computed, and the precision of the discharge time was checked. A schematic diagram of typical measured waveforms obtained from the example is shown in FIG. 2. The timing at which the output waveform of each sensor greatly changes can be judged to be the time of the arrival of the alimentary bolus.

Water and a thickness adjustment food (2 wt % Toromake (registered trademark) SP by Meiji Corporation) were used as specimens repeated times: N=5. The arrival time of the alimentary bolus (specimen) in each sensor was measured, and the average velocity (velocity) of the alimentary bolus was computed. The precision of the upper-middle velocity, the middle-lower velocity, and the upper-lower velocity was determined to be satisfactory if the error was less than 10%.

As a result, each of the errors in the upper-middle velocity, the middle-lower velocity, and the upper-lower velocity of water or the thickness adjustment food was less than 5%. Each of the errors in the upper-lower velocity was less than 2%. It can be said that the precision of the velocities at the time of discharge is high. Each of the errors in the discharge time of water or the thickness adjustment food was less than 2%. That is, it can be said that regarding the precision of specimen supply in the device according to the present invention, repetition precision is high in terms of the supply amount, supply time, and supply flow volume.

By the way, it is reported that a swallow by a healthy adult is about 5 ml, and that the velocity of swallowing is 1.7±0.7 m/s. In the result according to the example, the average of the upper-lower velocity during the downward flow of 5 ml of water was 1.49 seconds. That is, the velocity of the actual swallowing is equal in value to the velocity measured by the device according to the present invention, and it can be said that the example is valid as false swallowing in terms of the supply amount and velocity.

TABLE 2

Measurement Data Regarding Specimens

| | Unit | Average value | Standard deviation | Error (%) |
|---|---|---|---|---|
| Water | | | | |
| j. Pressure decrease | s | 0.00584 | $8.94 \times 10^{-5}$ | 1.53 |
| k. Discharge negative pressure | mA | 6.311 | 0.04365 | 0.69 |
| l. Nozzle arrival | s | 0.0155 | 0.00264 | 17.0 |
| m. Upper arrival | s | 0.07388 | 0.00389 | 5.27 |
| n. Middle arrival | s | 0.08736 | 0.00327 | 3.74 |
| o. Lower arrival | s | 0.10068 | 0.00355 | 3.53 |
| p. Discharge end | s | 0.20752 | 0.00050 | 0.22 |
| Nozzle-upper arrival time (m − 1) * 1000 | msec | 57 | 2.94 | 5.11 |
| Velocity Upper-middle 0.02/(n − m) | m/s | 1.487 | 0.073 | 4.91 |
| Velocity Middle-lower 0.02/(o − n) | m/s | 1.503 | 0.06 | 3.97 |
| Velocity Upper-lower 0.04/(o − m) | m/s | 1.493 | 0.022 | 1.51 |
| Discharge time (p − 1) * 1000 | msec | 192 | 2.51 | 1.30 |
| Thickness adjustment food (2 wt % Toromake SP) | | | | |
| j. Pressure decrease | s | 0.00544 | 0.00017 | 3.08 |
| k. Discharge negative pressure | mA | 4.866 | 0.06640 | 1.36 |
| l. Nozzle arrival | s | 0.0156 | 0.00032 | 2.03 |
| m. Upper arrival | s | 0.09764 | 0.00036 | 0.37 |
| n. Middle arrival | s | 0.13308 | 0.00036 | 0.27 |
| o. Lower arrival | s | 0.1732 | 0.00118 | 0.68 |
| p. Discharge end | s | 0.21112 | 0.00060 | 0.27 |
| Nozzle-upper arrival time (m − 1) * 1000 | msec | 82 | 0.43 | 0.53 |
| Velocity Upper-middle 0.02/(n − m) | m/s | 0.564 | 0.008 | 1.33 |
| Velocity Middle-lower 0.02/(o − n) | m/s | 0.499 | 0.016 | 3.23 |
| Velocity Upper-lower 0.04/(o − m) | m/s | 0.529 | 0.008 | 1.53 |
| Discharge time (p − 1) * 1000 | msec | 196 | 0.61 | 0.31 |

Example 3

In the measurement device shown in FIG. 1, the reproducibility of the shape of the tip of the alimentary bolus and the precision of measurement timing were checked.

Figure 3:
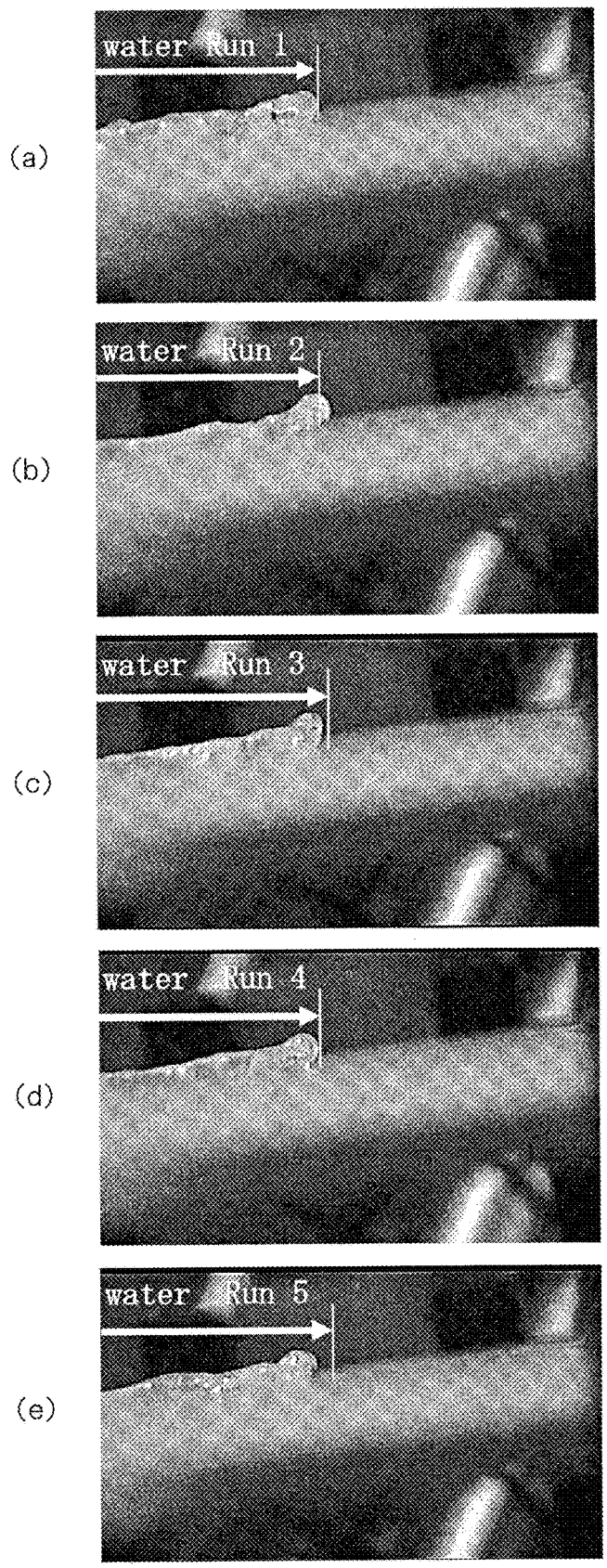
FIG. 3(a) to FIG. 3(e) show side images that show the tip shapes of a water alimentary bolus during downward flowing on a tilted plate.
Figure 4:
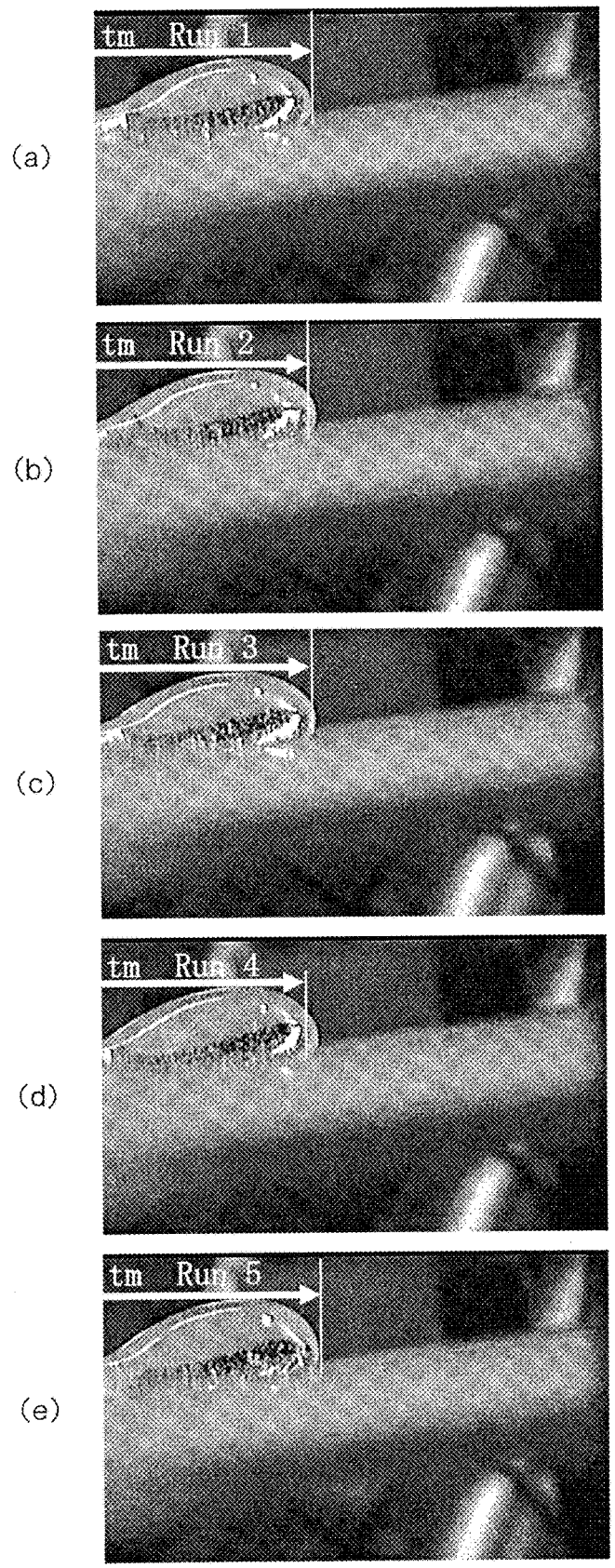
FIG. 4(a) to FIG. 4(e) show side images that show the tip shapes of an alimentary bolus of thickness adjustment food during downward flowing on the tilted plate.

The device in Example 1 was used. The camera (CV-3500 by Keyence Corporation) to take still images for the measurement of the shape of the alimentary bolus during downward flowing and the contact angle was disposed on the side surface of the tilted plate. Regarding the timing of the trigger to take still images, the precision of repetitive photography (timing) and the shape of the tip of the alimentary bolus were qualitatively weighed. As in Example 2, water and the thickness adjustment food (2 wt % Toromake (registered trademark) SP by Meiji Corporation) were used as specimens, and photography was performed repeated times: N=5. The photographed shapes of the tips of the alimentary boluses are shown in FIG. 3 and FIG. 4. The length of the alimentary bolus indicated the length from the tip of the food to its tail end in the still images.

As shown in FIG. 3, it can be seen that because the water alimentary bolus during downward flowing has a form that is small at the tip, the alimentary bolus is widely diffused in a plate-like shape as a whole. White arrows (Run1 to Run5) in FIG. 3(a) to FIG. 3(e) had about the same length (the distances from the left end face to the tips of the arrows). That is, it can be seen that during five repetitive photography operations, the tip of the alimentary bolus can be detected at about the same timing, Although it has heretofore been quite difficult to detect the tip of widely diffused water because of a large number of its droplets, suitable adjustments of the kind of sensor and its sensitivity and position enable photography that is high in repetition accuracy. Therefore, it can be said that the tip of the alimentary bolus can be detected with a high degree of precision.

As shown in FIG. 4, it could be observed that the shape of the tip of the thickness adjustment food during downward flowing was round and the thickness adjustment food was downwardly flowing in a lump. The tip of the bolus of the specimen (0.2 wt % thickness adjustment food) was elliptic, and had a shape thicker than that of water. The lengths (white arrows (Run1 to Run5) in FIG. 4(a) to FIG. 4(e)) of the boluses of the thickness adjustment food were about the same (the distances from the end face to the tips of the arrows). That is, it can be seen that during five repetitive photography operations, the present measurement system can detect the tip of the alimentary bolus at about the same timing. Therefore, it can be said that the present measurement system can precisely detect the tip of the alimentary bolus regardless of the level of viscosity.

Example 4

In the measurement device shown in FIG. 1, the high-velocity and high-precision camera (g) (for moving images, VW-600 by Keyence Corporation) disposed to be always located vertically to the tilting direction of the tilted plate can capture, with time, the change of the shape of the alimentary bolus during downward flowing.

Furthermore, the present measurement system makes it possible to not only visually check the change of the diffusion locus but also convert it into a diffusion area which is acquired in a numerical form, To verify this, the precision of the diffusion area of the alimentary bolus (specimen) was checked.

Figure 5:
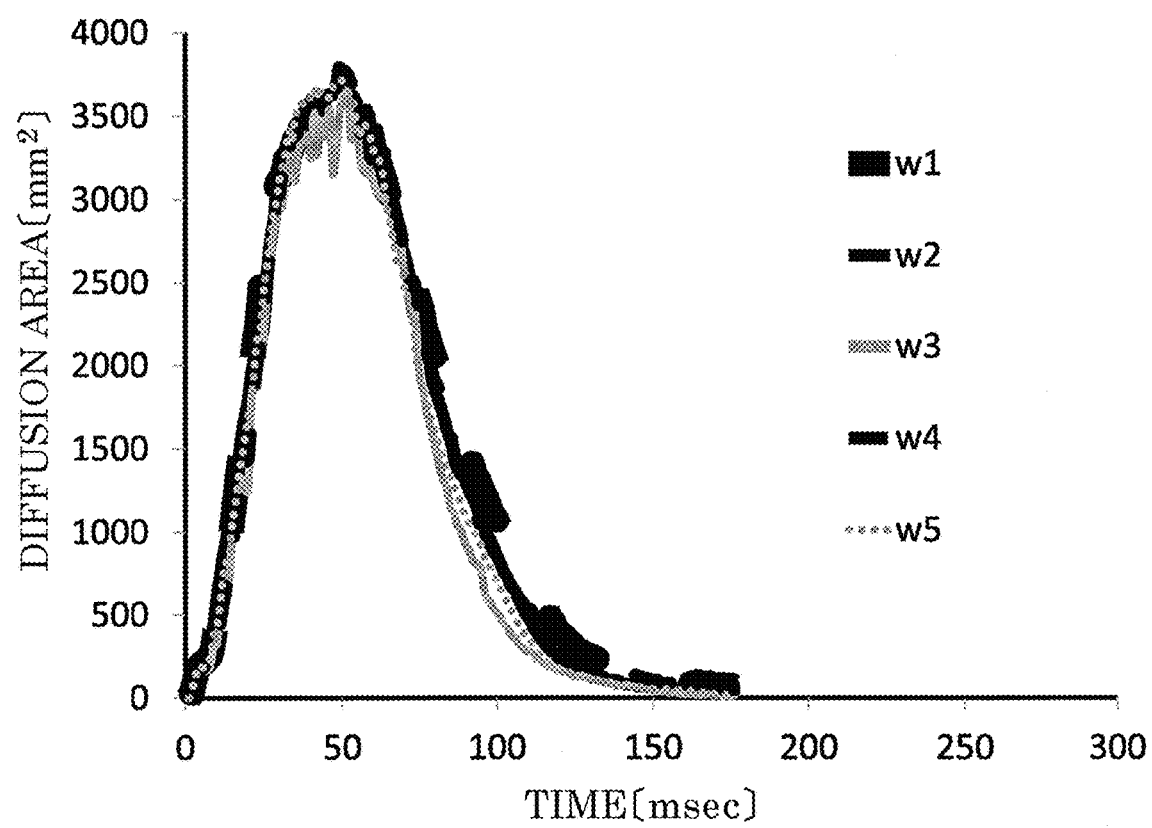
FIG. 5 shows the change of the diffusion area of an alimentary bolus (water) with time.

By use of the device in Example 1, moving images of the alimentary bolus (specimen) were taken with the upper camera (h) when the specimen was supplied to the tilted plate. As in Example 2, water and the thickness adjustment food (2 wt % Toromake (registered trademark) SP by Meiji Corporation) were used as specimens. Each of the specimens was discharged by 5 ml, and photography was performed repeated times: N=5. The moving images of the alimentary bolus (specimen) were digitized by image J. The procedure of digitization was as follows: First, the file of the taken moving images was opened, and the images were complemented by an angular correction and the extraction of a target region. Then the alimentary bolus in the processed image and an image (32 bits) resulting from the stack decomposition of the former image (32 bits) was converted into black, and the contrast and others thereof were adjusted. After this, the length of the alimentary bolus was set by Set Scale, and the diffusion area was measured by a method of particle analysis. The change of the diffusion area with time when the alimentary bolus (water) downwardly flows on the tilted plate is shown in FIG. 5. Moreover, the change of the diffusion area with time when the alimentary bolus (thickness adjustment food) downwardly flows on the tilted plate is shown in FIG. 6.

As shown in FIG. 5 (w1 to w5), there were almost no changes in the diffusion area in the early stage of the downward flow and the tendency of the increase of the area in five repetitions. Moreover, the value of the maximum diffusion area indicated about the same value in the repetitive experiments.

Figure 6:
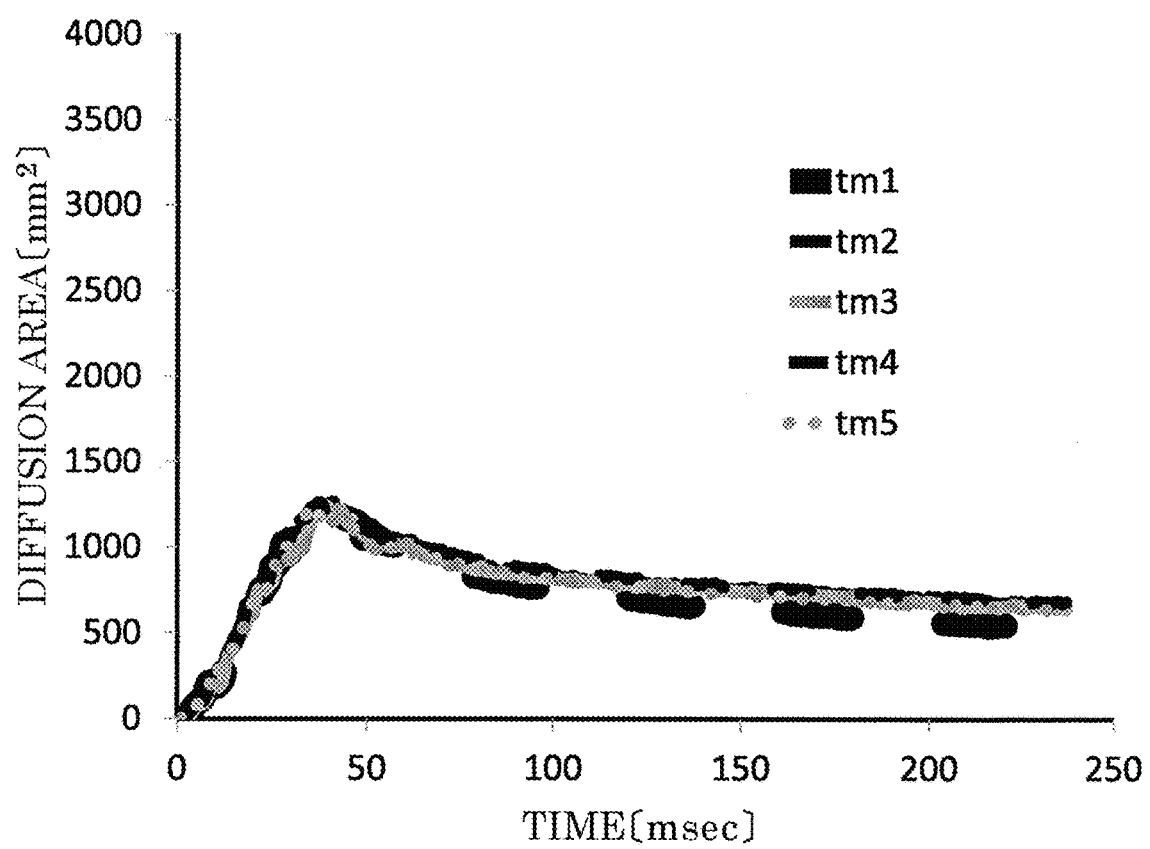
FIG. 6 shows the change of the diffusion area of an alimentary bolus (thickness adjustment food) with time.

As shown in FIG. 6 (tm1 to tm5), the diffusion area in the early stage of the downward flow and the tendency of the increase of the area were the same in five repetitions. Moreover, the value of the maximum diffusion area indicated about the same value in the repetitive experiments.

That is, it can be said that the present measurement device is high in the precision of measurement in terms of the extremely high repetition accuracy regarding the maximum diffusion area and the time to reach the maximum diffusion area in both the specimens different in viscosity.

Example 5

In the measurement device shown in FIG. 1, the precision and validity of the dynamic properties (properties of downward flow such as the downward flow velocity, the shape of the tip of the alimentary bolus, and the diffusion area) of the thickness adjusters different in concentration were checked.

Figure 7:
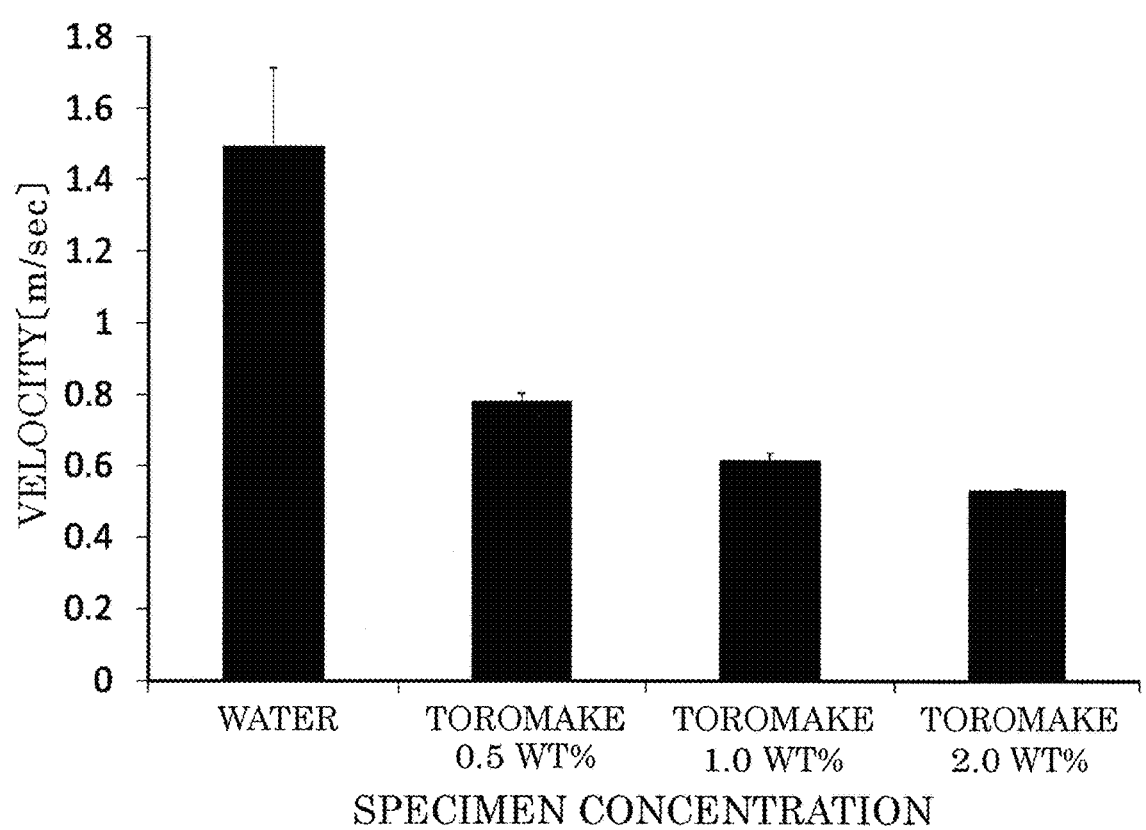
FIG. 7 shows a comparison of the downward flow velocities of specimens different in concentration.

The device in Example 1 was used. Specimens were water and the thickness adjusters (Toromake (registered trademark) SP by Meiji Corporation) which were adjusted to 0.5 wt %, 1.0 wt %, and 2.0 wt %, respectively. The number of repetitions was N=5, the velocities of the specimens between the sensors and the discharge times of the specimens were measured, and the average values, the standard deviations, and the errors were put on Table 3. If the errors of the dynamic properties in five measurements were less than 10%, the precision was judged to be high. The specimens (alimentary boluses) of all the concentrations had errors of less than 10%, Moreover, the upper-lower velocity is shown in FIG. 7, The shapes of the boluses of the specimens in the side surface during downward flowing are shown in FIG. 8(a) to FIG. 8(d), respectively. Further, the diffusion areas of the boluses of the specimens during downward flowing with time are shown in FIG. 9(a) to FIG. 9(d) region by region (the whole part, upper part, middle part, and lower part), respectively.

As shown in Table 3, the error of the velocity between the upper and lower sensors, and the error of the discharge time were both less than 7% in water, the 0.5 wt % thickness adjustment food, the 1.0 wt % thickness adjustment food, and the 2.0 wt % thickness adjustment food. Therefore, it can be said that the device according to the present invention can precisely measure the velocity of the alimentary bolus.

As shown in FIG. 7, there was a considerable difference of downward flow velocity between water and the thickness adjustment foods, and the downward flow velocity of the 0.5 wt % thickness adjustment food was about half the downward flow velocity of water. Moreover, there was a decrease in the downward flow velocity in response to the increase of the concentration (viscosity) of the thickness adjustment food. In other words, there is no contradiction between the actual phenomenon in which the downward flow velocity decreases in response to the increase of viscosity, and the measurement values and computation values of physical properties by the device according to the present invention. That is, it can be said that the dynamic properties of the alimentary bolus measured by the device according to the present invention are valid.

Figure 8:
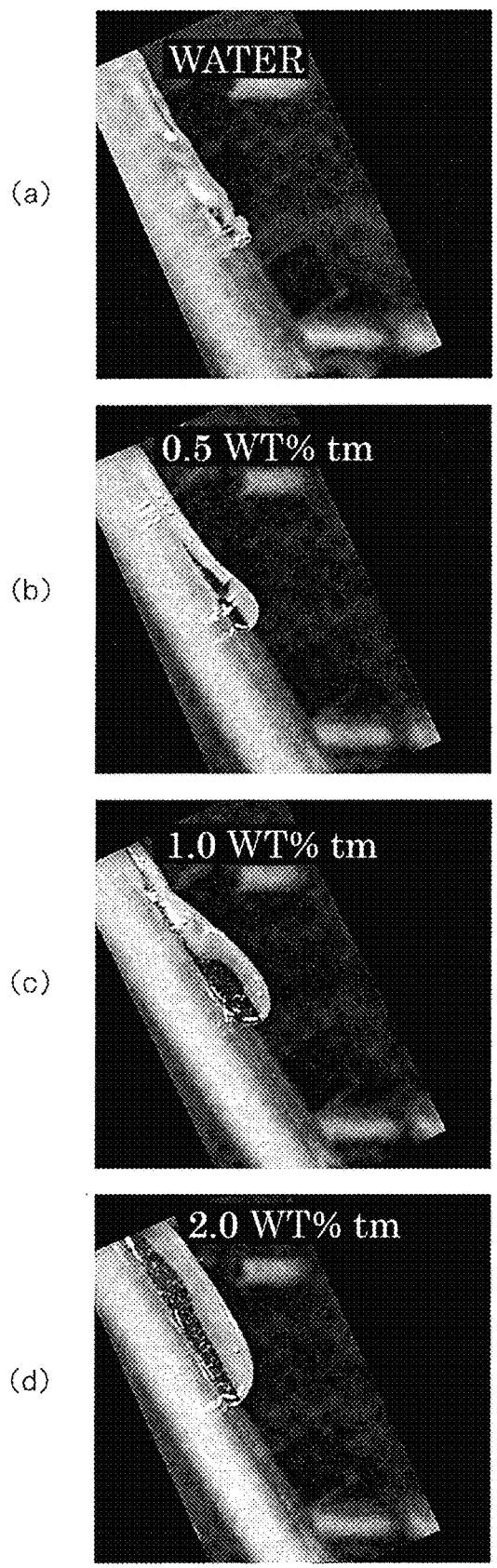
FIG. 8(a) to FIG. 8(d) show the downward flow shapes of the specimens different in concentration.
Figure 9:
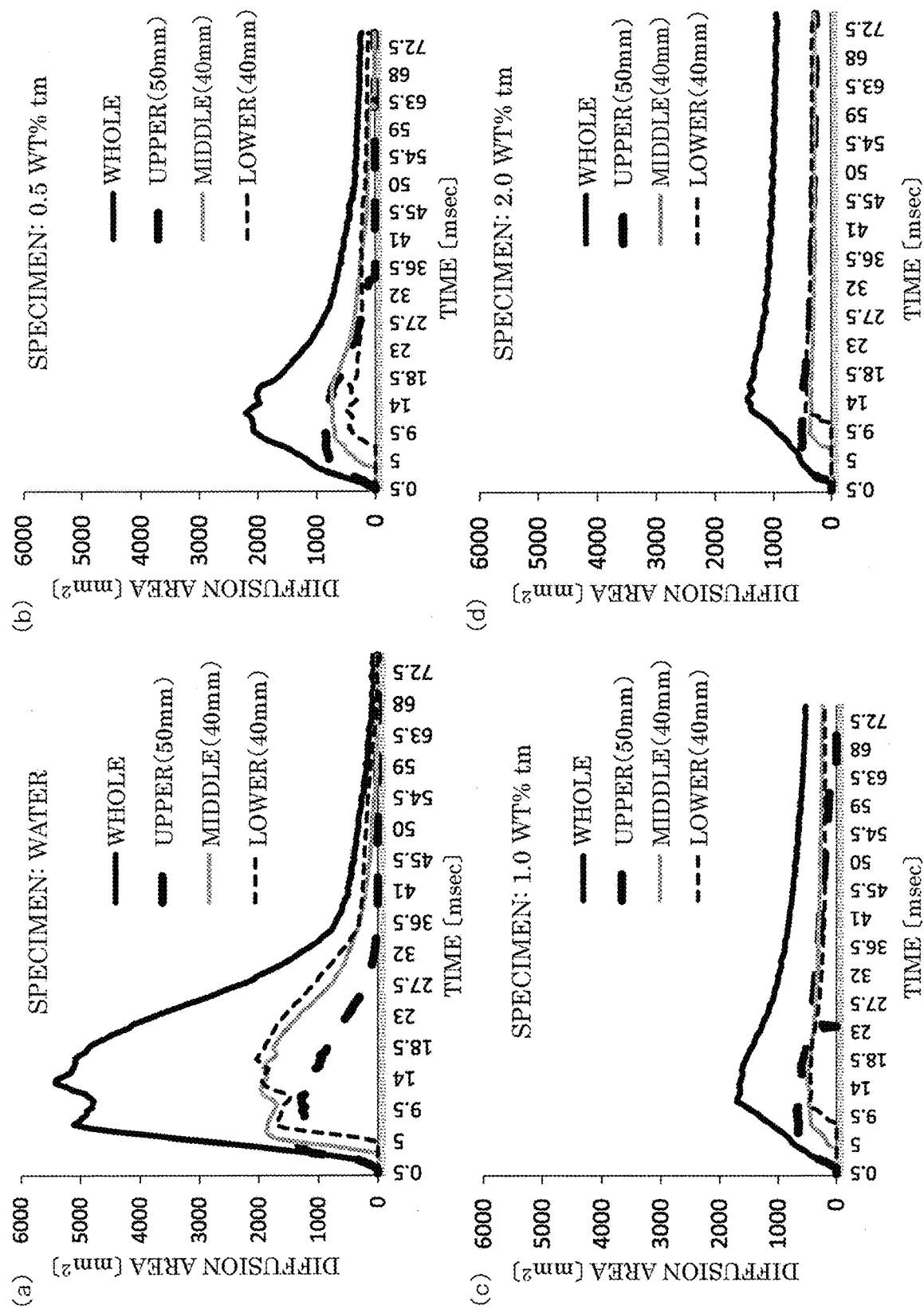
FIG. 9(a) to FIG. 9(d) show a comparison of the diffusion areas of the specimens different in concentration during downward flowing.

As shown in FIG. 8, it was observed that the water alimentary bolus had a tip that was small in thickness, and was widely diffused on the tilted plate. Moreover, it could be confirmed that the tip of the alimentary bolus (specimen) was greater in thickness when the concentration of the thickness adjustment food was higher, and the same thickness remains from the tip of the downwardly flowing alimentary bolus toward its back side.

As shown in FIG. 9(a) to FIG. 9(d), the diffusion area of water was larger than those of any other materials on the whole tilted plate, in the upper part, in the middle part, and in the lower part. Moreover, when the thickness adjustment foods were compared with each other, the thickness adjustment food of higher concentration had a smaller diffusion area, and had a smaller difference between the maximum diffusion area and the diffusion area at the end of observation. The relation between the concentration and diffusion area of the thickness adjustment food was similar to the relation between the concentration of the thickness adjustment food and the shape of the tip of the alimentary bolus. These tendencies were also confirmed from the shape of the tip of the downwardly flowing alimentary bolus in FIG. 8(a) to FIG. 8(d), and it was thus proved that the results obtained by the present measurement system were data by different measurement methods but were correlated.

As above, the present device (system) is capable of precisely measuring different downward flow properties of samples different in concentration in terms of the velocity, the shape of the tip of the alimentary bolus, and the diffusion area, and explaining an actually occurring phenomenon without contradiction. It can therefore be said that the behavior of the actual specimen (alimentary bolus) is validly evaluated.

TABLE 3

Downward flow properties of thickness foods (specimens) of different concentrations

|  |  | j. Pressure decrease [s] | k. Discharge negative pressure [mA] | l. Nozzle arrival [s] | m. Upper arrival [s] |
| --- | --- | --- | --- | --- | --- |
| Water | Average value | 0.00584 | 6.311 | 0.01550 | 0.07388 |
|  | Standard deviation | 0.00009 | 0.044 | 0.00264 | 0.00389 |
|  | Error | 1.53 | 0.690 | 17.00 | 5.27 |
| Toromake (0.5 wt %) | Average value | 0.00660 | 7.281 | 0.00880 | 0.06754 |
|  | Standard deviation | 0.00024 | 0.160 | 0.00081 | 0.00305 |
|  | Error | 3.71 | 2.200 | 9.23 | 4.51 |
| Toromake | Average | 0.00656 | 7.338 | 0.01260 | 0.08244 |

TABLE 3-continued

Downward flow properties of thickness foods (specimens) of different concentrations

| | | | | | |
|---|---|---|---|---|---|
| (1.0 wt %) | value | | | | |
| | Standard deviation | 0.00026 | 0.108 | 0.00024 | 0.00038 |
| | Error | 3.98 | 1.470 | 1.94 | 0.47 |
| Toromake (2.0 wt %) | Average value | 0.00544 | 4.866 | 0.01560 | 0.09764 |
| | Standard deviation | 0.00017 | 0.066 | 0.00032 | 0.00036 |
| | Error | 3.08 | 1.360 | 2.03 | 0.37 |

| | | n. Middle arrival [s] | o. Lower arrival [s] | p. Discharge end [s] | Nozzle-upper arrival time (m − 1) * 1000 [msec] |
|---|---|---|---|---|---|
| Water | Average value | 0.08736 | 0.10068 | 0.20752 | 57 |
| | Standard deviation | 0.00327 | 0.00355 | 0.00050 | 2.93500 |
| | Error | 3.74 | 3.53 | 0.22 | 5.11 |
| Toromake (0.5 wt %) | Average value | 0.08928 | 0.11876 | 0.21064 | 59 |
| | Standard deviation | 0.00200 | 0.00177 | 0.00150 | 3.60400 |
| | Error | 2.24 | 1.49 | 0.69 | 6.14 |
| Toromake (1.0 wt %) | Average value | 0.11984 | 0.14768 | 0.21048 | 70 |
| | Standard deviation | 0.00101 | 0.00239 | 0.00070 | 0.38500 |
| | Error | 0.85 | 1.62 | 0.33 | 0.55 |
| Toromake (2.0 wt %) | Average value | 0.13308 | 0.17320 | 0.21112 | 82 |
| | Standard Deviation | 0.00036 | 0.00118 | 0.00060 | 0.43400 |
| | Error | 0.27 | 0.68 | 0.27 | 0.53 |

| | | Velocity | | | |
|---|---|---|---|---|---|
| | | Velocity Upper-middle 0.02/(n − m) [m/s] | Middle-lower 0.02 (o − n) [m/s] | Upper-lower 0.04/ (o − m) [m/s] | Discharge time (p − 1) * 1000 [msec] |
| Water | Average value | 1.48700 | 1.50300 | 1.49300 | 192 |
| | Standard deviation | 0.07300 | 0.06000 | 0.02200 | 2.50500 |
| | Error | 4.91 | 3.97 | 1.51 | 1.30 |
| Toromake (0.5 wt %) | Average value | 0.92200 | 0.68000 | 0.782 | 202 |
| | Standard deviation | 0.05200 | 0.03200 | 0.03500 | 1.195 |
| | Error | 5.62 | 4.68 | 4.46 | 0.59 |
| Toromake (1.0 wt %) | Average value | 0.53500 | 0.72100 | 1 | 198 |
| | Standard deviation | 0.01200 | 0.04500 | 0.02100 | 0.502 |
| | Error | 2.15 | 6.20 | 3.36 | 0.25 |
| Toromake (2.0 wt %) | Average value | 0.56400 | 0.49900 | 1 | 196 |
| | Standard Deviation | 0.00800 | 0.01600 | 0.00800 | 0.61 |
| | Error | 1.33 | 3.23 | 1.53 | 0.31 |

Example 6

The downward flow properties of various thickeners were checked by the measurement device shown in FIG. 1.

Four kinds of thickeners (Xanthan Gum: XG, Succinoglycan: SG, Guar Gum: GG, Cellulose: CMC by Danisco Japan Ltd.) were used as specimens. The concentrations of the thickeners are shown in Table 4. The concentrations of these specimens were adjusted so that their viscosities at 100 [Vs] are about the same (a low thickness is about 60 mPa·s, and a high thickness is about 250 mPa·s). 5 ml of each of the specimens was discharged five times, the dynamic physical properties of the photographed alimentary boluses (specimens) were then computed, and the shapes (the dynamic contact angle (contact angle), the diffusion area, and the size of the downward flow locus) were measured. For the measurement of the contact angle, Contact angle plug-in for a general-purpose image processing software Image J (NIH) was used. For the maximum length of the downward flow locus, the longest side was measured in a direction parallel to the downward flow direction. For the maximum width, the greatest length in a short-side direction was measured in a direction orthogonal to the downward flow direction.

TABLE 4

| | Specimens (Thickeners and Concentration of Thickness) | |
|---|---|---|
| Specimen name | Low thickness concentration (wt %) | High thickness concentration (wt %) |
| Xanthan Gum: XG | 0.5 | 1.5 |
| Succinoglycan: SG | 0.4 | 1.2 |
| Guar Gum: GG | 0.4 | 0.75 |
| Cellulose: CMC | 0.25 | 0.7 |

Figure 10:
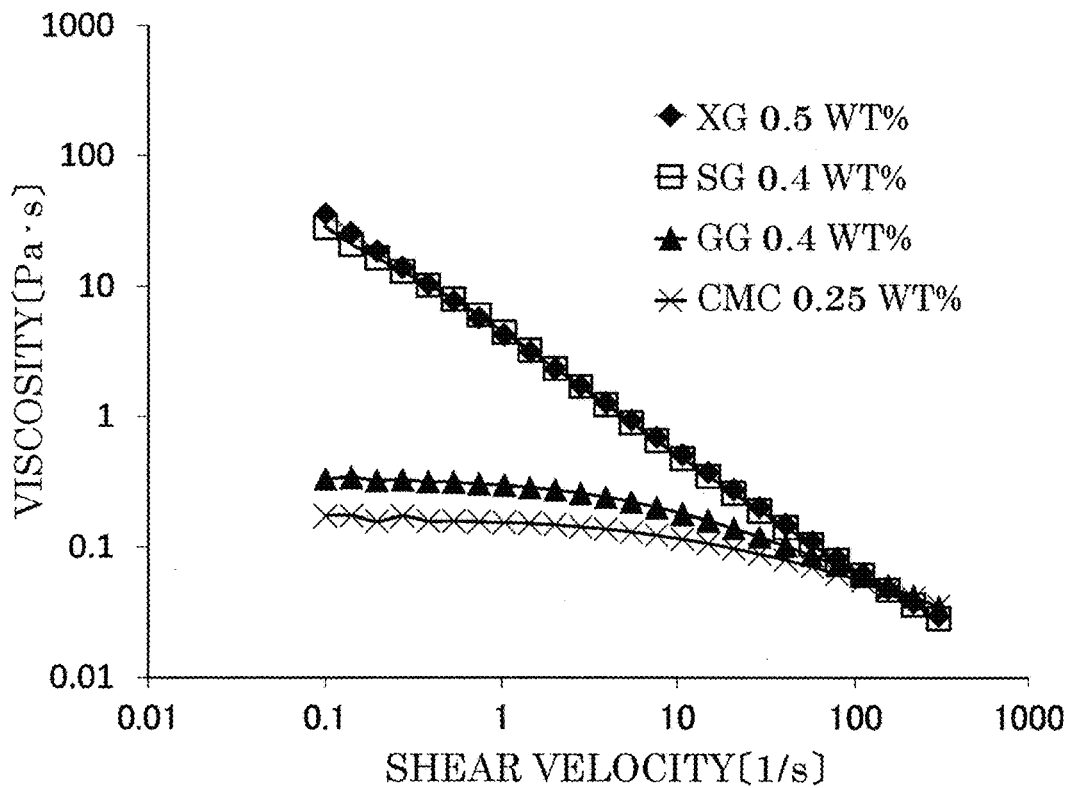
FIG. 10 shows flow curves of low thickness.
Figure 11:
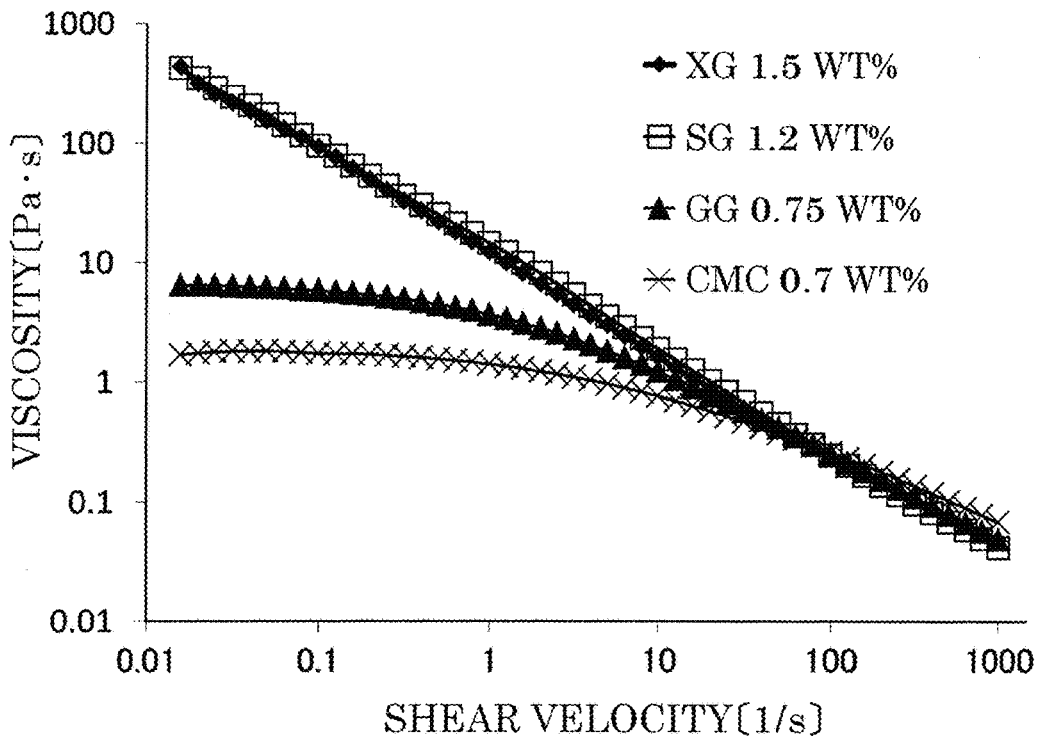
FIG. 11 shows flow curves of high thickness.
Figure 12:
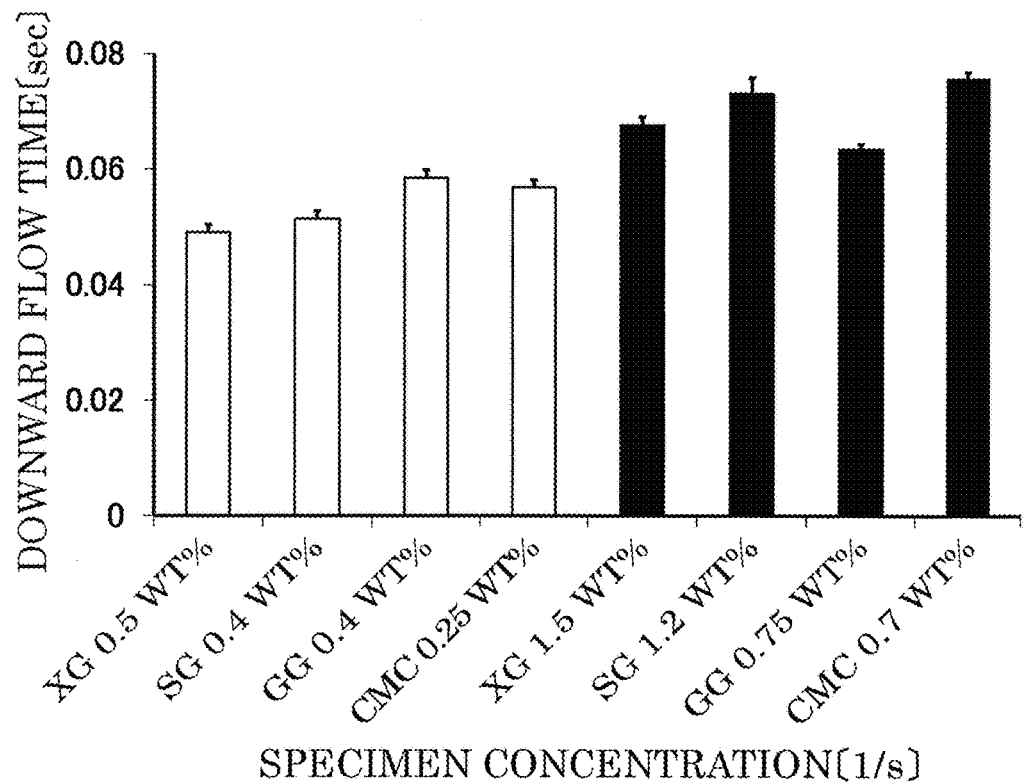
FIG. 12 shows downward flow times in different kinds of thickness adjustment foods and concentrations.
Figure 13:
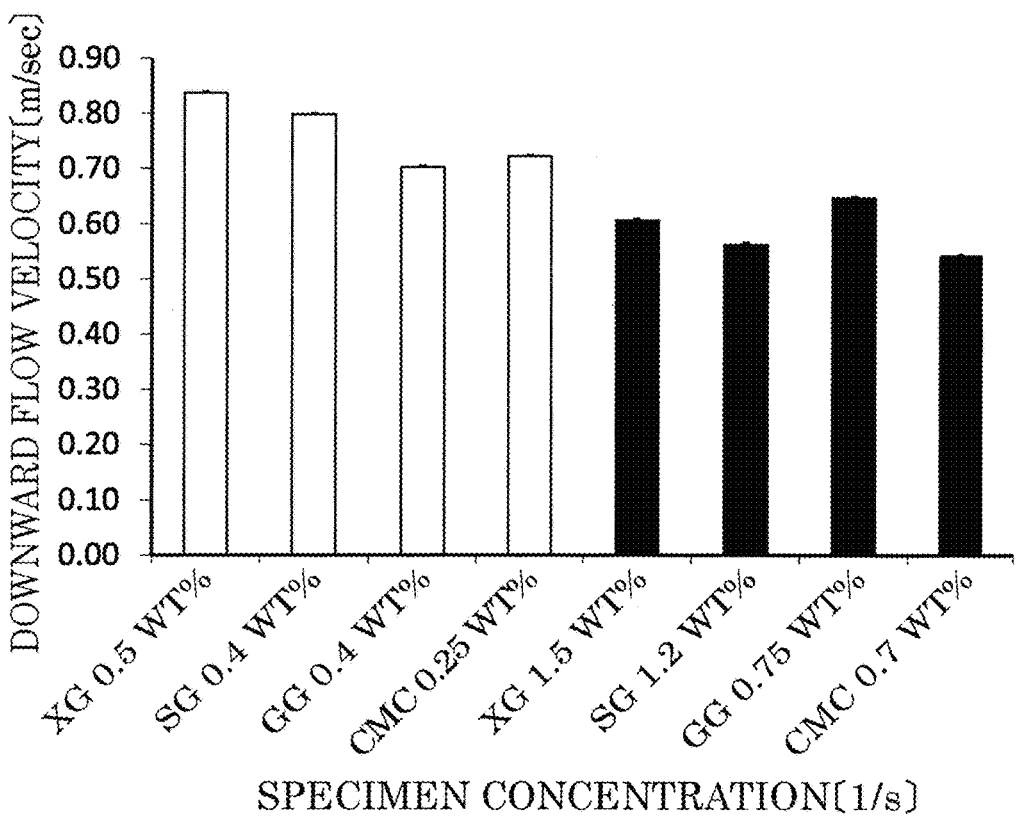
FIG. 13 shows downward flow velocities in different kinds of thickness adjustment foods and concentrations.
Figure 14:
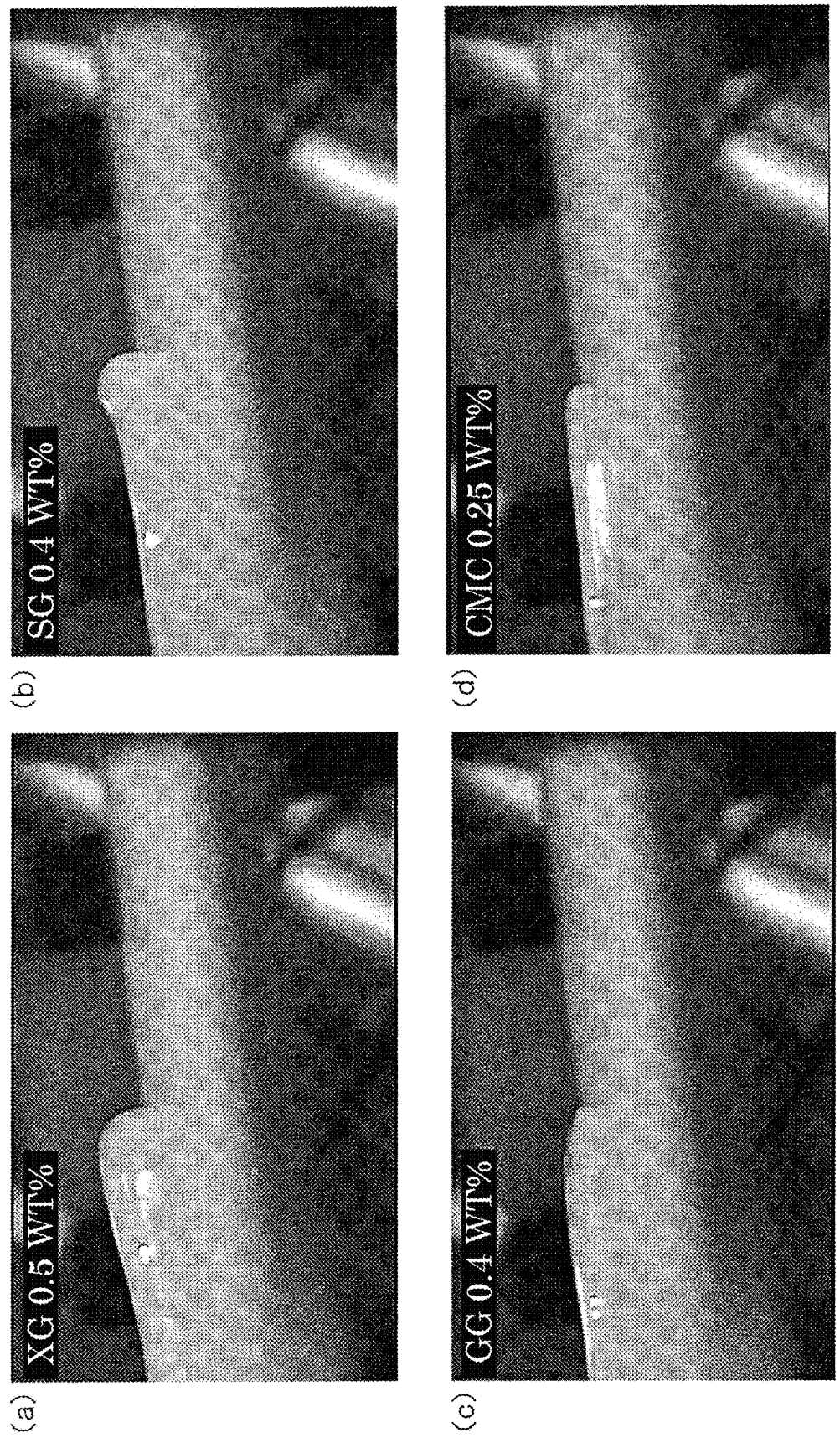
FIG. 14(a) to FIG. 14(d) show side images that show the tip shapes of an alimentary bolus (low thickness) during downward flowing.
Figure 15:
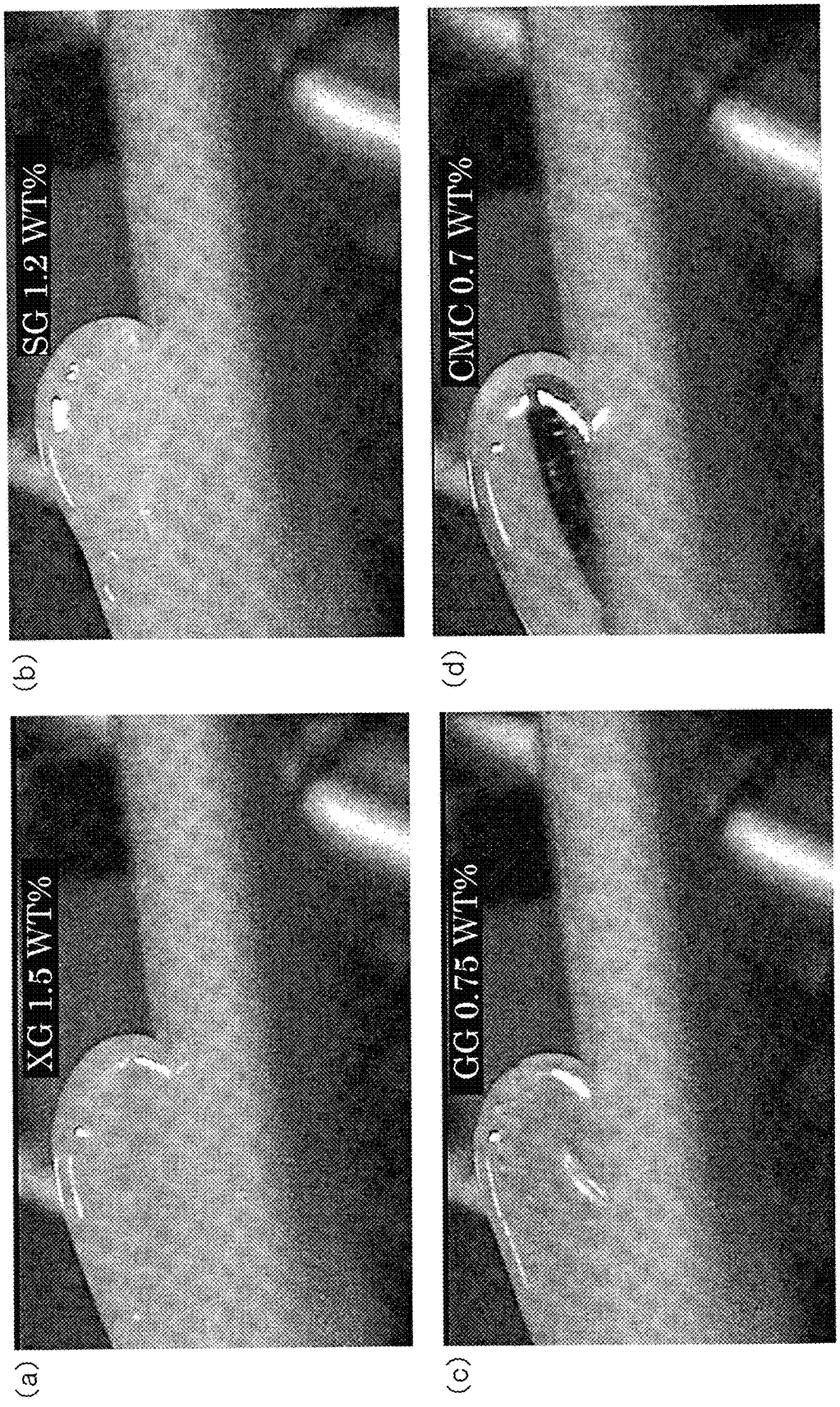
FIG. 15(a) to FIG. 15(d) show side images that show the tip shapes of an alimentary bolus (high thickness) during downward flowing.
Figure 16:
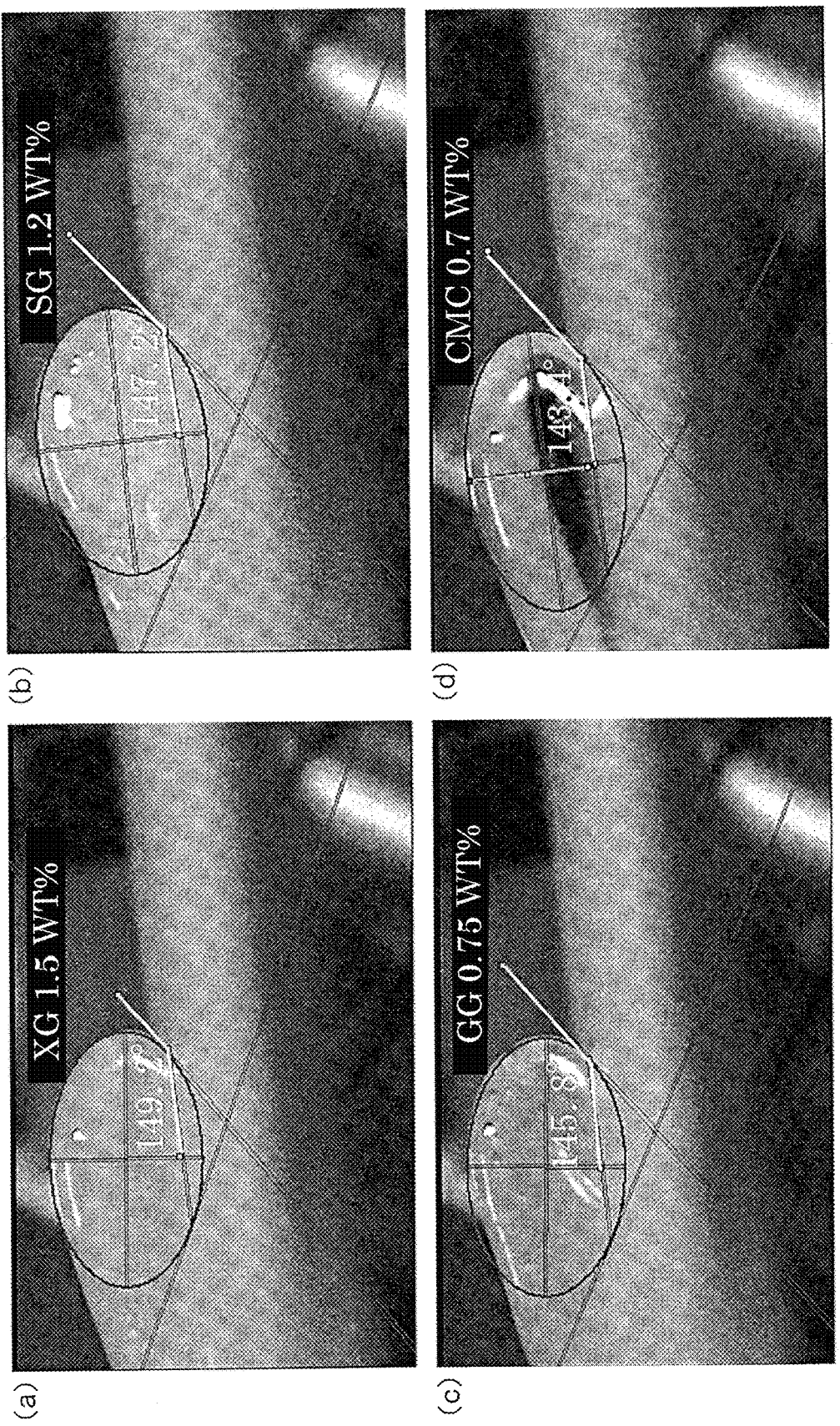
FIG. 16(a) to FIG. 16(d) show side images of the microscale dynamic contact angles of different kinds of specimens during downward flowing on the tilted plate.

Flow curves (shear velocity-viscosity curves) of each of the low-thickness and high-thickness specimens are shown in FIG. 10 and FIG. 11. The downward flow times and downward flow velocities of the alimentary boluses (specimens) are shown in FIG. 12 and FIG. 13.

For the low thickness, the downward flow time and the downward flow velocity varied from specimen to specimen even if each of the specimens had a constant shear velocity and constant viscosity as described above. For the high thickness as well as for the low thickness, the downward flow time and the downward flow velocity varied from specimen to specimen, Even in the case of the specimens adjusted to a predetermined shear velocity and predetermined viscosity, the alimentary bolus (specimen) of each of the thickeners downwardly flowed at a different shear velocity. That is, it is proved that each of the thickeners downwardly flows with its specific properties.

Furthermore, the shapes of the tips of the alimentary boluses (specimens) from the side are shown in FIG. 14(a) to FIG. 14(d) and FIG. 15(a) to FIG. 15(d). As shown in FIG. 14(a) to FIG. 14(d), regarding the shapes of the tips of the low-thickness specimens, CMC (0.25 wt %) had a thinner tip than those of the other thickness adjustment foods, and more widely diffused on the tilted plate. On the other hand, as shown in FIG. 15(a) to FIG. 15(d), it was not possible to visually find a significant difference between the shapes of the tips of the high-thickness foods and those of the other samples.

Thus, as shown in FIG. 16(a) to FIG. 16(d), the macroscale dynamic contact angle was measured by the present measurement system. The contact angles of the high-thickness specimens were as follows: 149.2° for XG (FIG. 16(a)), 147.2° for SG (FIG. 16(b)), 145.8° for GG (FIG. 16(c)), and 143.4° for CMC (FIG. 16(d)). Therefore, the device according to the present invention could qualitatively evaluate, with the dynamic contact angle, the difference of shape between the specimens that could not be visually checked.

Next, the downward flow locus of each of the alimentary boluses (specimens) was digitized and the diffusion area was thereby checked. The diffusion areas of the high-thickness specimens are separately shown in FIG. 17(*a*) to FIG. 17(*d*) regarding the upper region (at the time of the arrival in the upper sensor), in FIG. 18(*a*) to FIG. 18(*d*) regarding the middle region (at the time of the arrival in the middle sensor), and in FIG. 19(*a*) to FIG. 19(*d*) regarding the lower region (at the time of the arrival in the lower sensor).

Figure 17:
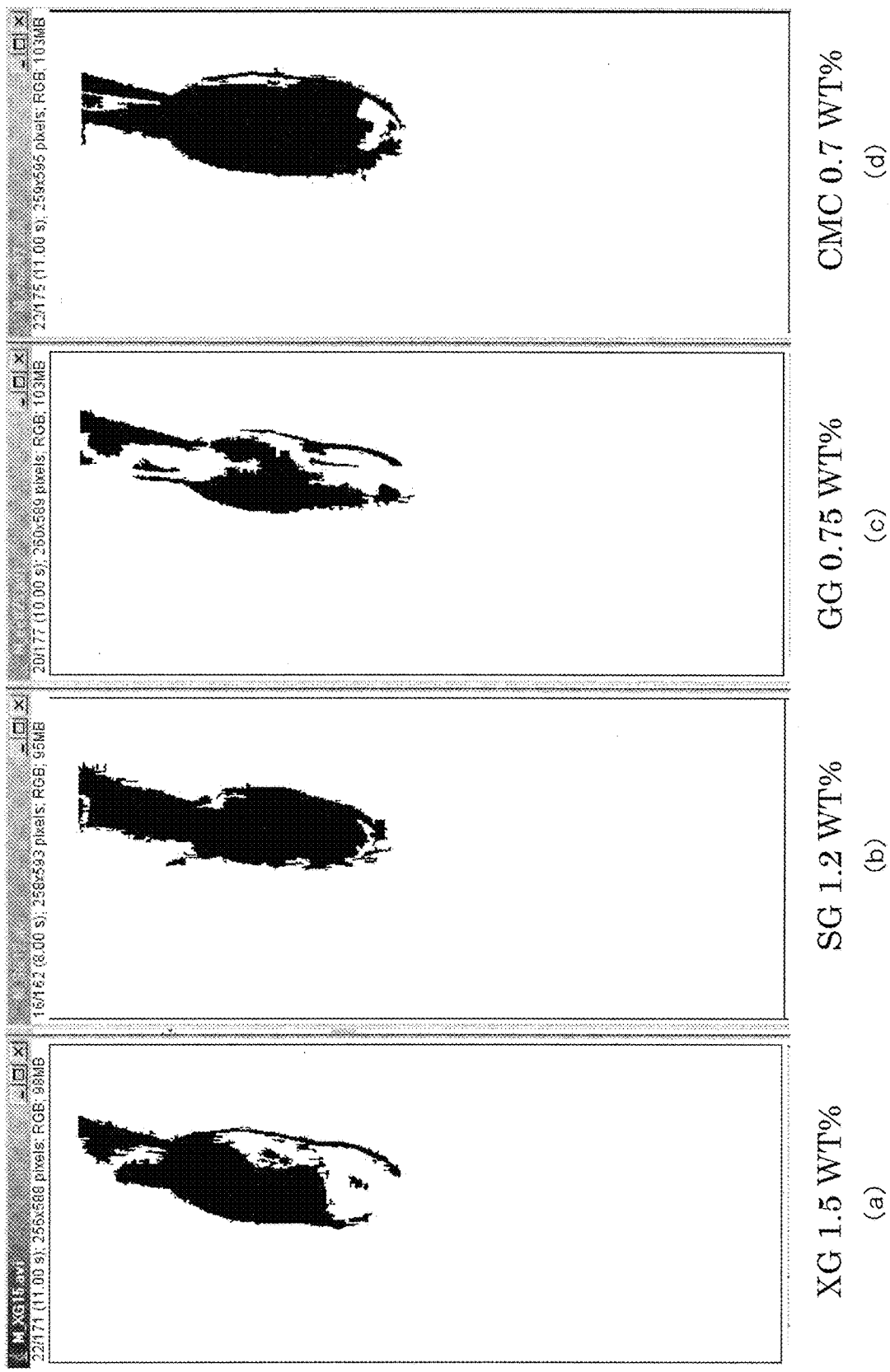
FIG. 17(a) to FIG. 17(d) show upper images of the diffusion area (an upper region of the tilted plate) at the moment of the arrival of the alimentary bolus in the upper sensor.
Figure 18:
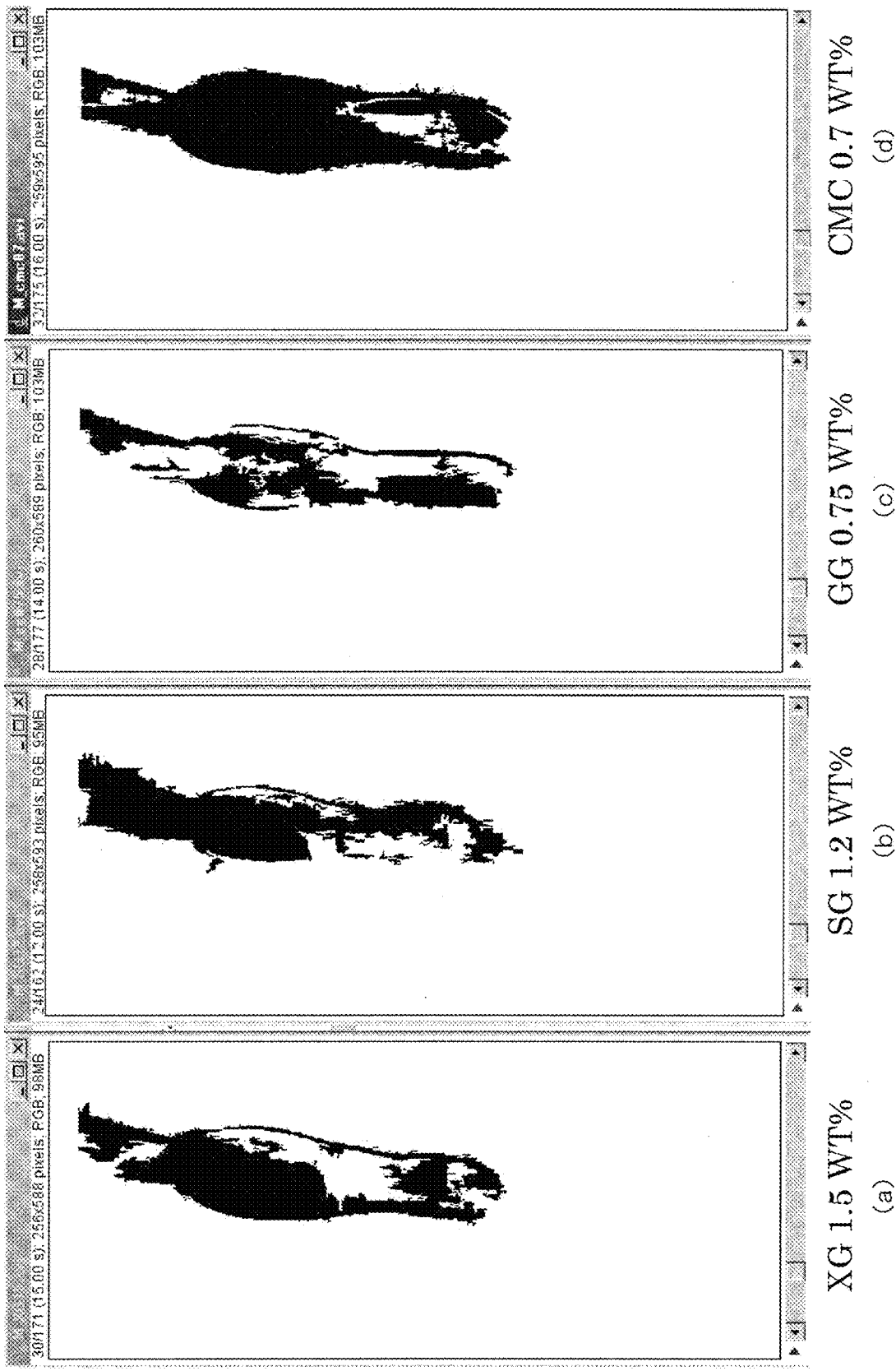
FIG. 18(a) to FIG. 18(d) show upper images of the diffusion area (a middle region of the tilted plate) at the moment of the arrival of the alimentary bolus in the middle sensor.
Figure 19:
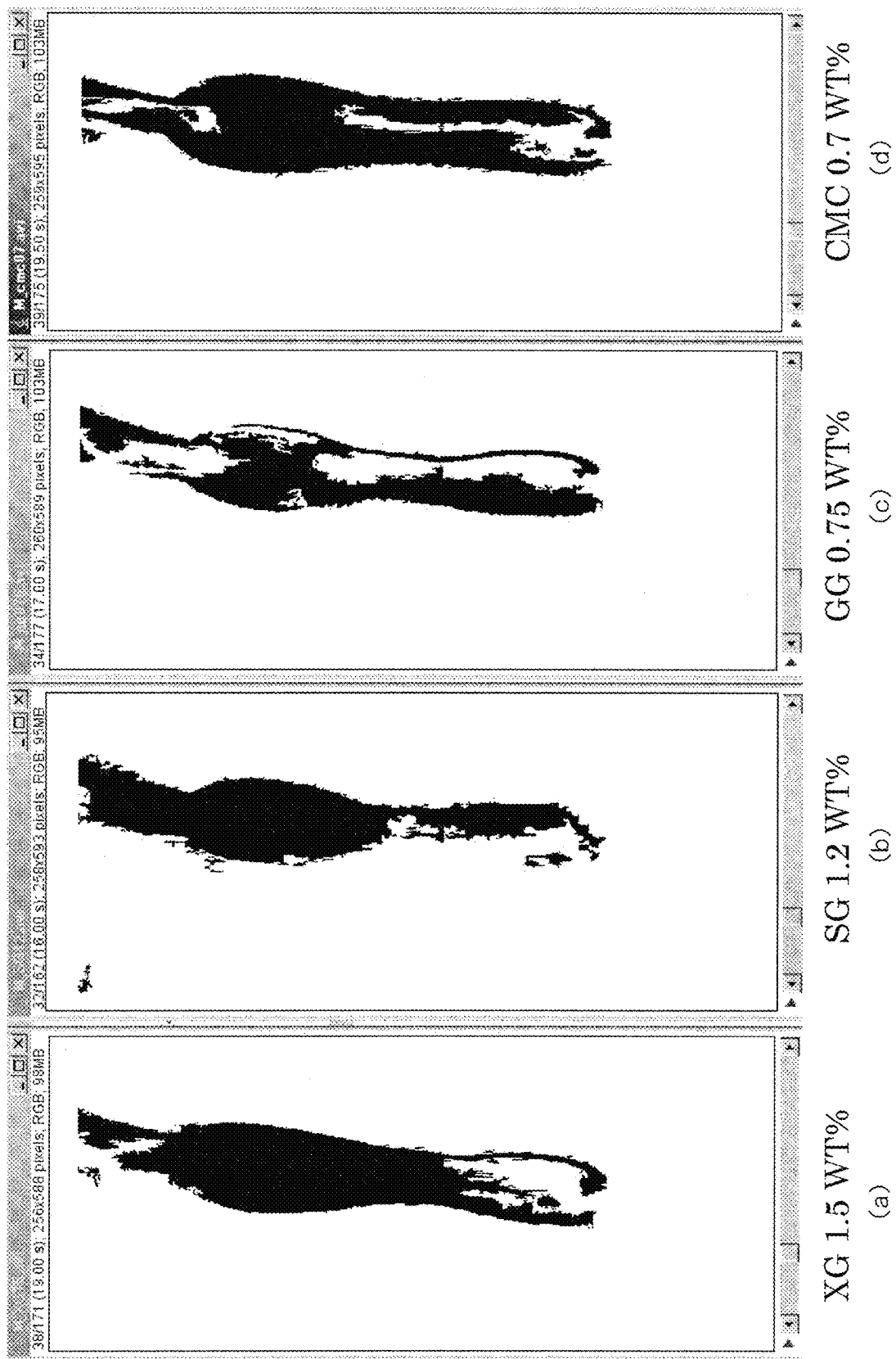
FIG. 19(a) to FIG. 19(d) show upper images of the diffusion area (a lower region of the tilted plate) at the moment of the arrival of the alimentary bolus in the lower sensor.

As shown in FIG. 17(*a*) to FIG. 17(*d*), it was possible to visually check that the diffusion areas of SG and GG were slightly smaller than the diffusion areas of XG and CMC, In FIG. 18(*a*) to FIG. 18(*d*) and FIG. 19(*a*) to FIG. 19(*d*), it was possible to visually check that the diffusion areas of SG and GG were slightly smaller than the diffusion areas of XG and CMC, as in FIG. 17(*a*) to FIG. 17(*d*).

Figure 20:
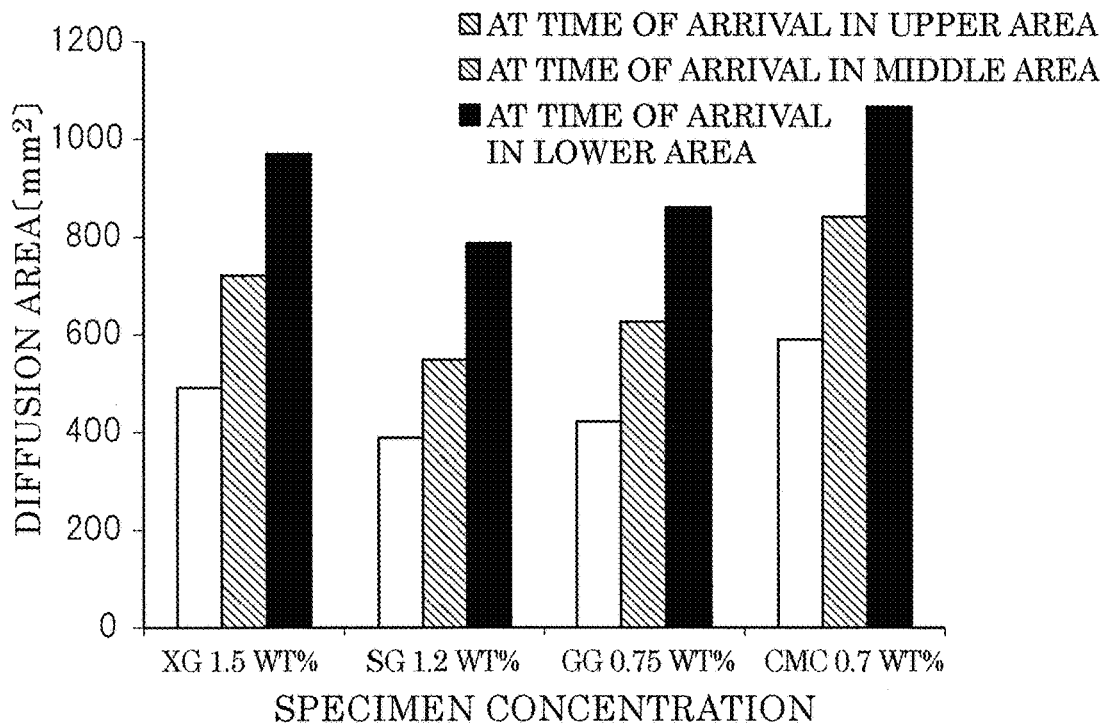
FIG. 20 shows diffusion areas (by measurement areas) of different specimens.

In addition to the visual observation, the changes of these diffusion areas are shown in FIG. 20, The difference between the diffusion areas, which was a subtle difference in the visual observation, was converted into a numerical form and could thereby be clearly understood. 0.7 wt % CMC, 1.5 wt % XG, 0.75 wt % GG, and 1.2 wt % SG ranked in descending order of diffusion area. This tendency was the same in every observation region.

Figure 21:
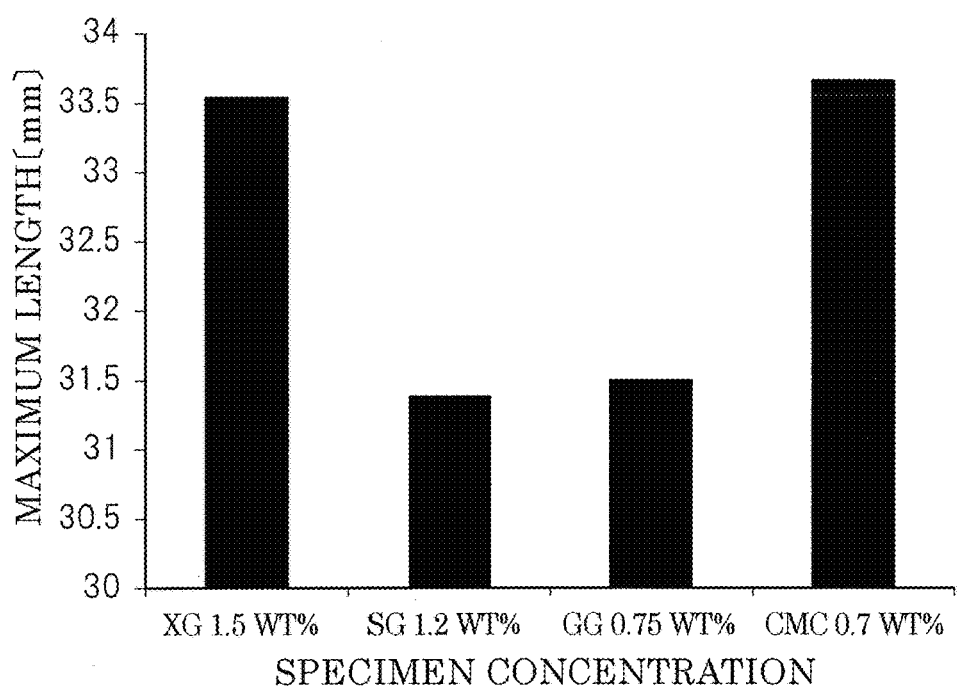
FIG. 21 shows the comparison of the maximum lengths obtained from downward flow loci in an upper observation area.
Figure 22:
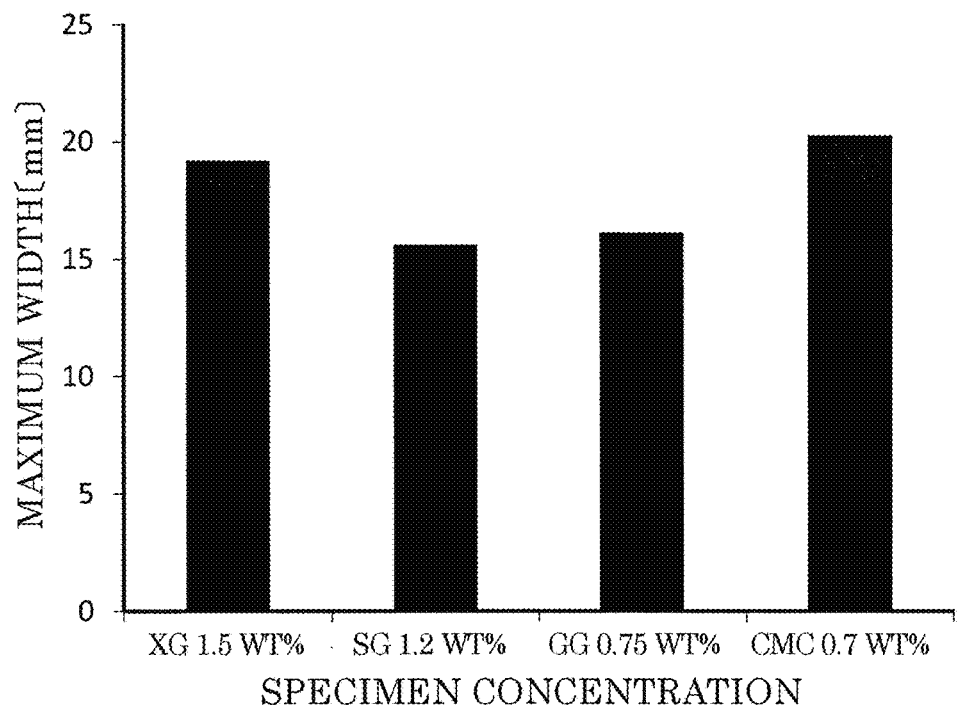
FIG. 22 shows the comparison of the maximum widths obtained from the downward flow loci in the upper observation area.

The maximum lengths measured from the downward flow loci are shown in FIG. 21, and the maximum widths are shown in FIG. 22. As shown in FIG. 21, the maximum lengths of XG and CMC were greater than those of SG and GG. As shown in FIG. 22, the maximum widths of XG and CMC were obviously greater than those of SG and GG. By the way, XG and SG had the same properties in viscosity-shear rate relation curves (flow curves). That is, the property values of the flow curves do not necessarily correspond to the downward flow properties. This qualitatively explains the cause of the actual phenomenon of mouthfeel wherein even if a sensory test of specimens which seem to show about the same flow curve is conducted, a similar evaluation (mapping) is not always obtained.

Examples of dynamic property values (engineering indices) measured by the present device are shown (Table 5). Shear velocity and shear stress can be only measured from the velocity distribution of flux inside the liquid droplet in PATENT LITERATURE 3. By great contrast, force on the wall surface and energy consumed in the wall surface can also be measured by the present measurement method. The method of measuring force and energy is as follows:

$$(F)[N]: \text{force} = \tau \times Sm$$

$$W[W]: \text{energy} = (F) \times U$$

wherein $U[m/s]$ is a passing velocity between the upper and lower sensors, $\delta[m]$ is the thickness of the alimentary bolus obtained from the side measurement, $\gamma[1/s]$ is shear velocity$=U/\delta$, $\mu[pa \cdot s]$ is viscosity, $\tau[N/m^2]$ is shear stress$=\mu \times U/\delta$, and $Sm[m^2]$ is the diffusion area in the middle part.

Figure 23:
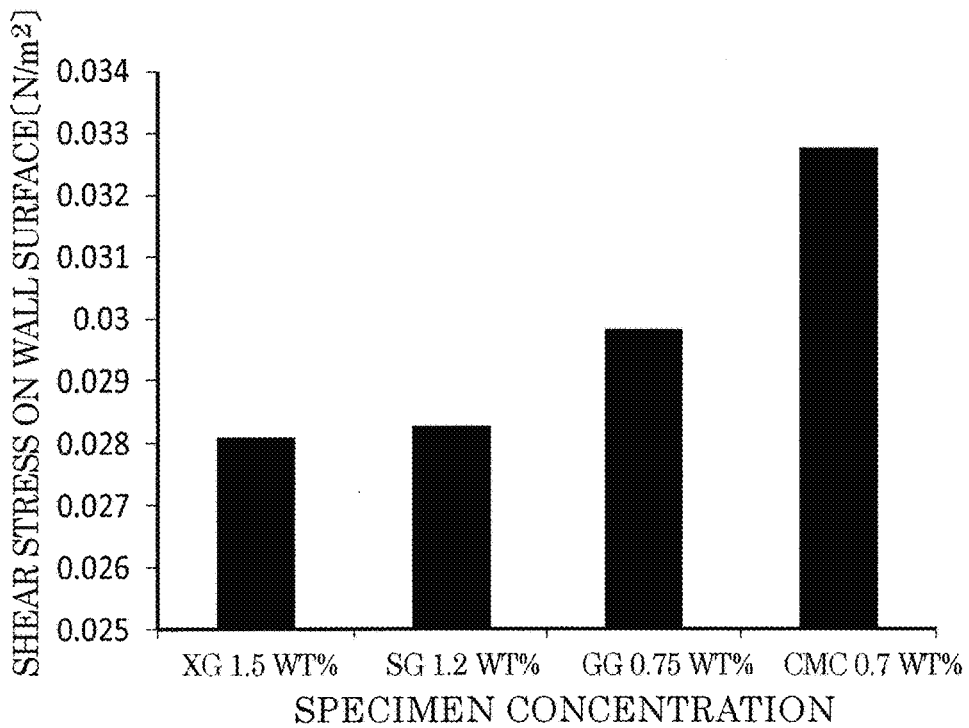
FIG. 23 shows the difference of wall surface shear stress.

The shear stress of each specimen in the wall surface is shown in FIG. 23. The shear stress of each specimen showed a tendency (classification) similar to that of the flow curve shown in FIG. 11. XG and SG were on the same line of the flow curve, but GG and CMC were out of this line. The shear stress of each specimen also showed such a tendency.

Figure 24:
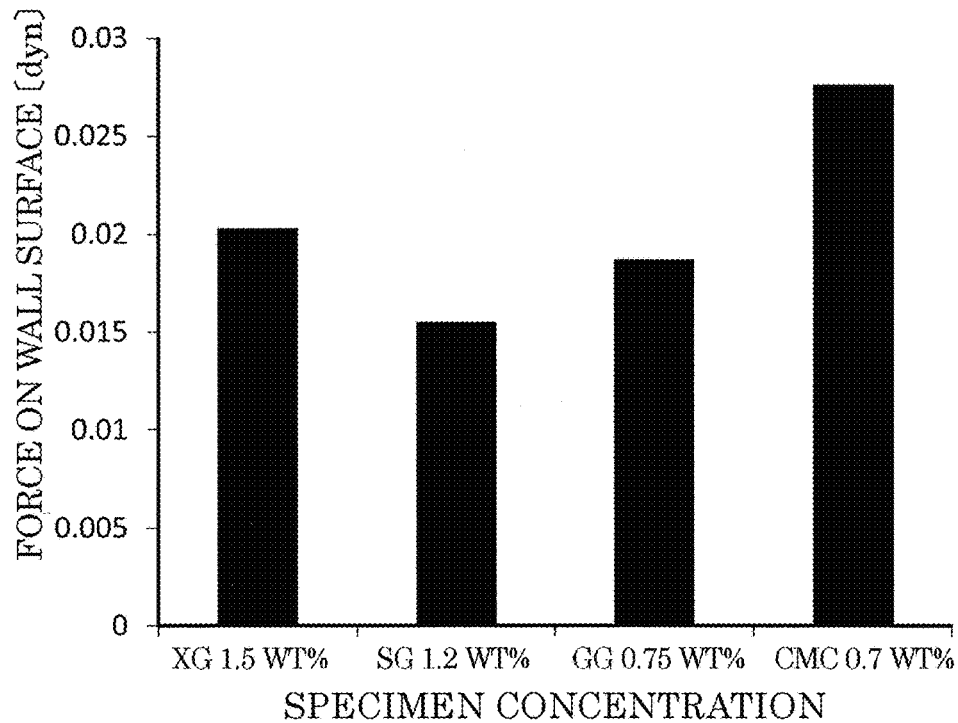
FIG. 24 shows the difference of force on the wall surface.

The force of each specimen on the wall surface is compared in FIG. 24. The force of each specimen showed a tendency different from the characteristics of the flow curve shown in FIG. 11, as opposed to the tendency of the shear stress.

Figure 25:
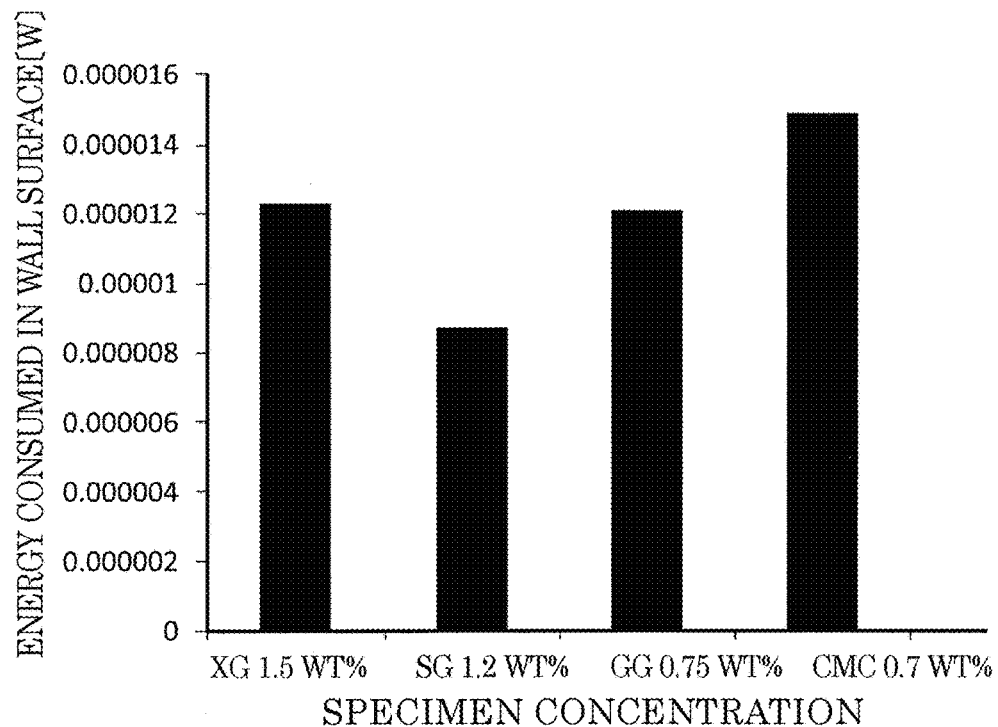
FIG. 25 shows the comparison of energy consumed in the wall surface.

A comparison result of energy consumed in the wall surface is shown in FIG. 25. As is the case in the force in FIG. 24, the energy on the wall surface is significantly different from the characteristics of the flow curve shown in FIG. 11.

The present measurement device shown in FIG. 1 could compute, from various measurement values, the shear velocity, the shear stress on the wall surface, the force on the wall surface, and the energy consumed in the wall surface. Thereby, the downward flow properties specific to food could be objectively clarified. The present measurement device could objectively clarify the downward flow properties specific to food that could not have been objectively and quantitatively measured by conventional arts.

TABLE 5

| | Dynamic Properties of High-Thickness Alimentary Boluses | | | |
|---|---|---|---|---|
| | Unit | XG (1.5 wt %) | SG (1.2 wt %) | GG (0.75 wt %) | CMC (0.7 wt %) |
| Diffusion area in upper region | [mm$^2$] | 492 | 388 | 422 | 590 |
| Diffusion area in middle region | [mm$^2$] | 722 | 549 | 626 | 841 |
| Diffusion area in lower region | [mm$^2$] | 969 | 787 | 861 | 1066 |
| Maximum length of upper region | [mm] | 33.54 | 31.38 | 31.5 | 33.7 |
| Maximum width of upper region | [mm] | 19.2 | 15.6 | 16.1 | 20.2 |
| (Average) velocity between upper and lower sensors | [m/sec] | 0.607 | 0.562 | 0.647 | 0.542 |
| Angle during downward flowing | [°] | 30.8 | 32.8 | 34.2 | 36.6 |
| Contact angle during downward flowing | [°] | 149.2 | 147.2 | 145.8 | 143.4 |
| Thickness | [mm] | 7.09 | 7.34 | 7.22 | 6.58 |
| Thickness of center | [mm] | 3.55 | 3.67 | 3.61 | 3.29 |
| Shear velocity | [1/sec] | 171.2 | 153.1 | 179.2 | 164.7 |
| Viscosity | [Pa · s] | 0.164 | 0.185 | 0.166 | 0.199 |
| Shear stress on wall surface | [N/m$^2$] | 0.0281 | 0.0283 | 0.0298 | 0.03278 |

TABLE 5-continued

Dynamic Properties of High-Thickness Alimentary Boluses

|  | Unit | XG (1.5 wt %) | SG (1.2 wt %) | GG (0.75 wt %) | CMC (0.7 wt %) |
|---|---|---|---|---|---|
| Force on wall surface | [dyn] | 0.0203 | 0.0155 | 0.0187 | 0.0276 |
| Energy consumed in wall surface | [W] | 0.0000123 | 0.00000872 | 0.0000121 | 0.0000149 |

Example 7

The downward flow properties of various fermented milk foods were checked by the measurement device shown in FIG. 1. However, in the present example, the tilted surface of the tilted plate was made of a false living body material (hydrophilic PVA) using polyvinyl alcohol which is closer to the inner surface of the oral cavity than silicon.

Three kinds of fermented dairy products (a specimen (A), a specimen (B), and a specimen (C)) were used as specimens. The compositions of nonfat milk solid, milk fat, protein, fat, and carbohydrate in the three kinds of fermented dairy products are as shown in Table 6.

TABLE 6

| Component | Unit | A | B | C |
|---|---|---|---|---|
| Nonfat milk solid | [wt %] | 9.5 | 8.3 | 9.2 |
| Milk fat | [wt %] | 3.0 | 3.5 | 3.7 |
| Protein | [wt %] | 3.4 | 3.2 | 3.4 |
| Fat | [wt %] | 3.0 | 3.6 | 3.8 |
| Carbohydrate | [wt %] | 5.3 | 4.7 | 9.5 |

Figure 26:
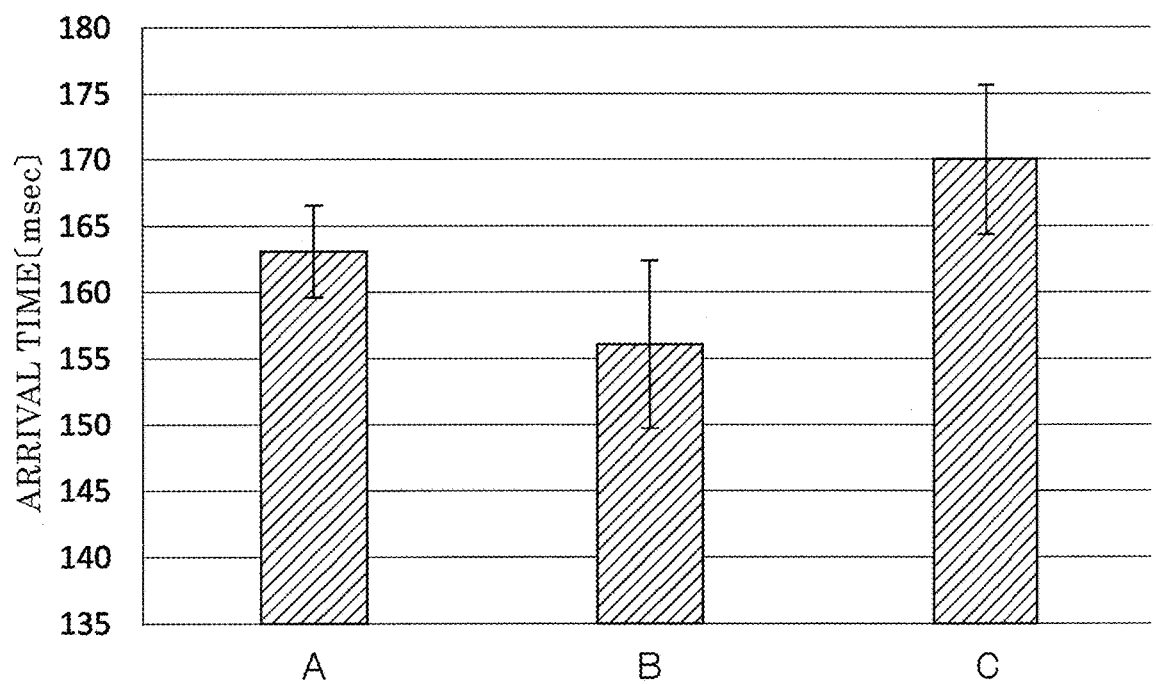
FIG. 26 shows a graph indicating arrival times from the discharge of specimens from a nozzle to the arrival at a detection position of the upper arrival check sensor.
Figure 27:
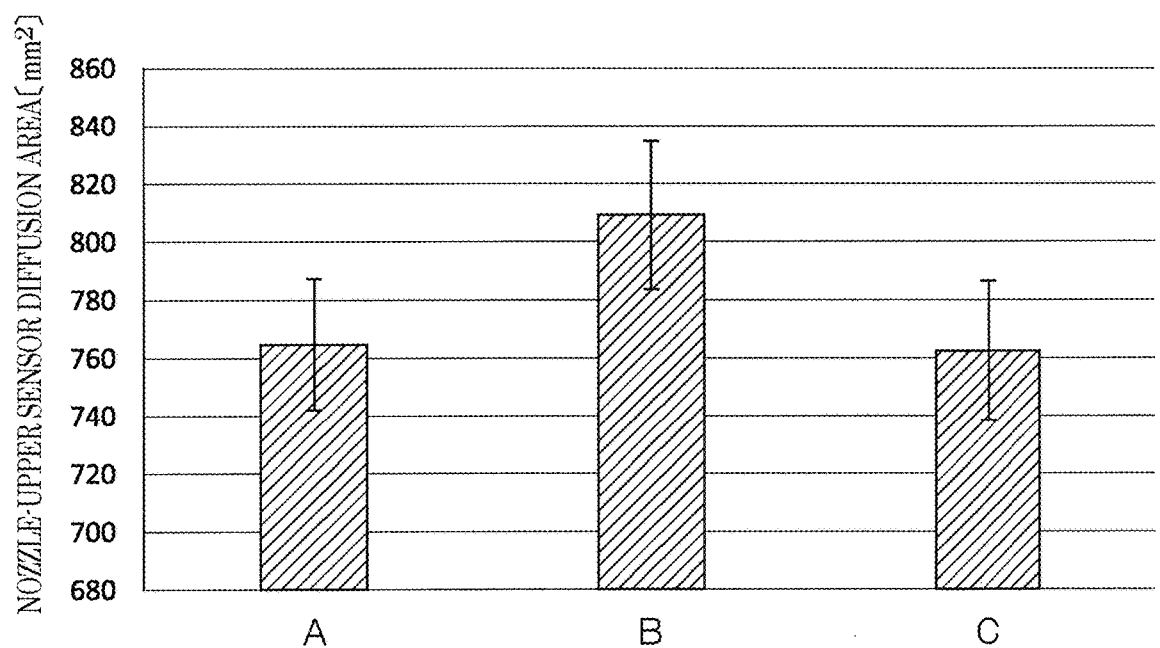
FIG. 27 shows a graph indicating the diffusion areas of the specimens downwardly flowing on a tilted surface on an upstream side from the detection position of the upper arrival check sensor.
Figure 28:
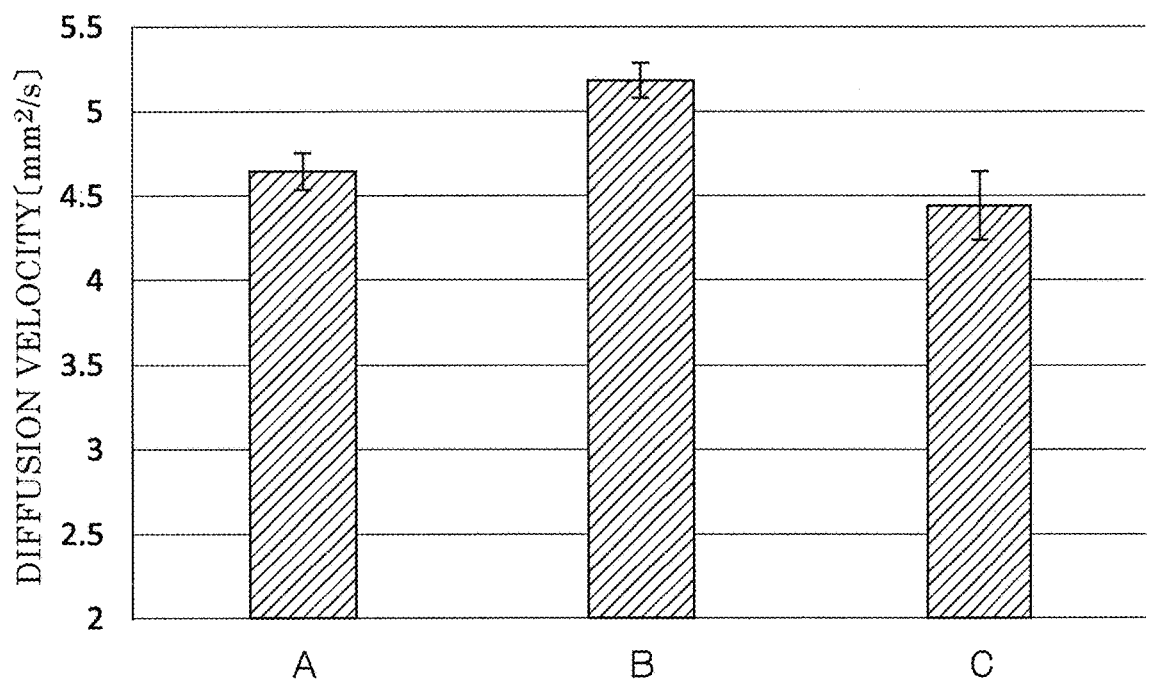
FIG. 28 shows a graph indicating the diffusion areal velocities of the specimens downwardly flowing on the tilted surface on the upstream side from the detection position of the upper arrival check sensor.

Measurement results of the motion of the specimens (A) to (C) in the upstream part of the tilted surface are shown in FIG. 26 to FIG. 28.

FIG. 26 shows arrival times from the discharge of the specimens (A) to (C) from the nozzle to the arrival at a detection position of the upper arrival check sensor. As shown in this diagram, the specimen (B) showed an arrival time shorter than those of the remaining specimens (A) and (C).

FIG. 27 shows the diffusion areas of the specimens (A) to (C) downwardly flowing on the tilted surface on an upstream side from the detection position of the upper arrival check sensor. As shown in this diagram, the specimen (B) showed a diffusion area larger than those of the remaining specimens (A) and (C).

FIG. 28 shows the diffusion areal velocities of the specimens (A) to (C) downwardly flowing on the tilted surface on the upstream side from the detection position of the upper arrival check sensor. As shown in this diagram, the specimen (B) showed a diffusion areal velocity higher than those of the remaining specimens (A) and (C).

Figure 29:
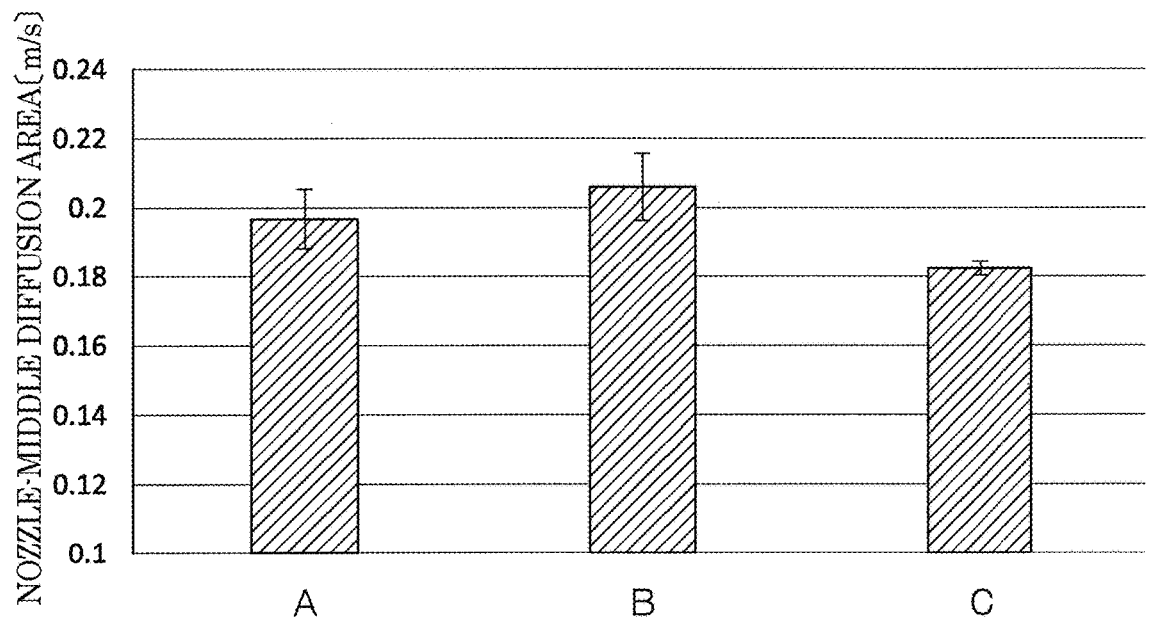
FIG. 29 shows a graph indicating the interval velocities of the specimens downwardly flowing on the tilted surface between the detection position of the upper arrival check sensor and the detection position of the middle arrival check sensor.
Figure 30:
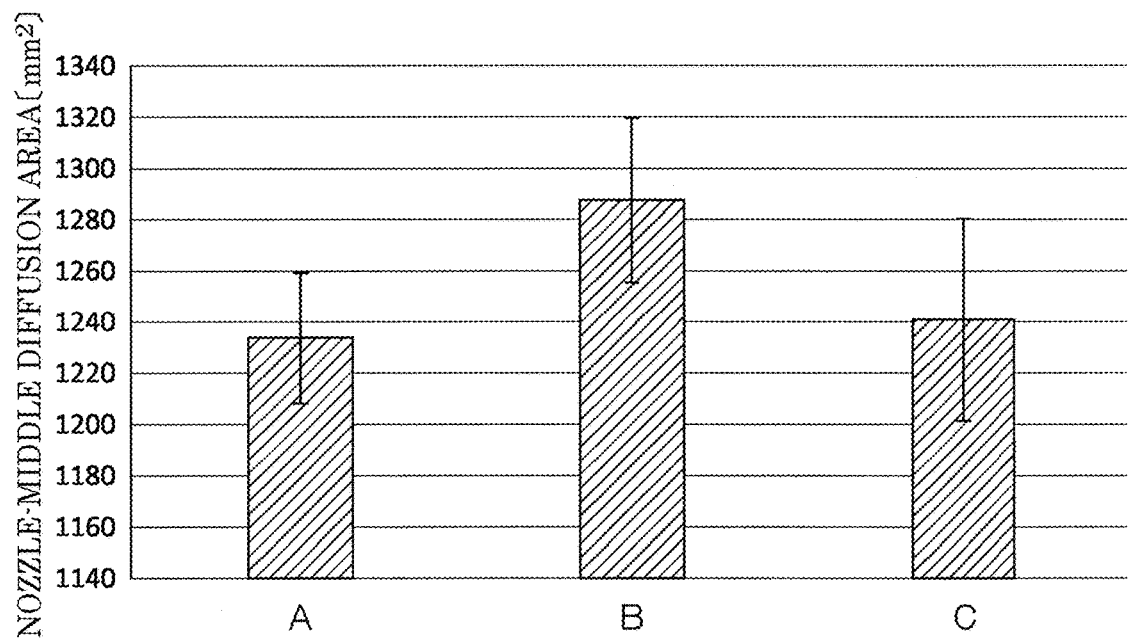
FIG. 30 shows a graph indicating the diffusion areas of the specimens downwardly flowing on the tilted surface between the detection position of the upper arrival check sensor and the detection position of the middle arrival check sensor.
Figure 31:
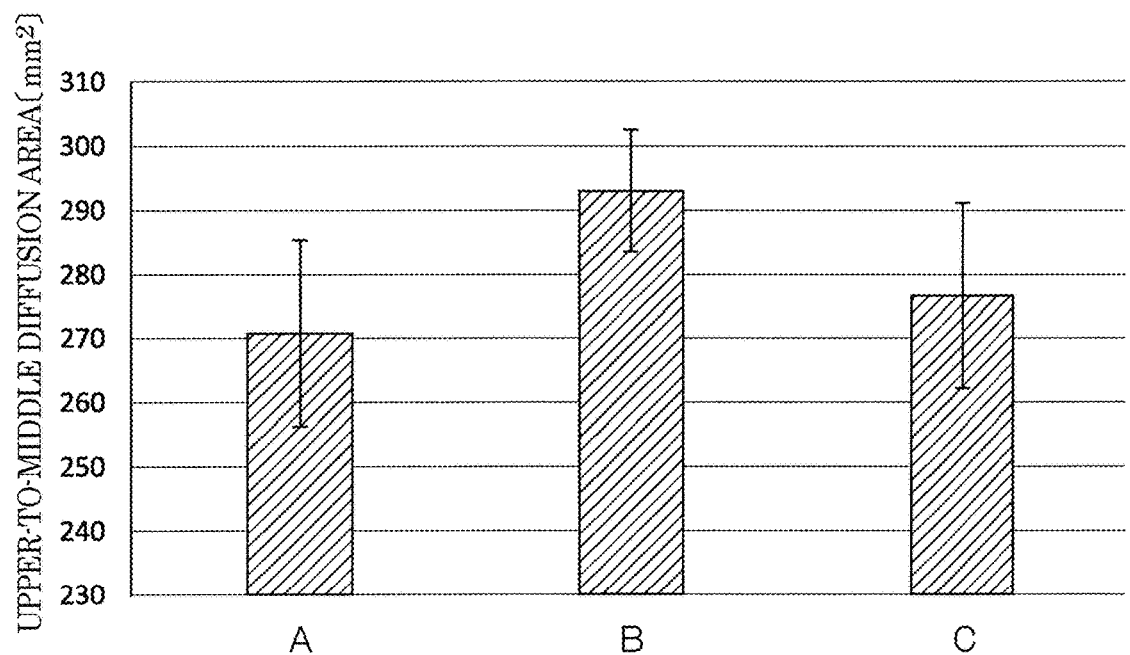
FIG. 31 shows a graph indicating the diffusion areal velocities of the specimens downwardly flowing on the tilted surface between the detection position of the upper arrival check sensor and the detection position of the middle arrival check sensor.

Next, measurement results of the motion of the specimens (A) to (C) in the middle part of the tilted surface are shown in FIG. 29 to FIG. 31.

FIG. 29 shows the interval velocities of the specimens (A) to (C) downwardly flowing on the tilted surface between the detection position of the upper arrival check sensor and the detection position of the middle arrival check sensor. As shown in this diagram, the specimen (A) and the specimen (B) showed about the same interval velocity, and the specimen (C) showed an interval velocity lower than those of the specimens (A) and (B).

FIG. 30 shows the diffusion areas of the specimens (A) to (C) downwardly flowing on the tilted surface between the detection position of the upper arrival check sensor and the detection position of the middle arrival check sensor. As shown in this diagram, the specimen (B) showed a diffusion area larger than those of the remaining specimens (A) and (C) in the middle part of the tilted surface as well.

FIG. 31 shows the diffusion areal velocities of the specimens (A) to (C) downwardly flowing on the tilted surface between the detection position of the upper arrival check sensor and the detection position of the middle arrival check sensor. As shown in this diagram, the specimen (B) showed a diffusion areal velocity higher than those of the remaining specimens (A) and (C) in the middle part of the tilted surface as well.

Figure 32:
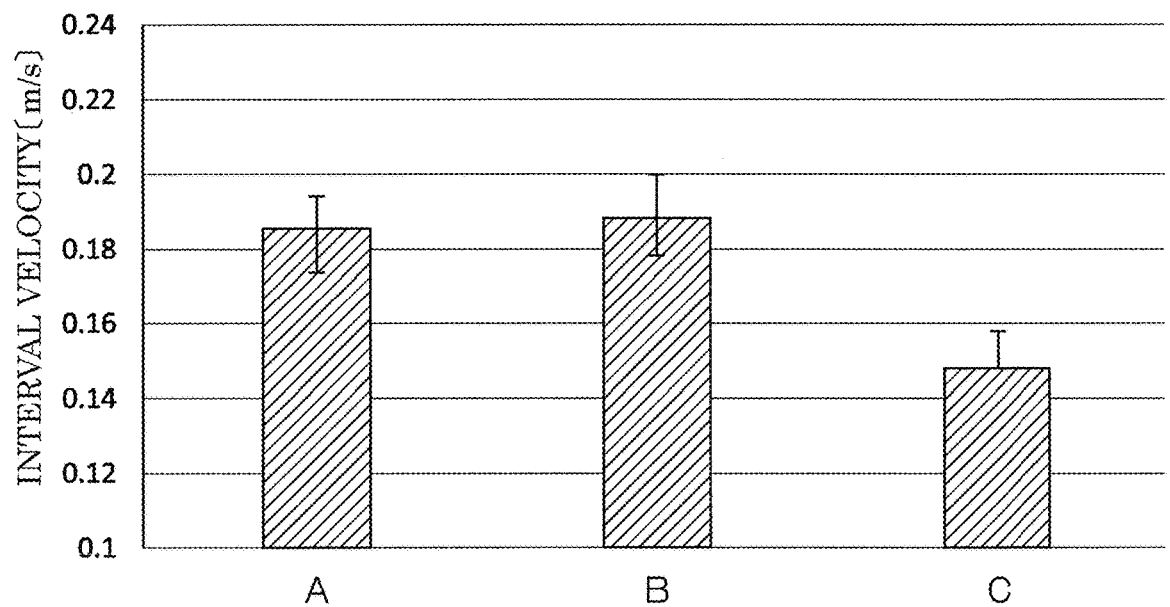
FIG. 32 shows a graph indicating the interval velocities of the specimens downwardly flowing on the tilted surface between the detection position of the middle arrival check sensor and the detection position of the lower arrival check sensor.
Figure 33:
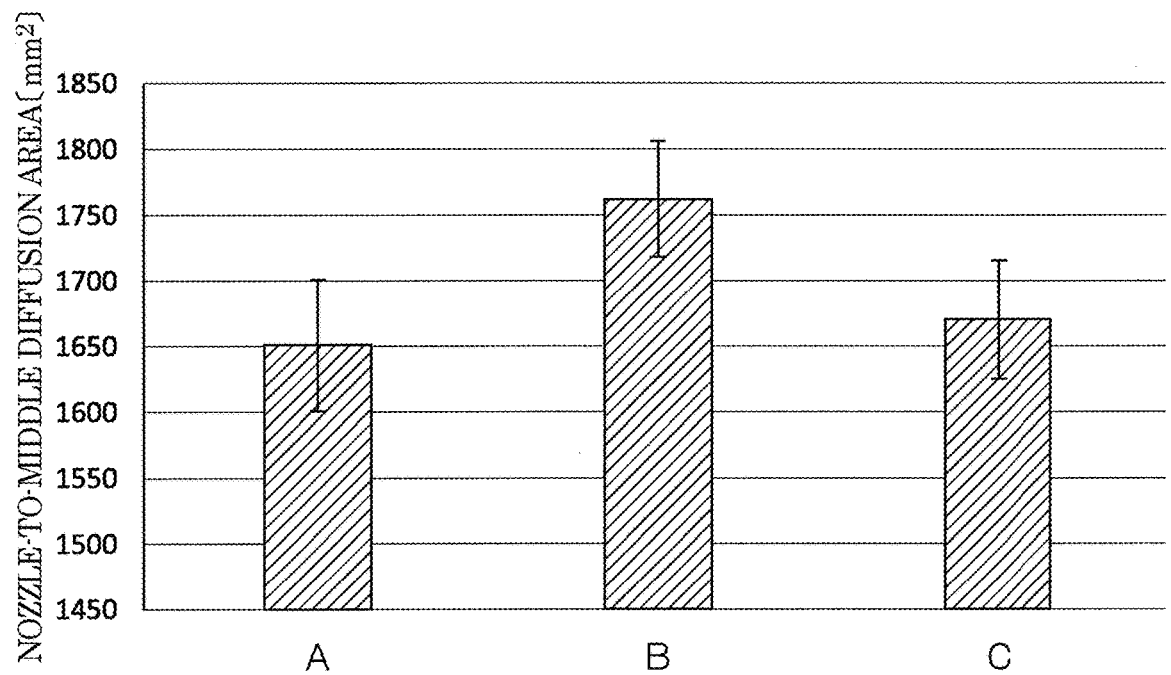
FIG. 33 shows a graph indicating the diffusion areas of the specimens downwardly flowing on the tilted surface between the detection position of the middle arrival check sensor and the detection position of the lower arrival check sensor.

Next, measurement results of the motion of the specimens (A) to (C) in the middle part of the tilted surface are shown in FIG. 32 and FIG. 33.

FIG. 32 shows the interval velocities of the specimens (A) to (C) downwardly flowing on the tilted surface between the detection position of the middle arrival check sensor and the detection position of the lower arrival check sensor. As shown in this diagram, the specimen (A) and the specimen (B) showed about the same interval velocity, and the specimen (C) showed an interval velocity lower than those of the specimens (A) and (B).

FIG. 33 shows the diffusion areas of the specimens (A) to (C) downwardly flowing on the tilted surface between the detection position of the middle arrival check sensor and the detection position of the lower arrival check sensor. As shown in this diagram, the specimen (B) showed a diffusion area larger than those of the remaining specimens (A) and (C) in the middle part of the tilted surface as well.

Figure 34:
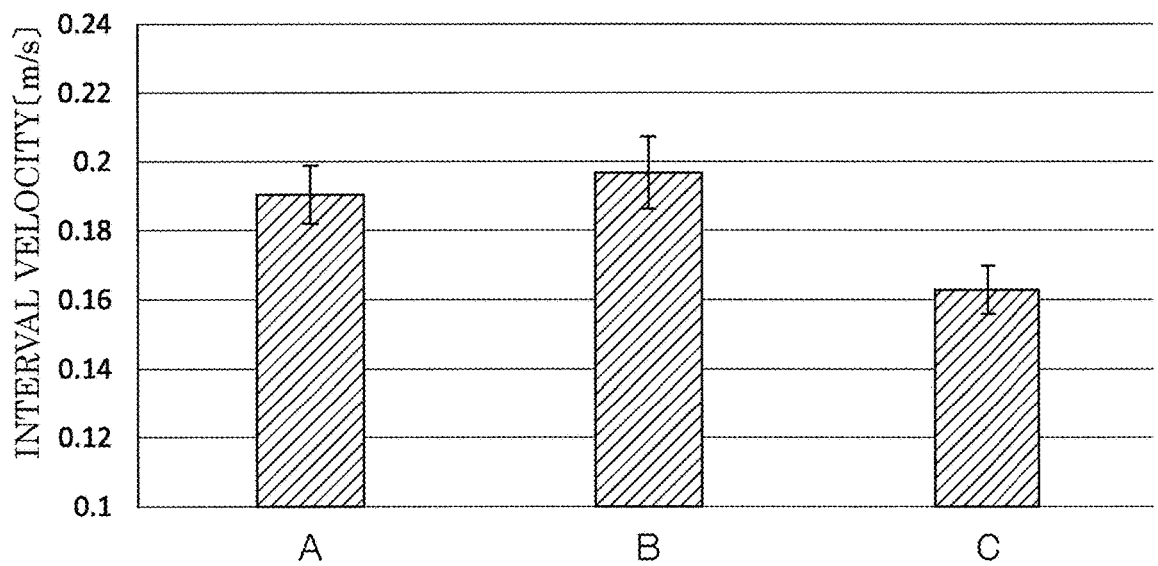
FIG. 34 shows a graph indicating the interval velocities of the specimens downwardly flowing on the tilted surface between the detection position of the upper arrival check sensor and the detection position of the lower arrival check sensor.

Next, measurement results of the motion of the specimens (A) to (C) in the whole tilted surface are shown in FIG. 34.

FIG. 34 shows the interval velocities of the specimens (A) to (C) downwardly flowing on the tilted surface between the detection position of the upper arrival check sensor and the detection position of the lower arrival check sensor. As shown in this diagram, the specimen (B) showed an interval velocity higher than those of the remaining specimens (A) and (C) in the whole tilted surface as well.

Figure 35:
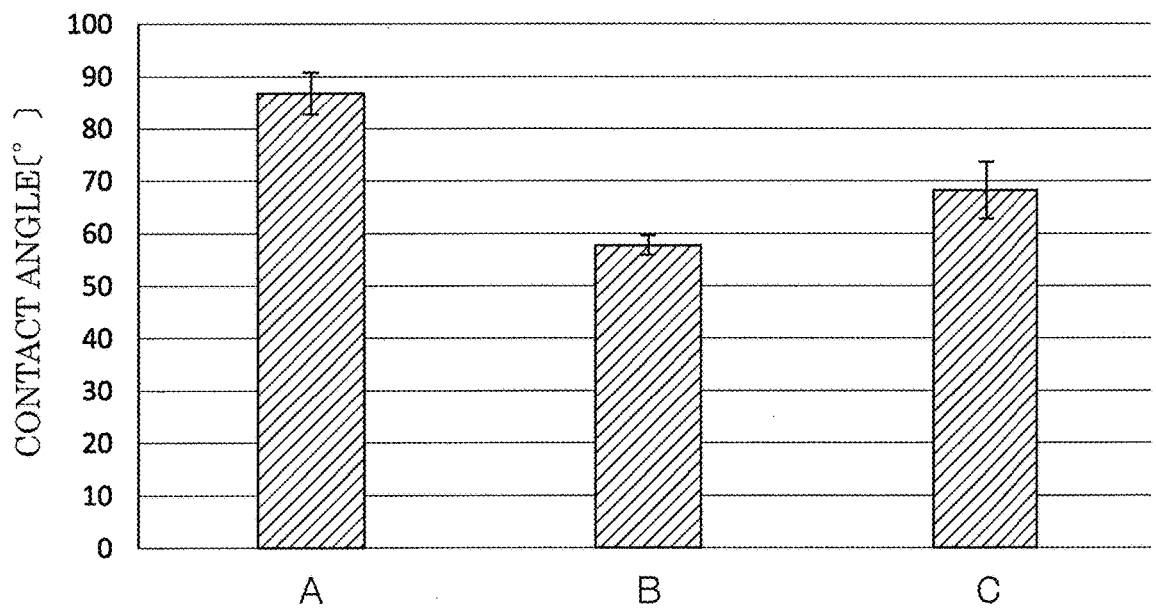
FIG. 35 shows a graph indicating the contact angles of the specimens.
Figure 36:
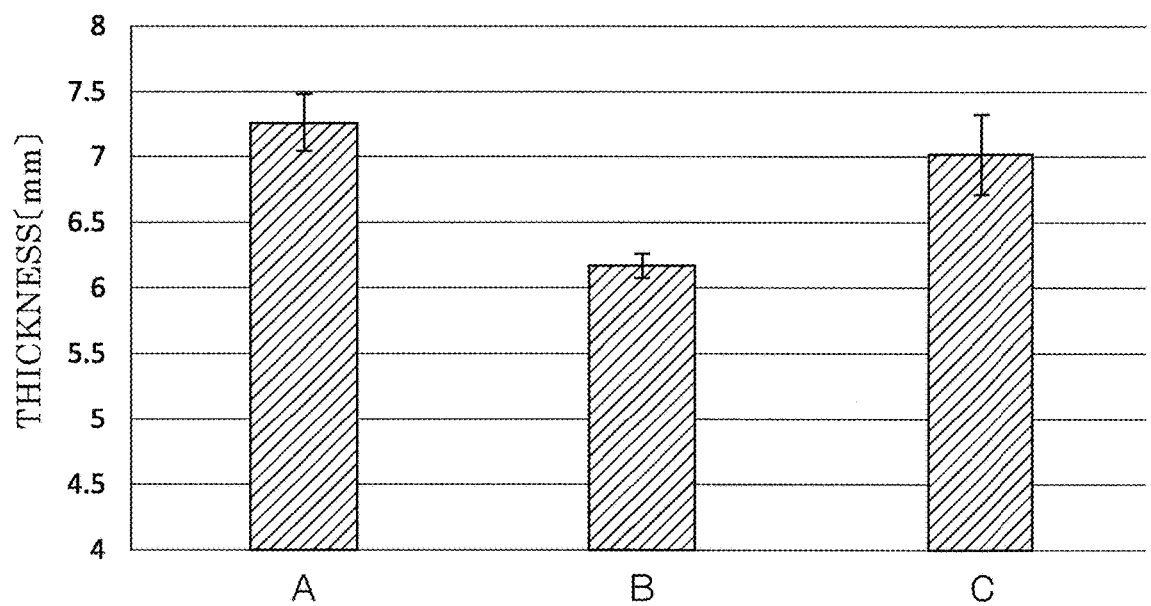
FIG. 36 shows a graph indicating the thicknesses of the specimens.

Next, measurement results of the shapes of the specimens (A) to (C) based on the side image are shown in FIG. 35 and FIG. 36.

FIG. 35 shows the contact angles of the specimens (A) to (C). As shown in this diagram, the specimen (A) showed a large contact angle, and the specimen (B) showed a small contact angle.

FIG. 36 shows the thicknesses of the specimens (A) to (C). As shown in this diagram, the specimen (A) showed a great thickness, and the specimen (B) showed a small thickness.

Figure 37:
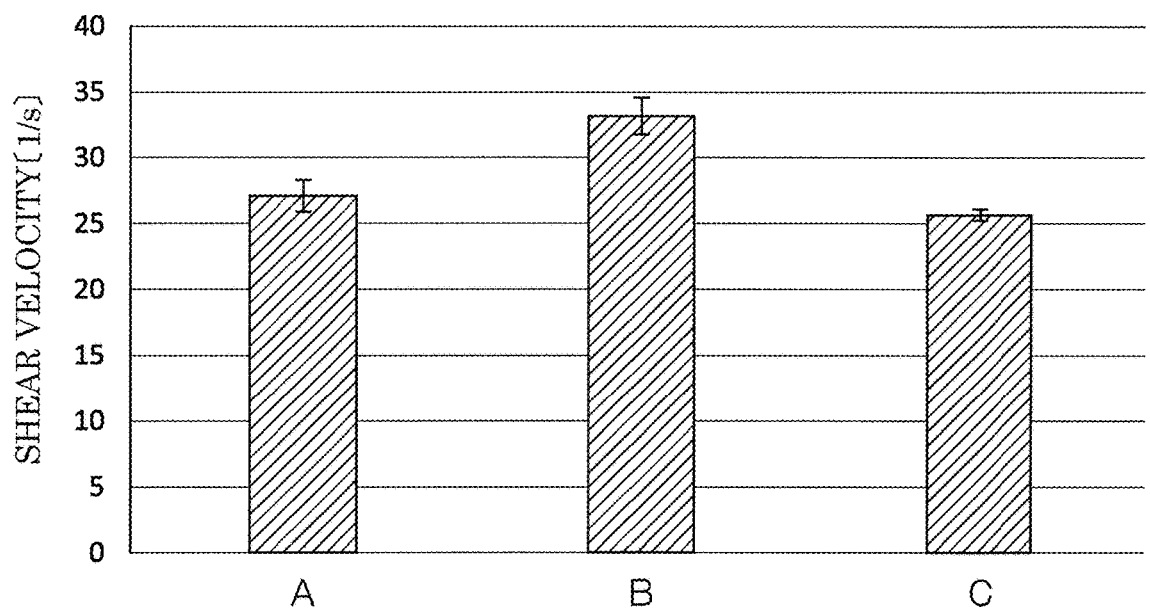
FIG. 37 shows a graph indicating the shear velocities of the specimens.

Next, shear velocities computed by dividing the downward flow velocities of the specimens (A) to (C) by their thicknesses are shown in FIG. 37. As shown in this diagram, the specimen (B) showed a shear velocity higher than those of the remaining specimens (A) and (C).

Figure 38:
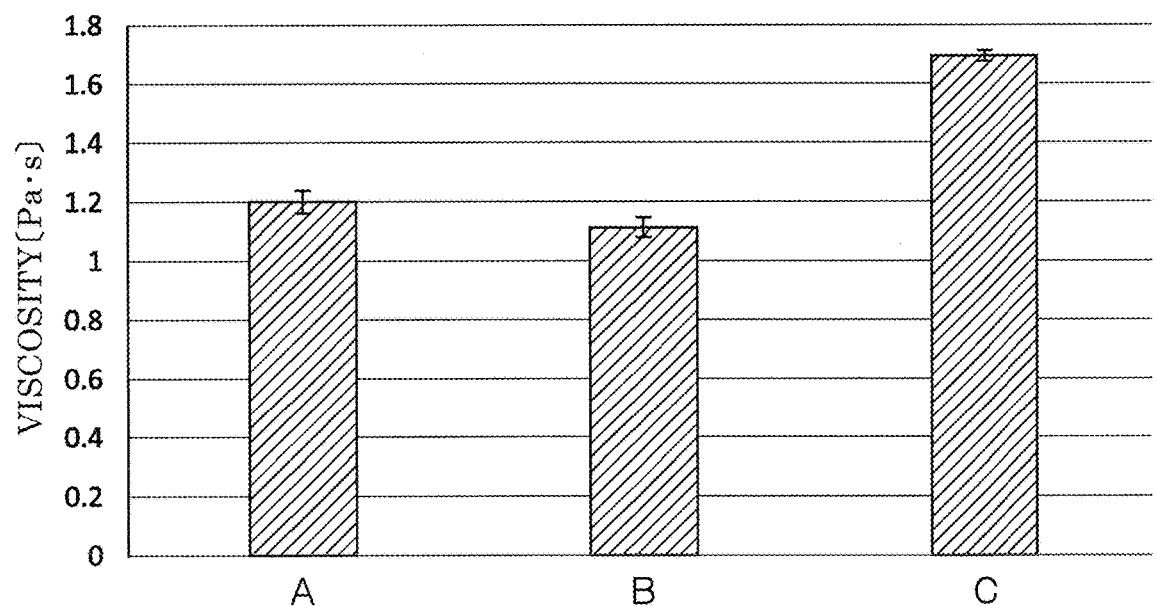
FIG. 38 shows a graph indicating the viscosities of the specimens.

Next, assumed values of the specimens (A) to (C) are shown in FIG. 38. As shown in this diagram, the specimen (C) showed a viscosity higher than those of the remaining specimens (A) and (B), and the specimens (A) and (B) showed about the same viscosity. Note that the viscosity was measured not by the measurement device shown in FIG. 1 but by the rheometer.

Figure 39:
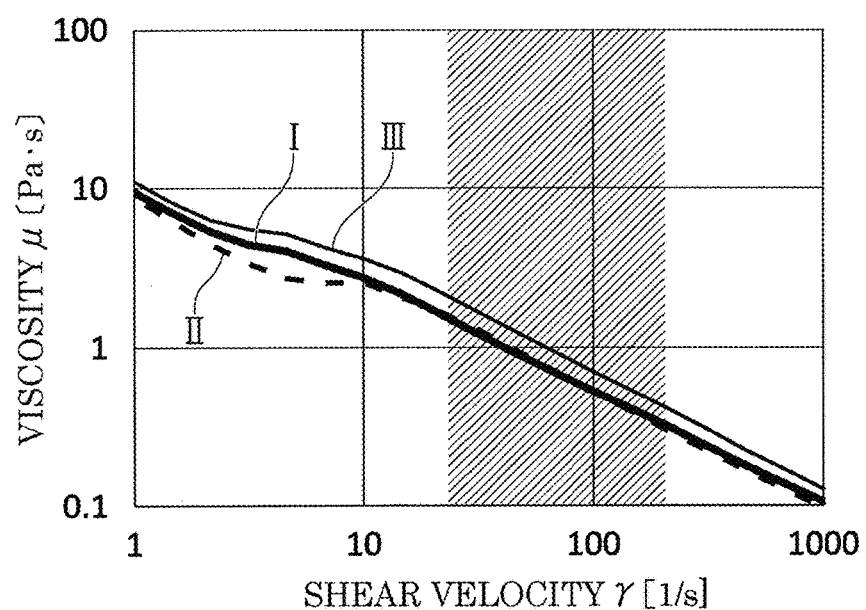
FIG. 39 shows evaluation mapping of specimens of different kinds of fermented milk foods according to a conventional evaluation method.

Here, an evaluation graph of the specimens (A) to (C) according to a conventional evaluation method is shown in FIG. 39. The horizontal axis in a map in FIG. 39 logarithmically represents shear velocity, and the vertical axis logarithmically represents viscosity. A solid line I, a broken line II, and a solid line III in the graph correspond to the specimens (A), (B), and (C), respectively.

It is considered that the shear velocity is 50 to 150 S-1 when a person is swallowing an alimentary bolus. This range is hatched in FIG. 39. In this range, the specimen (A) and the specimen (B) show about the same viscosity, so that the solid line I of the specimen (A) overlaps the broken line II of the specimen (B). It has therefore been difficult to differentiate between the specimen (A) and the specimen (B) by the conventional evaluation method.

However, a person evaluates the mouthfeel of an alimentary bolus using information in addition to viscosity, and it has therefore been evident that there is an obvious difference of mouthfeel between the specimen (A) and the specimen (B) in the sensory evaluation.

Thus, in the present experimental example, as described below, state parameters (indices) that represent states of the specimen downwardly flowing or falling on the tilted surface are calculated, and the specimens (A) to (C) are then evaluated. Measurement results and computation results by the present measurement device are used, and a plurality of dynamic indices are combined and then mapped, whereby mouthfeel of specimens can be objectively and precisely evaluated.

Thus, computation results of various state parameters of the specimens (A) to (C) are shown in FIG. 40 to FIG. 44.

Figure 40:
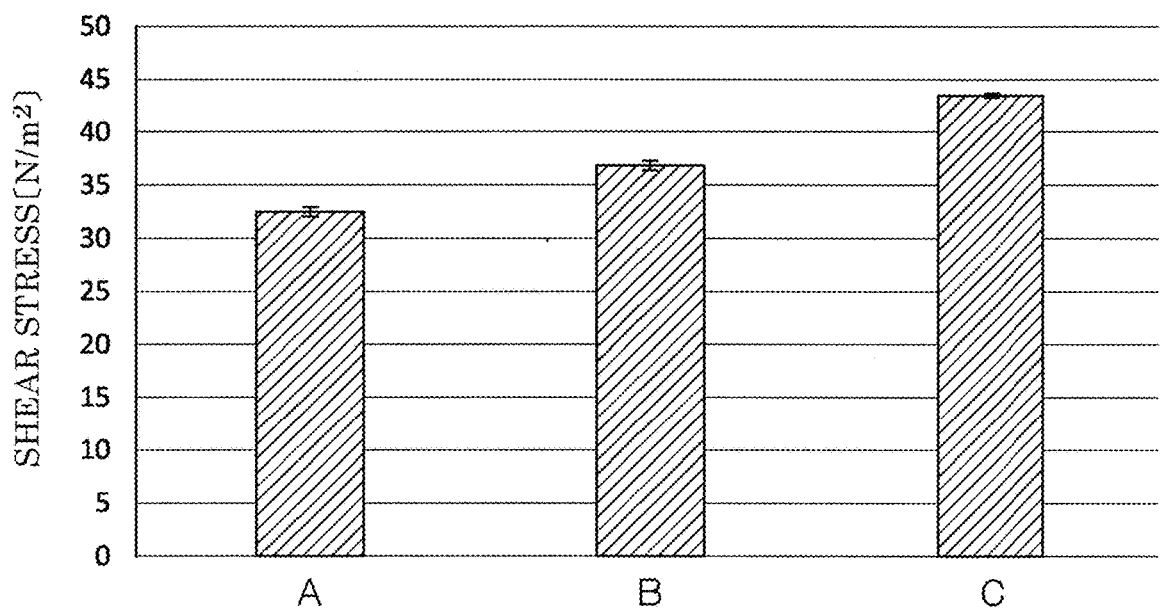
FIG. 40 shows a graph indicating the shear stress of the specimens on the tilted surface.

FIG. 40 shows the shear stress of the specimens (A) to (C) on the tilted surface. As shown in this diagram, the specimen (C) showed a high shear stress, and the specimen (A) showed a low shear stress.

Figure 41:
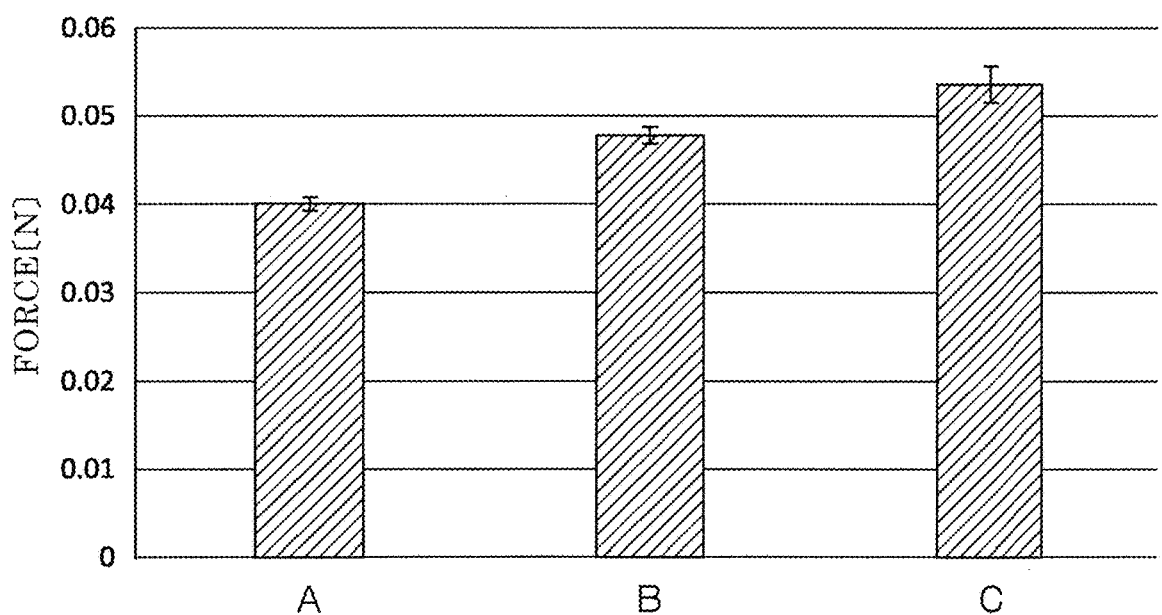
FIG. 41 shows a graph indicating the force of the specimens on the tilted surface.

FIG. 41 shows the force of the specimens (A) to (C) on the tilted surface. As shown in this diagram, the specimen (C) showed a great force, and the specimen (A) showed a small force.

Figure 42:
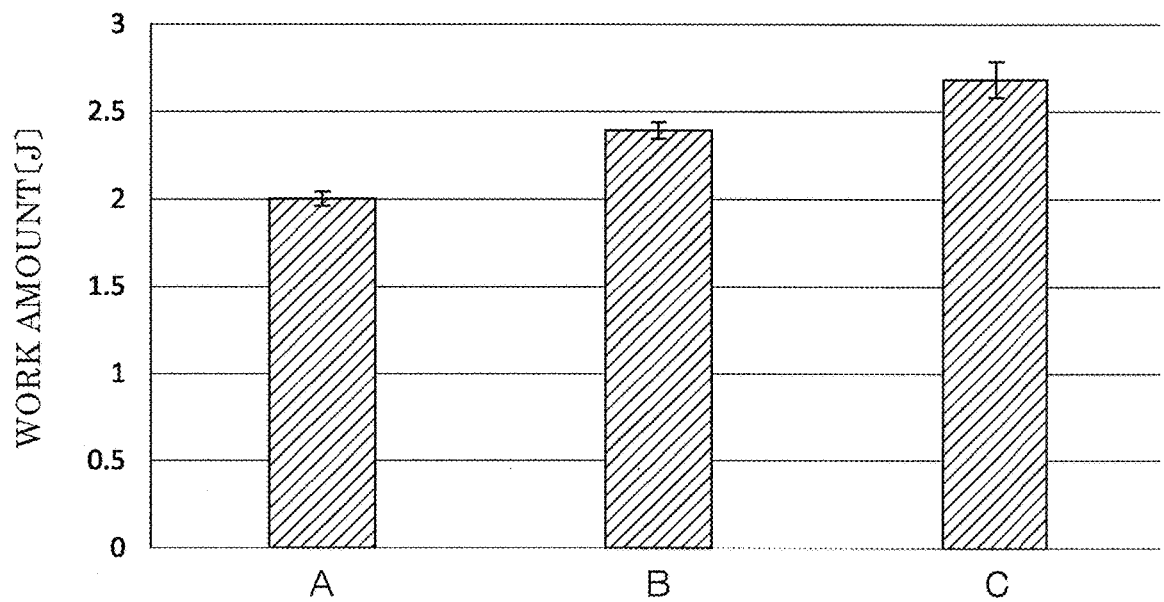
FIG. 42 shows a graph indicating the work amounts of the specimens on the tilted surface.

FIG. 42 shows the work amounts (the energy consumed in the wall surface) of the specimens (A) to (C) on the tilted surface. As shown in this diagram, the specimen (C) showed a great work amount, and the specimen (A) showed a small work amount.

Figure 43:
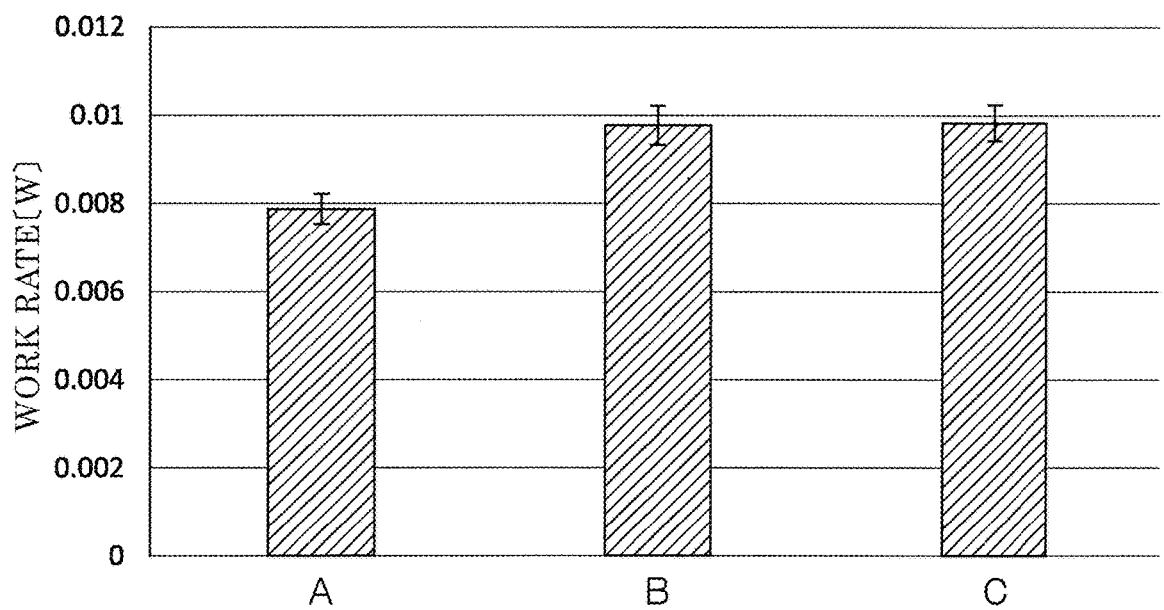
FIG. 43 shows a graph indicating the work rates of the specimens on the tilted surface.

FIG. 43 shows the work rates of the specimens (A) to (C) on the tilted surface. As shown in this diagram, the specimen (A) showed a work rate lower than those of the remaining specimens (B) and (C), and the specimens (B) and (C) showed about the same work rate.

Figure 44:
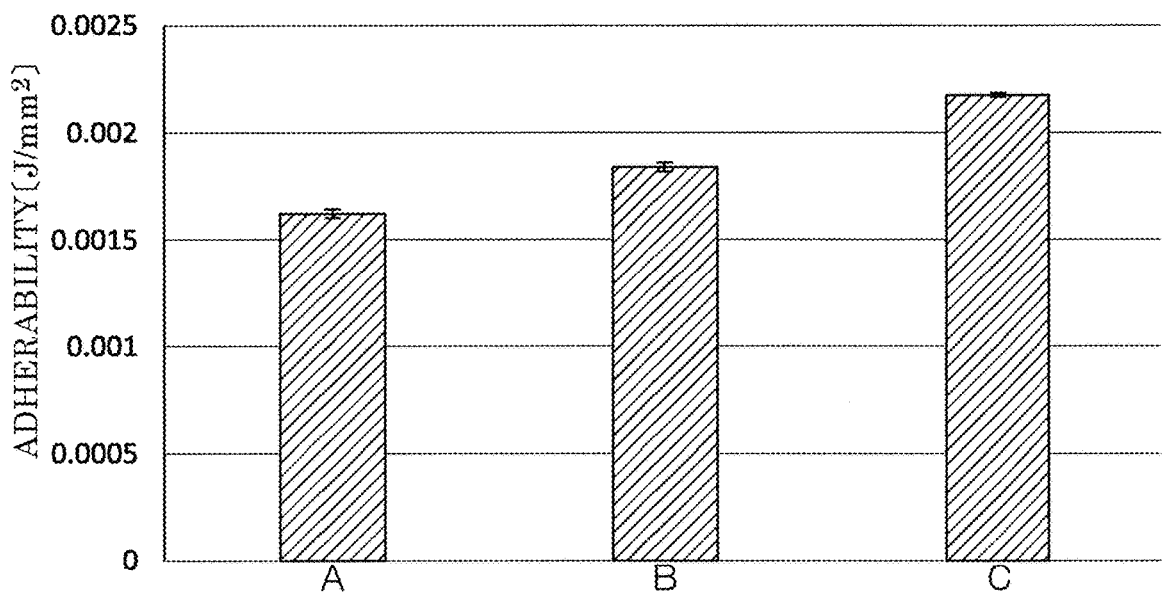
FIG. 44 shows a graph indicating the adherability of the specimens to the tilted surface.

FIG. 44 shows the adherability of the specimens (A) to (C) to the tilted surface. Herein, the adherability refers to energy consumed in the tilted surface per unit area of the tilted surface. As shown in this diagram, the specimen (C) showed a great adherability, and the specimen (A) showed a small adherability.

Figure 45:
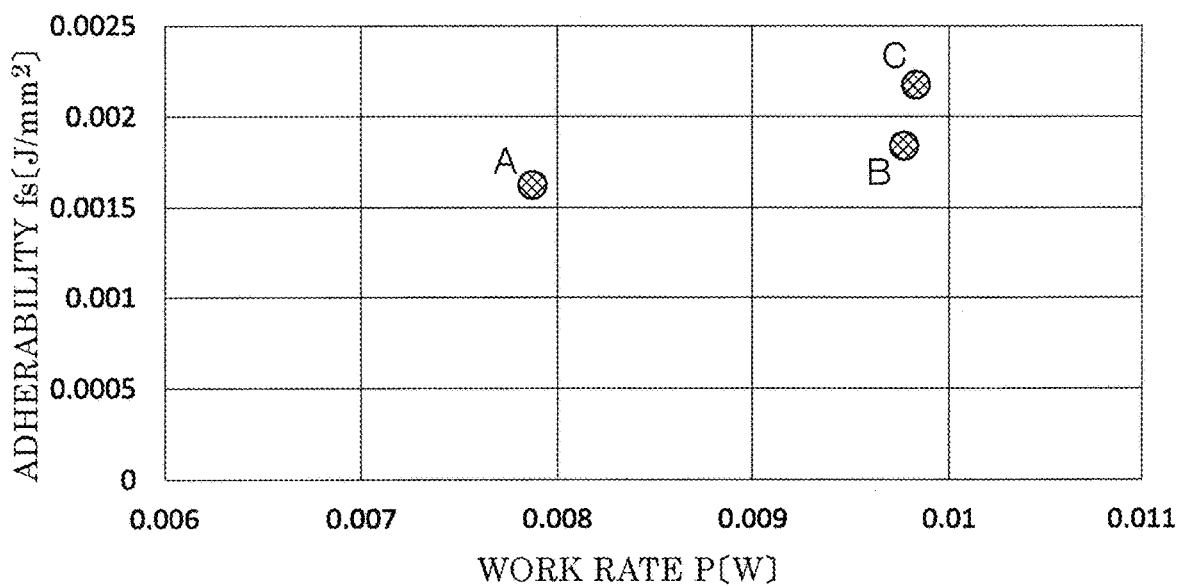
FIG. 45 shows mapping of the combination of the work rates and adherability of the specimens.

Mapping of the combination of the work rates of the specimens (A) to (C) shown in FIG. 43 and the adherability of the specimens (A) to (C) shown in FIG. 44 is shown in FIG. 45. As shown in FIG. 45, a plot of the specimen (A) and a plot of the specimen (B) are far apart from each other. Therefore, the specimen (A) and the specimen (B) that are difficult to differentiate from each other in FIG. 39 can be clearly differentiated by this mapping.

The mapping that combines the work rate and the adherability is considered to be associated with mouthfeel such as smoothness.

Figure 46:
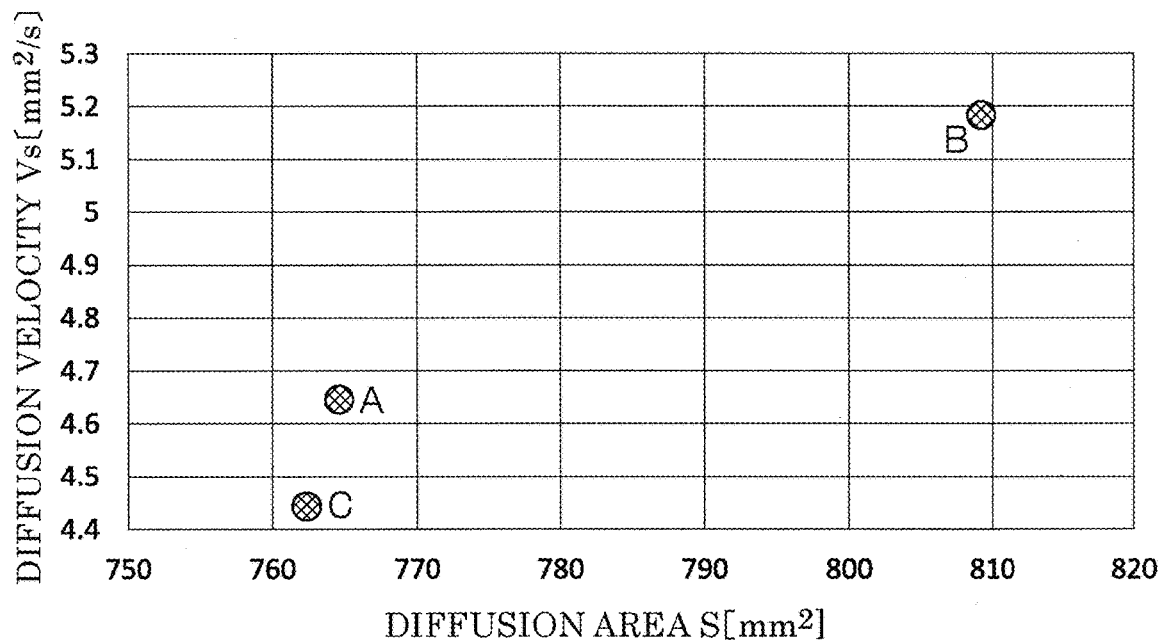
FIG. 46 shows mapping of the combination of the diffusion areas and diffusion velocities of the specimens.

Next, mapping of the combination of the diffusion areas of the specimens (A) to (C) shown in FIG. 27 and the diffusion areal velocities of the specimens (A) to (C) shown in FIG. 28 is shown in FIG. 46. As shown in FIG. 46, a plot of the specimen (A) and a plot of the specimen (B) are far apart from each other. Therefore, the specimen (A) and the specimen (B) that are difficult to differentiate from each other in FIG. 39 can be clearly differentiated by this mapping.

The mapping that combines the diffusion area and the diffusion areal velocity is considered to be associated with mouthfeel such as meltability and bitability.

Example 8

In the measurement device shown in FIG. 1, the influence of the material of the tilted surface of the tilted plate was checked with a tilted surface made of silicon and a tilted surface made of a false living body material (hydrophilic PVA) using polyvinyl alcohol which is closer to the inner surface of the oral cavity. 2 wt % water-solution Toromake (registered trademark) was used as a specimen. Further, the tilt angle of the tilted surface to the horizontal plane was set at 45°.

Figure 47:
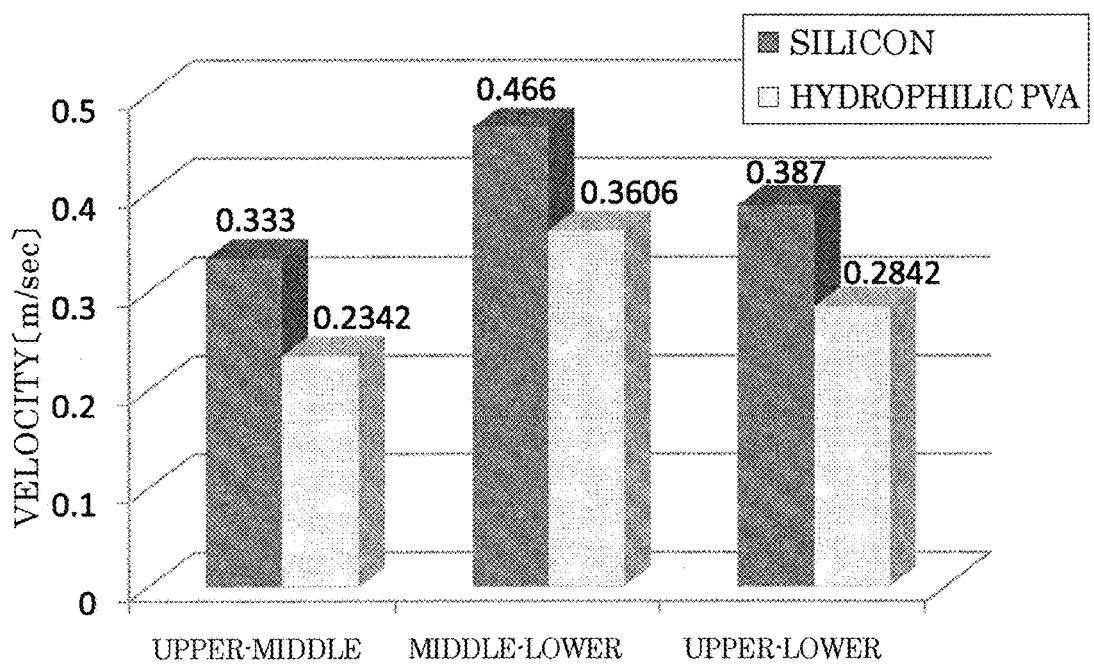
FIG. 47 shows a graph indicating the downward flow velocities of the specimen.

A graph indicating the downward flow velocities of the specimens is shown in FIG. 47. FIG. 47 shows the downward flow velocity of the specimen in the upstream part of the tilted surface from the detection of the specimen by the upper arrival check sensor (d) to the detection of the specimen by the middle arrival check sensor (e), the downward flow velocity of the specimen in the downstream part of the tilted surface from the detection of the specimen by the middle arrival check sensor (e) to the detection of the specimen by the lower arrival check sensor (f), and the downward flow velocity of the specimen in the whole tilted surface from the detection of the specimen by the upper arrival check sensor (d) to the detection of the specimen by the lower arrival check sensor (f). As shown in FIG. 47, it was found that the downward flow velocity on the hydrophilic PVA tilted surface was 20% to 30% lower than the downward flow velocity on the silicon tilted surface in all of the upstream part of the tilted surface, the downstream part, and the whole tilted surface. It was also found that the downward flow velocity in the upstream part tended to be lower than the downward flow velocity in the downstream part regardless of the material of the tilted surface.

Figure 48:
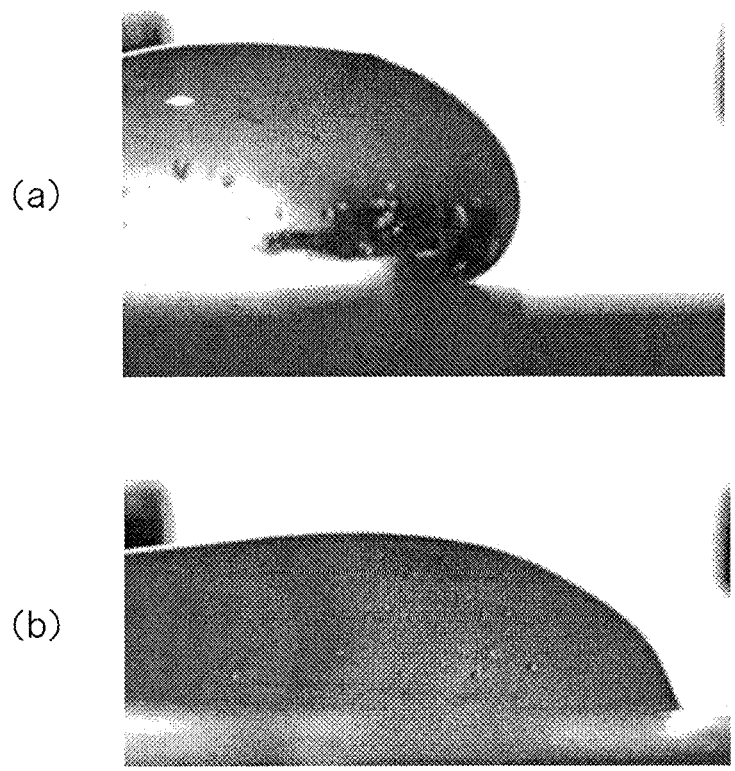
FIG. 48(a) shows a side image of the specimen downwardly flowing on a silicon tilted surface.
FIG. 48(b) shows a side image of the specimen downwardly flowing on a hydrophilic PVA tilted surface.

Side images of the shape of the tip of the downwardly flowing specimen are shown in FIG. 48(*a*) and FIG. 48(*b*). As shown in FIG. 48(*a*), the shape of the tip of the specimen downwardly flowing on the silicon tilted surface is nearly elliptic. In contrast, as shown in FIG. 48(*b*), the shape of the tip of the specimen downwardly flowing on the hydrophilic PVA tilted surface is nearly semielliptic, small in height, and has a large dynamic contact angle. This proves that the specimen is more easily diffused on the hydrophilic PVA tilted surface than on the silicon tilted surface.

Example 2

Figure 49:
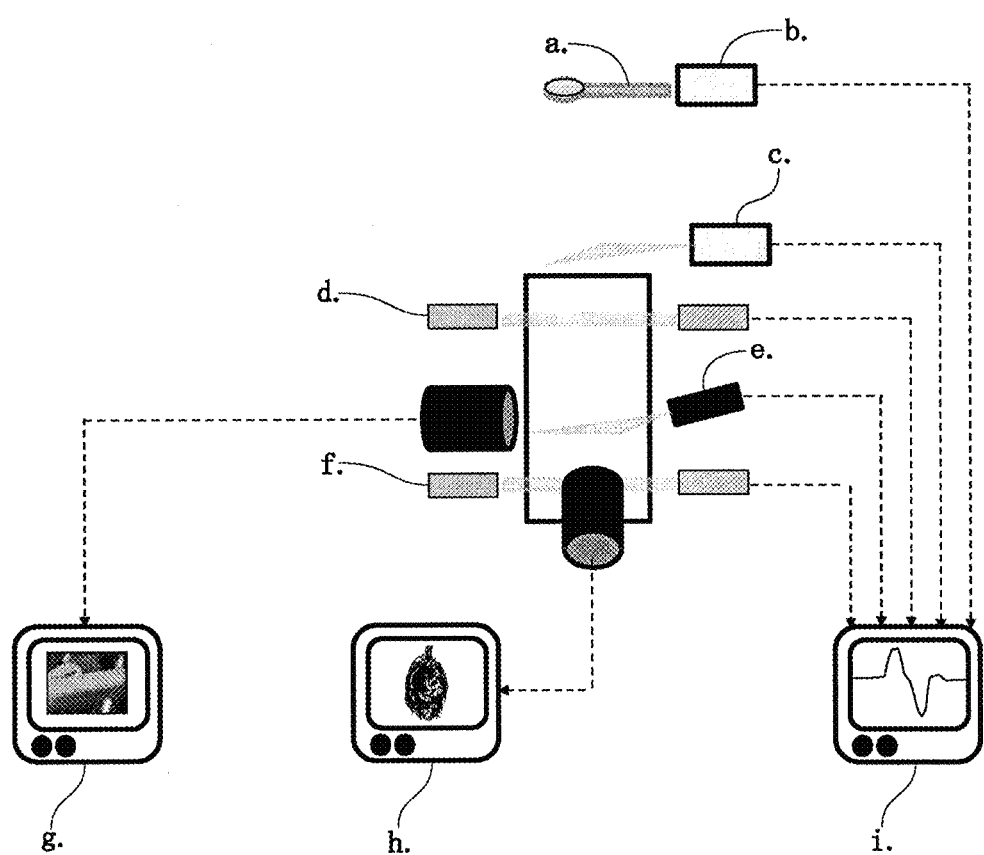
FIG. 49 shows a schematic diagram of the measurement device for properties of eating and swallowing.

FIG. 49 shows the measurement device according to Example 2 of the present invention. The configuration of the present measurement device is the same as that of the measurement device according to Example 1 shown in FIG. 1 except for the supply unit. Thus, a detailed description of the components other than the supply unit is omitted. The supply unit of the present measurement device includes an open-top container which is invertibly disposed above the tilted surface and which has a predetermined capacity. Herein, the open-top container is a plastic spoon (a). The size of a depressed portion of the spoon is 20 mm×28 mm×3 mm.

In the present example, the spoon (a) in which the specimen is put is inverted to supply the specimen onto the tilted surface. The inverting operation of the spoon is detected by the power check sensor (b). A milk beverage was supplied as the specimen, and the downward flow velocity and diffusion area of the specimen were measured. The specimen was supplied five times, and errors were checked.

Results of the five measurements were as follows: a downward flow velocity of 0.748±0.022 m/s and an error of 3% in the upstream part of the tilted surface, a downward flow velocity of 0.8258±0.010 m/s and an error of 5% in the downstream part of the tilted surface, and a downward flow velocity of 0.7514±0.014 m/s and an error of 2% in the whole tilted surface. Moreover, the diffusion area was 1391±63 (given unit), and an error was 5%.

Another kind of milk beverage was used as the specimen. Results of four measurements were as follows: a downward flow velocity of 0.7125±0.011 m/s and an error of 2% in the upstream part of the tilted surface, a downward flow velocity of 0.8050±0.014 m/s and an error of 2% in the downstream part of the tilted surface, and a downward flow velocity of 0.7514±0.010 m/s and an error of 2% in the whole tilted surface. Moreover, the diffusion area was 1358±21 (given unit), and an error was 2%.

As above, each of the downward flow velocity and diffusion area of the specimen had an error of 5% or less even when the specimen was supplied by the spoon, and reproducibility could be confirmed.

High reproducibility of measurement results could be confirmed even with the low-viscosity milk beverage.

Moreover, the example of the mapping of the combination of energy and the work rate per unit area, and the example of the mapping of the combination of the diffusion area and the diffusion areal velocity have been described in the present embodiment. However, the combinations of state parameters for use in mapping are not limited to the above combinations. Mapping can be performed by the combinations of various state parameters calculated by the present measurement device.

Furthermore, parameters for use in mapping are not limited to the state parameters calculated by the present measurement device. Mapping can also be performed by the combination of known parameters measured by a device other than the present measurement device and the state parameters calculated by the present measurement device. For example, mapping may be performed by the combination of a known parameter (physical property value) that represents physical properties of the specimen such as viscosity, density, specific gravity, or hardness, and the state parameters calculated by the present measurement device.

The present invention may have the following aspects <1> to <7>.

<1> A measurement device to estimate behavior and/or mouthfeel of a dynamic alimentary bolus, the measurement device comprising:

a tilted plate to which a specimen is supplied, a supply unit to supply the specimen to the tilted plate, a sensor to check the supply of the specimen to the tilted plate, and a sensor to check the arrival of the specimen halfway on the tilted plate;

a camera to photograph, from an upper surface of the specimen, the shape of the specimen downwardly flowing and/or falling on the tilted plate, and a camera to photograph, from a side surface of the specimen, the shape of the specimen downwardly flowing and/or falling on the tilted plate; and a sensor to check the discharge of the specimen from the supply unit, a data logger for time and velocity checked by each of the sensors, and a computer to calculate and process data regarding an image taken by each of the cameras.

<2> The measurement device to estimate the behavior and/or mouthfeel of the dynamic alimentary bolus according to <1>, further comprising a pressure sensor in the supply unit.

<3> The measurement device to estimate the behavior and/or mouthfeel of the dynamic alimentary bolus according to <1> or <2>, wherein the surface of the tilted plate is made of a material which simulates the inside of an oral cavity.

<4> The measurement device to estimate the behavior and/or mouthfeel of the dynamic alimentary bolus according to any one of <1> to <3>, wherein the arrival check sensor on the tilted plate is an optical sensor such as a photoelectric tube.

<5> The measurement device to estimate the behavior and/or mouthfeel of the dynamic alimentary bolus according to any one of <1> to <4>, wherein two or more arrival check sensors by optical sensors such as photoelectric tubes on the tilted plate are disposed, and a sensor to take still images is disposed between the arrival check sensors.

<6> The measurement device to estimate the behavior and/or mouthfeel of the dynamic alimentary bolus according to any one of <1> to <5>, wherein a discharge amount of the specimen is 1 ml or more.

<7> A method to calculate one of more of the following dynamic physical properties of a specimen by use of the device according to any one of the aspects of <1> to <6>: velocity, acceleration, pressure, force, shear velocity, wall surface shear stress, wall surface shear force, energy consumed in the wall surface, dynamic contact angle, downward flow area, falling area, downward flow locus, failing locus, thickness of the center during downward flowing of the specimen, and thickness of the center during falling.

INDUSTRIAL APPLICABILITY

Influence on behavior of an alimentary bolus during eating or swallowing can be quantitatively evaluated by the difference of physical property values and property values (such as water repellency) of the alimentary bolus, so that physical properties and forms of food optimal to people having difficulty in eating and swallowing (elderly people or the like) can be estimated, and food can be designed. In this instance, if accidental swallowing by elderly people or the like can be restrained, healthy life expectancy of Japanese people extends, leading to a great contribution to society by the reduction of medical expenses for health insurance or the like. Further, if compared with a simulation of a swallowing dynamic state using a computer, characteristics of the alimentary bolus can be more readily and objectively classified.

The literatures described in this description and the description of Japanese patent application on which Paris convention priority is claimed are incorporated herein by reference in their entirety.

The invention claimed is:

1. A measurement device which simulatively reproduces a swallowing state of an alimentary bolus and measures motion and shape of a specimen as the alimentary bolus, the measurement device comprising:
   a tilted member having a tilted surface;
   a supply unit to supply the specimen onto the tilted surface;
   a supply sensor to detect the specimen supplied from the supply unit onto the tilted surface;
   an arrival sensor to detect the specimen downwardly flowing or falling through a predetermined site on the tilted surface;
   a timing recording unit to record a detection timing of the specimen by the supply sensor and the arrival sensor;
   an upper camera to image, from a position above the tilted surface, the specimen downwardly flowing or falling on the tilted surface, to produce an upper image,
   a side camera to image, from a side of the tilted surface, the specimen downwardly flowing or falling on the tilted surface, to produce a side image; and
   a calculation unit which uses at least one of the output from the timing recording unit, the side image, and the upper image, to calculate a state parameter which represents a state of the specimen downwardly flowing or falling on the tilted surface,
   wherein the state parameter includes at least one of:
   velocity, acceleration, thickness, diffusion area on the tilted surface, and locus on the tilted surface, of the specimen downwardly flowing or falling on the tilted surface,
   dynamic contact angle of the specimen to the tilted surface, pressure of the specimen on the tilted surface, force of the specimen on the tilted surface, shear velocity of the specimen on the tilted surface, and shear stress of the specimen on the tilted surface,
   work amount or power consumed on the tilted surface, and impulse, and
   energy consumed on the tilted surface per unit area of the tilted surface, and diffusion areal velocity of the specimen on the tilted surface.

2. The measurement device according to claim 1, wherein the specimen has a volume of 1 ml or more and 50 ml or less.

3. The measurement device according to claim 1, wherein the tilted surface is made of a material which simulates a state of a surface of a living body inside an oral cavity or a pharynx.

4. The measurement device according to claim 1, wherein the supply unit comprises
   a nozzle disposed above the tilted surface, and
   a piston pump which supplies a predetermined amount of the specimen to the nozzle.

5. The measurement device according to claim 4, wherein the supply unit further comprises a pressure sensor to detect pressure inside the nozzle.

6. The measurement device according to claim 1, wherein the supply unit comprises an open-top container which is invertibly disposed above the tilted surface and which has a predetermined capacity.

7. The measurement device according to claim 1, wherein the arrival sensor is an optical sensor to optically detect the specimen.

8. The measurement device according to claim 1, wherein the arrival sensor comprises
   an upper sensor to detect the specimen downwardly flowing or falling through a first site on the tilted surface, and
   a lower sensor to detect the specimen downwardly flowing or falling through a second site on the tilted surface, the second site being apart a predetermined distance from the first predetermined sensor along a maximum tilt angle direction of the tilted surface.

9. The measurement device according to claim 8, wherein the arrival sensor further comprises a middle sensor to detect the specimen downwardly flowing or falling through a third site between the first site and the second site on the tilted surface.

10. The measurement device according to claim 1, wherein the side camera images the specimen using an output from the middle sensor as a trigger.

11. The measurement device according to claim 1, wherein the upper camera images the specimen using an output from the arrival sensor as a trigger.

12. A measurement method which uses the measurement device according to claim 1 to simulatively reproduce a swallowing state of an alimentary bolus and measure motion and shape of a specimen as a simulative alimentary bolus, the measurement method comprising:
   using at least one of an output from the supply sensor, an output from the arrival sensor, the side image, and the upper image, to calculate a state parameter which represents a state of the specimen downwardly flowing or falling on the tilted surface.

13. The measurement method according to claim 12, wherein
   the state parameters are combined, or a known parameter that represents physical properties of the specimen and one or more of the state parameters are combined, to perform mapping.

* * * * *